(12) United States Patent
Li

(10) Patent No.: US 12,091,429 B2
(45) Date of Patent: Sep. 17, 2024

(54) FLUORINATED PORPHYRIN DERIVATIVES FOR OPTOELECTRONIC APPLICATIONS

(71) Applicant: ARIZONA BOARD OF REGENTS ON BEHALF OF ARIZONA STATE UNIVERSITY, Scottsdale, AZ (US)

(72) Inventor: Jian Li, Tempe, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 747 days.

(21) Appl. No.: 17/251,824

(22) PCT Filed: Jul. 16, 2019

(86) PCT No.: PCT/US2019/041911
§ 371 (c)(1),
(2) Date: Dec. 14, 2020

(87) PCT Pub. No.: WO2020/018476
PCT Pub. Date: Jan. 23, 2020

(65) Prior Publication Data
US 2021/0261589 A1  Aug. 26, 2021

Related U.S. Application Data

(60) Provisional application No. 62/698,639, filed on Jul. 16, 2018.

(51) Int. Cl.
H01L 51/50 (2006.01)
C07F 15/00 (2006.01)
H10K 85/30 (2023.01)

(52) U.S. Cl.
CPC ....... C07F 15/0093 (2013.01); H10K 85/346 (2023.02)

(58) Field of Classification Search
None
See application file for complete search history.

(56) References Cited

U.S. PATENT DOCUMENTS 4,769,292 A   9/1988 Tang
5,707,745 A   1/1998 Forrest
(Continued)

FOREIGN PATENT DOCUMENTS

CN   1680366 A   10/2005
CN   1777663     5/2006
(Continued)

OTHER PUBLICATIONS

Yang et. al., Near Infrared Fluorescent and Phosphorescent Organic Light-Emitting Devices; Mater. Res. Soc. Symp. Proc. vol. 1154 © 2009 (Year: 2009).*
(Continued)

*Primary Examiner* — Gregory D Clark
(74) *Attorney, Agent, or Firm* — Riverside Law LLP

(57) ABSTRACT

Porphyrins and porphyrin derivatives of General Formulas I-V are suitable for use as donor-type materials for photovoltaic cells, absorbers for dye-sensitized solar cells, emitters for red and near infra-red organic light-emitting diodes (OLEDs), absorbers and re-emitters for organic concentrators (e.g., large area organic film for collection of sunlight) for small-size and high efficiency inorganic photovoltaics, and absorbers for hydrogeneration.

(Continued)

General Formula I

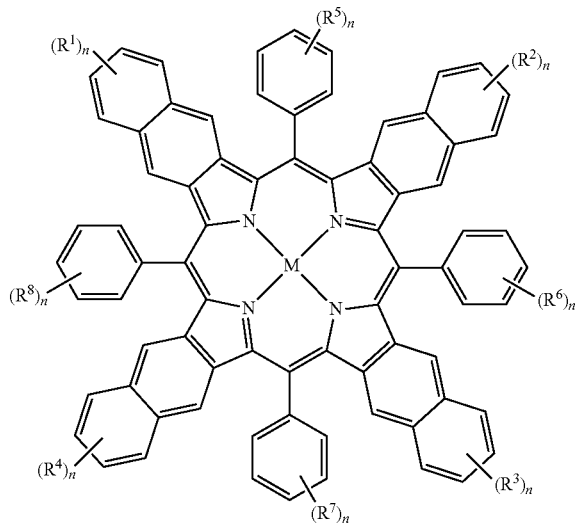

General Formula II

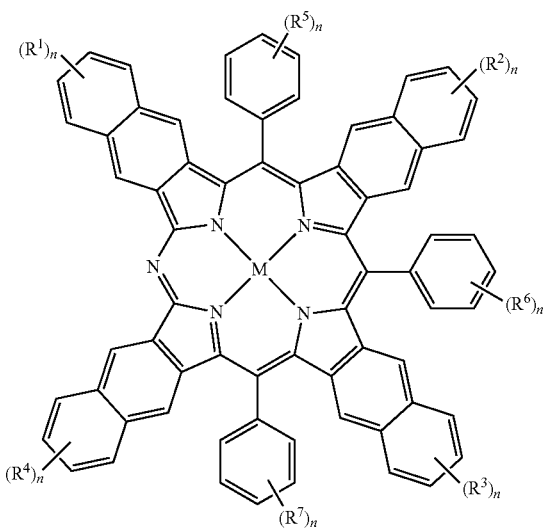

General Formula III

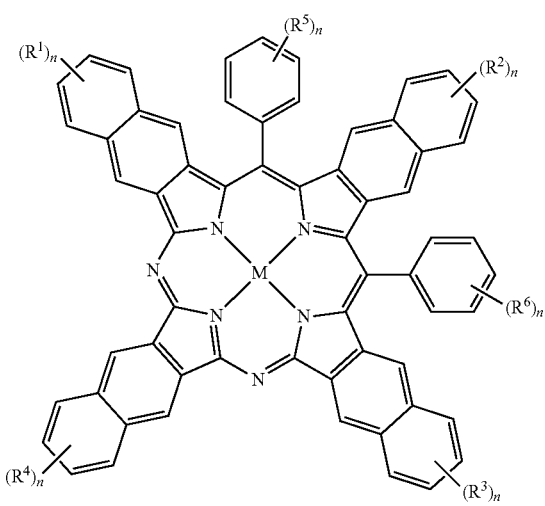

-continued

General Formula IV

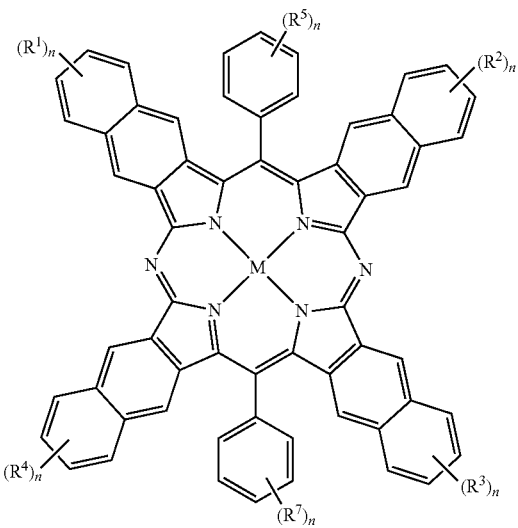

General Formula V

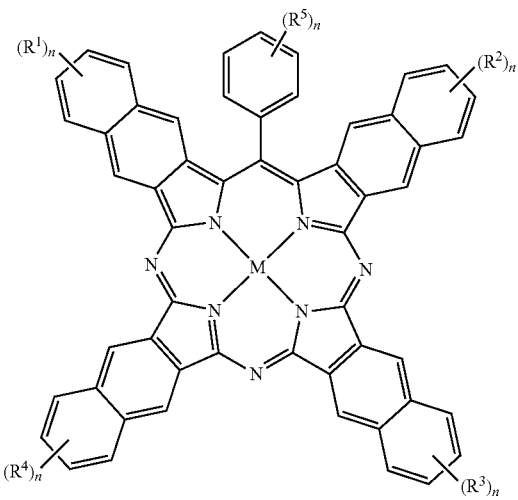

11 Claims, 9 Drawing Sheets

(56) References Cited

U.S. PATENT DOCUMENTS

| | | |
|---|---|---|
| 5,844,363 A | 12/1998 | Gu |
| 6,200,695 B1 | 3/2001 | Arai |
| 6,303,238 B1 | 10/2001 | Thompson |
| 6,780,528 B2 | 8/2004 | Tsuboyama |
| 7,002,013 B1 | 2/2006 | Chi |
| 7,037,599 B2 | 5/2006 | Culligan |
| 7,064,228 B1 | 6/2006 | Yu |
| 7,268,485 B2 | 9/2007 | Tyan |
| 7,279,704 B2 | 10/2007 | Walters |
| 7,332,232 B2 | 2/2008 | Ma |
| 7,442,797 B2 | 10/2008 | Itoh |
| 7,501,190 B2 | 3/2009 | Ise |
| 7,655,322 B2 | 2/2010 | Forrest |
| 7,854,513 B2 | 12/2010 | Quach |
| 7,947,383 B2 | 5/2011 | Ise |
| 8,133,597 B2 | 3/2012 | Yasukawa |

(56) References Cited

U.S. PATENT DOCUMENTS

| | | |
|---|---|---|
| 8,389,725 B2 | 3/2013 | Li |
| 8,617,723 B2 | 12/2013 | Stoessel |
| 8,816,080 B2 | 8/2014 | Li |
| 8,871,361 B2 | 10/2014 | Xia |
| 8,927,713 B2 | 1/2015 | Li |
| 8,946,417 B2 | 2/2015 | Jian |
| 9,059,412 B2 | 6/2015 | Zeng |
| 9,221,857 B2 | 12/2015 | Li |
| 9,224,963 B2 | 12/2015 | Li |
| 9,238,668 B2 | 1/2016 | Li |
| 9,312,502 B2 | 4/2016 | Li |
| 9,312,505 B2 | 4/2016 | Brooks |
| 9,318,725 B2 | 4/2016 | Li |
| 9,324,957 B2 | 4/2016 | Li |
| 9,382,273 B2 | 7/2016 | Li |
| 9,385,329 B2 | 7/2016 | Li |
| 9,425,415 B2 | 8/2016 | Li |
| 9,461,254 B2 | 10/2016 | Tsai |
| 9,550,801 B2 | 1/2017 | Li |
| 9,617,291 B2 | 4/2017 | Li |
| 9,673,409 B2 | 6/2017 | Li |
| 9,698,359 B2 | 7/2017 | Li |
| 9,711,739 B2 | 7/2017 | Li |
| 9,711,742 B2 | 7/2017 | Li |
| 9,755,163 B2 | 9/2017 | Li |
| 9,818,959 B2 | 11/2017 | Li |
| 9,879,039 B2 | 1/2018 | Li |
| 9,882,150 B2 | 1/2018 | Li |
| 9,899,614 B2 | 2/2018 | Li |
| 9,920,242 B2 | 3/2018 | Li |
| 9,923,155 B2 | 3/2018 | Li |
| 10,020,455 B2 | 7/2018 | Li |
| 10,158,091 B2 | 12/2018 | Li |
| 2001/0019782 A1 | 9/2001 | Igarashi |
| 2002/0068190 A1 | 6/2002 | Tsuboyama |
| 2003/0062519 A1 | 4/2003 | Yamazaki |
| 2003/0186077 A1 | 10/2003 | Chen |
| 2004/0230061 A1 | 11/2004 | Seo |
| 2005/0170207 A1 | 8/2005 | Ma |
| 2005/0260446 A1 | 11/2005 | Mackenzie |
| 2006/0024522 A1 | 2/2006 | Thompson |
| 2006/0073359 A1 | 4/2006 | Ise |
| 2006/0094875 A1 | 5/2006 | Itoh |
| 2006/0127696 A1 | 6/2006 | Stossel |
| 2006/0182992 A1 | 8/2006 | Nii |
| 2006/0202197 A1 | 9/2006 | Nakayama |
| 2006/0210831 A1 | 9/2006 | Sano |
| 2006/0255721 A1 | 11/2006 | Igarashi |
| 2006/0263635 A1 | 11/2006 | Ise |
| 2006/0286406 A1 | 12/2006 | Igarashi |
| 2007/0057630 A1 | 3/2007 | Nishita |
| 2007/0059551 A1 | 3/2007 | Yamazaki |
| 2007/0082284 A1 | 4/2007 | Stoessel |
| 2007/0103060 A1 | 5/2007 | Itoh |
| 2008/0001530 A1 | 1/2008 | Ise |
| 2008/0036373 A1 | 2/2008 | Itoh |
| 2008/0054799 A1 | 3/2008 | Satou |
| 2008/0079358 A1 | 4/2008 | Satou |
| 2008/0111476 A1 | 5/2008 | Choi |
| 2008/0241518 A1 | 10/2008 | Satou |
| 2008/0241589 A1 | 10/2008 | Fukunaga |
| 2008/0269491 A1 | 10/2008 | Jabbour |
| 2009/0026936 A1 | 1/2009 | Satou |
| 2009/0026939 A1 | 1/2009 | Kinoshita |
| 2009/0032989 A1 | 2/2009 | Karim |
| 2009/0039768 A1 | 2/2009 | Igarashi |
| 2009/0079340 A1 | 3/2009 | Kinoshita |
| 2009/0128008 A1 | 5/2009 | Ise |
| 2009/0218561 A1 | 9/2009 | Kitamura |
| 2009/0261721 A1 | 10/2009 | Murakami |
| 2009/0267500 A1 | 10/2009 | Kinoshita |
| 2010/0000606 A1 | 1/2010 | Thompson |
| 2010/0013386 A1 | 1/2010 | Thompson |
| 2010/0141127 A1 | 6/2010 | Xia |
| 2010/0171111 A1 | 7/2010 | Takada |
| 2010/0171418 A1 | 7/2010 | Kinoshita |
| 2010/0270540 A1 | 10/2010 | Chung |
| 2011/0028723 A1 | 2/2011 | Li |
| 2011/0049496 A1 | 3/2011 | Fukuzaki |
| 2011/0062858 A1 | 3/2011 | Yersin |
| 2011/0301351 A1 | 12/2011 | Li |
| 2012/0095232 A1 | 4/2012 | Li |
| 2012/0108806 A1 | 5/2012 | Li |
| 2012/0181528 A1 | 7/2012 | Takada |
| 2012/0199823 A1 | 8/2012 | Molt |
| 2012/0215001 A1 | 8/2012 | Li |
| 2012/0223634 A1 | 9/2012 | Xia |
| 2012/0264938 A1 | 10/2012 | Li |
| 2012/0273736 A1 | 11/2012 | James |
| 2012/0302753 A1 | 11/2012 | Li |
| 2013/0048963 A1 | 2/2013 | Beers |
| 2013/0137870 A1 | 5/2013 | Li |
| 2013/0168656 A1 | 7/2013 | Tsai |
| 2013/0203996 A1 | 8/2013 | Li |
| 2013/0237706 A1 | 9/2013 | Li |
| 2013/0341600 A1 | 12/2013 | Lin |
| 2014/0014922 A1 | 1/2014 | Lin |
| 2014/0027733 A1 | 1/2014 | Zeng |
| 2014/0066628 A1 | 3/2014 | Li |
| 2014/0073798 A1 | 3/2014 | Li |
| 2014/0084261 A1 | 3/2014 | Brooks |
| 2014/0114072 A1 | 4/2014 | Li |
| 2014/0147996 A1 | 5/2014 | Vogt |
| 2014/0148594 A1 | 5/2014 | Li |
| 2014/0191206 A1 | 7/2014 | Cho |
| 2014/0203248 A1 | 7/2014 | Zhou |
| 2014/0249310 A1 | 9/2014 | Li |
| 2014/0326960 A1 | 11/2014 | Kim |
| 2014/0330019 A1 | 11/2014 | Li |
| 2014/0364605 A1 | 12/2014 | Li |
| 2015/0008419 A1 | 1/2015 | Li |
| 2015/0018558 A1 | 1/2015 | Li |
| 2015/0028323 A1 | 1/2015 | Xia |
| 2015/0069334 A1 | 3/2015 | Xia |
| 2015/0105556 A1 | 4/2015 | Li |
| 2015/0162552 A1 | 6/2015 | Li |
| 2015/0194616 A1 | 7/2015 | Li |
| 2015/0207086 A1 | 7/2015 | Li |
| 2015/0228914 A1 | 8/2015 | Li |
| 2015/0274762 A1 | 10/2015 | Li |
| 2015/0287938 A1 | 10/2015 | Li |
| 2015/0311456 A1 | 10/2015 | Li |
| 2015/0318500 A1 | 11/2015 | Li |
| 2015/0349279 A1 | 12/2015 | Li |
| 2016/0028028 A1 | 1/2016 | Li |
| 2016/0028029 A1 | 1/2016 | Li |
| 2016/0043331 A1 | 2/2016 | Li |
| 2016/0072082 A1 | 3/2016 | Brooks |
| 2016/0133861 A1 | 5/2016 | Li |
| 2016/0133862 A1 | 5/2016 | Li |
| 2016/0194344 A1 | 7/2016 | Li |
| 2016/0197285 A1 | 7/2016 | Zeng |
| 2016/0197291 A1 | 7/2016 | Li |
| 2016/0285015 A1 | 9/2016 | Li |
| 2016/0359120 A1 | 12/2016 | Li |
| 2016/0359125 A1 | 12/2016 | Li |
| 2017/0005278 A1 | 1/2017 | Li |
| 2017/0012224 A1 | 1/2017 | Li |
| 2017/0040555 A1 | 2/2017 | Li |
| 2017/0047533 A1 | 2/2017 | Li |
| 2017/0066792 A1 | 3/2017 | Li |
| 2017/0069855 A1 | 3/2017 | Li |
| 2017/0077420 A1 | 3/2017 | Li |
| 2017/0125708 A1 | 5/2017 | Li |
| 2017/0236653 A1 | 8/2017 | Hanson |
| 2017/0267923 A1 | 9/2017 | Li |
| 2017/0271611 A1 | 9/2017 | Li |
| 2017/0301871 A1 | 10/2017 | Li |
| 2017/0305881 A1 | 10/2017 | Li |
| 2017/0331056 A1 | 11/2017 | Li |
| 2017/0342098 A1 | 11/2017 | Li |
| 2017/0373260 A1 | 12/2017 | Li |
| 2018/0006246 A1 | 1/2018 | Li |
| 2018/0053904 A1 | 2/2018 | Li |

(56) References Cited

U.S. PATENT DOCUMENTS

| | | | |
|---|---|---|---|
| 2018/0130960 A1 | 5/2018 | Li |
| 2018/0138428 A1 | 5/2018 | Li |
| 2018/0148464 A1 | 5/2018 | Li |
| 2018/0159051 A1 | 6/2018 | Li |
| 2018/0166655 A1 | 6/2018 | Li |
| 2018/0175329 A1 | 6/2018 | Li |
| 2018/0194790 A1 | 7/2018 | Li |
| 2018/0219161 A1 | 8/2018 | Li |
| 2018/0226592 A1 | 8/2018 | Li |
| 2018/0226593 A1 | 8/2018 | Li |
| 2018/0277777 A1 | 9/2018 | Li |
| 2018/0301641 A1 | 10/2018 | Li |
| 2018/0312750 A1 | 11/2018 | Li |
| 2018/0331307 A1 | 11/2018 | Li |
| 2018/0334459 A1 | 11/2018 | Li |
| 2018/0337345 A1 | 11/2018 | Li |
| 2018/0337349 A1 | 11/2018 | Li |
| 2018/0337350 A1 | 11/2018 | Li |
| 2019/0013485 A1 | 1/2019 | Li |
| 2019/0067602 A1 | 2/2019 | Li |
| 2019/0109288 A1 | 4/2019 | Li |
| 2019/0194536 A1 | 6/2019 | Li |
| 2019/0259963 A1 | 8/2019 | Li |
| 2019/0276485 A1 | 9/2019 | Li |
| 2019/0312217 A1 | 10/2019 | Li |
| 2019/0367546 A1 | 12/2019 | Li |
| 2019/0389893 A1 | 12/2019 | Li |
| 2020/0006677 A1* | 1/2020 | Kim | C07D 487/22 |
| 2020/0006678 A1 | 1/2020 | Li |
| 2020/0071330 A1 | 3/2020 | Li |
| 2020/0075868 A1 | 3/2020 | Li |
| 2020/0119288 A1 | 4/2020 | Li |
| 2020/0152891 A1 | 5/2020 | Li |
| 2020/0227656 A1 | 7/2020 | Li |
| 2020/0227660 A1 | 7/2020 | Li |
| 2020/0239505 A1 | 7/2020 | Li |
| 2020/0243776 A1 | 7/2020 | Li |
| 2020/0287153 A1 | 9/2020 | Li |
| 2020/0332185 A1 | 10/2020 | Li |
| 2020/0373505 A1 | 11/2020 | Li |
| 2020/0403167 A1 | 12/2020 | Li |
| 2021/0024526 A1 | 1/2021 | Li |
| 2021/0024559 A1 | 1/2021 | Li |
| 2021/0047296 A1 | 2/2021 | Li |
| 2021/0091316 A1 | 3/2021 | Li |

FOREIGN PATENT DOCUMENTS

| | | |
|---|---|---|
| CN | 1894269 A | 1/2007 |
| CN | 101667626 | 3/2010 |
| CN | 102449108 A | 5/2012 |
| CN | 102892860 A | 1/2013 |
| CN | 102971396 A | 3/2013 |
| CN | 103102372 | 5/2013 |
| CN | 104232076 A | 12/2014 |
| CN | 104377231 | 2/2015 |
| CN | 104693243 A | 6/2015 |
| CN | 105367605 A | 3/2016 |
| CN | 105418591 A | 3/2016 |
| EP | 1874893 A1 | 1/2008 |
| EP | 1874894 A1 | 1/2008 |
| EP | 1919928 A1 | 5/2008 |
| EP | 2036907 A1 | 3/2009 |
| EP | 2096690 | 9/2009 |
| EP | 2112213 A2 | 10/2009 |
| EP | 2417217 A2 | 2/2012 |
| EP | 2574613 | 4/2013 |
| EP | 2711999 A2 | 3/2014 |
| JP | 2002105055 | 4/2002 |
| JP | 2005267557 | 9/2005 |
| JP | 2005310733 A | 11/2005 |
| JP | 2006047240 A | 2/2006 |
| JP | 2006232784 A | 9/2006 |
| JP | 2006242080 | 9/2006 |
| JP | 2006242081 A | 9/2006 |
| JP | 2006256999 A | 9/2006 |
| JP | 2006257238 A | 9/2006 |
| JP | 2006261623 A | 9/2006 |
| JP | 2006290988 A | 10/2006 |
| JP | 2006313796 A | 11/2006 |
| JP | 2006332622 A | 12/2006 |
| JP | 2006351638 A | 12/2006 |
| JP | 2007019462 A | 1/2007 |
| JP | 2007031678 | 2/2007 |
| JP | 2007042875 A | 2/2007 |
| JP | 2007053132 A | 3/2007 |
| JP | 2007066581 | 3/2007 |
| JP | 2007073620 A | 3/2007 |
| JP | 2007073845 A | 3/2007 |
| JP | 2007073900 A | 3/2007 |
| JP | 2007080593 | 3/2007 |
| JP | 2007080677 A | 3/2007 |
| JP | 2007088105 | 4/2007 |
| JP | 2007088164 A | 4/2007 |
| JP | 2007096259 A | 4/2007 |
| JP | 2007099765 A | 4/2007 |
| JP | 2007110067 | 4/2007 |
| JP | 2007110102 A | 4/2007 |
| JP | 2007258550 A | 10/2007 |
| JP | 2007324309 A | 12/2007 |
| JP | 2008010353 A | 1/2008 |
| JP | 2008090085 | 4/2008 |
| JP | 2008091860 A | 4/2008 |
| JP | 2008103535 A | 5/2008 |
| JP | 2008109085 | 5/2008 |
| JP | 2008109103 A | 5/2008 |
| JP | 2008160087 A | 7/2008 |
| JP | 2008198801 A | 8/2008 |
| JP | 2008270729 A | 11/2008 |
| JP | 2008270736 | 11/2008 |
| JP | 2009016184 A | 1/2009 |
| JP | 2009016579 | 1/2009 |
| JP | 2009032977 A | 2/2009 |
| JP | 2009032988 A | 2/2009 |
| JP | 2009076509 A | 4/2009 |
| JP | 2009266943 A | 11/2009 |
| JP | 2009267171 A | 11/2009 |
| JP | 2009267244 | 11/2009 |
| JP | 2009267244 A | 11/2009 |
| JP | 2009272339 A | 11/2009 |
| JP | 2009283891 A | 12/2009 |
| JP | 2010135689 | 6/2010 |
| JP | 2010135689 A | 6/2010 |
| JP | 5604505 | 9/2012 |
| JP | 2012222255 A | 11/2012 |
| JP | 2013525436 | 6/2013 |
| JP | 2014221807 A | 11/2014 |
| JP | 2015081257 A | 4/2015 |
| KR | 20060115371 | 11/2006 |
| KR | 20070061830 | 6/2007 |
| KR | 20070112465 | 11/2007 |
| KR | 20130043460 | 4/2013 |
| KR | 101338250 | 12/2013 |
| TW | 200701835 | 1/2007 |
| TW | 201307365 A | 2/2013 |
| TW | 201710277 | 3/2017 |
| WO | 0070655 A2 | 11/2000 |
| WO | 2004003108 | 1/2004 |
| WO | 2004085450 | 10/2004 |
| WO | 2004108857 | 12/2004 |
| WO | 2005042444 A2 | 5/2005 |
| WO | 2005042550 A1 | 5/2005 |
| WO | 2005113704 | 12/2005 |
| WO | 2006033440 A1 | 3/2006 |
| WO | 2006067074 | 6/2006 |
| WO | 2006098505 A1 | 9/2006 |
| WO | 2006113106 | 10/2006 |
| WO | 2006115299 A1 | 11/2006 |
| WO | 2006115301 | 11/2006 |
| WO | 2007034985 A1 | 3/2007 |
| WO | 2007069498 A1 | 6/2007 |
| WO | 2008054578 | 5/2008 |
| WO | 2008066192 A1 | 6/2008 |
| WO | 2008066195 A1 | 6/2008 |

(56) References Cited

FOREIGN PATENT DOCUMENTS

| WO | 2008066196 | A1 | 6/2008 |
|---|---|---|---|
| WO | 2008101842 | A1 | 8/2008 |
| WO | 2008117889 | | 10/2008 |
| WO | 2008123540 | | 10/2008 |
| WO | 2009017211 | A1 | 2/2009 |
| WO | 2009023667 | | 2/2009 |
| WO | 2009086209 | | 7/2009 |
| WO | 2009111299 | | 9/2009 |
| WO | 2010007098 | A1 | 1/2010 |
| WO | 2010056669 | | 5/2010 |
| WO | 2010093176 | | 8/2010 |
| WO | 2010105141 | | 9/2010 |
| WO | 2010118026 | A2 | 10/2010 |
| WO | 2011064335 | A1 | 6/2011 |
| WO | 2011070989 | A1 | 6/2011 |
| WO | 2011089163 | | 7/2011 |
| WO | 2011137429 | A2 | 11/2011 |
| WO | 2011137431 | A2 | 11/2011 |
| WO | 2012063471 | | 5/2012 |
| WO | 2012074909 | | 6/2012 |
| WO | 2012112853 | A1 | 8/2012 |
| WO | 2012116231 | | 8/2012 |
| WO | 2012142387 | | 10/2012 |
| WO | 2012162488 | A1 | 11/2012 |
| WO | 2012163471 | A1 | 12/2012 |
| WO | 2013130483 | A1 | 9/2013 |
| WO | 2014016611 | | 1/2014 |
| WO | 2014031977 | | 2/2014 |
| WO | 2014047616 | A1 | 3/2014 |
| WO | 2014109814 | | 7/2014 |
| WO | 2014208271 | | 12/2014 |
| WO | 2015027060 | A1 | 2/2015 |
| WO | 2015131158 | | 9/2015 |
| WO | 2016025921 | | 2/2016 |
| WO | 2016029137 | | 2/2016 |
| WO | 2016029186 | | 2/2016 |
| WO | 2016197019 | | 12/2016 |
| WO | 2018071697 | | 4/2018 |
| WO | 2018140765 | | 8/2018 |
| WO | 2019079505 | | 4/2019 |
| WO | 2019079508 | | 4/2019 |
| WO | 2019079509 | | 4/2019 |
| WO | 2019236541 | | 12/2019 |
| WO | 2020018476 | | 1/2020 |

OTHER PUBLICATIONS

Ayan Maity et al., "Room-temperature synthesis of cyclometalated iridium(III) complexes; kinetic isomers and reactive functionalities" Chem. Sci., vol. 4, pp. 1175-1181 (2013).
Baldo et al., "Highly Efficient Phosphorescent Emission from Organic Electroluminescent Devices," Nature, vol. 395, Sep. 10, 1998, pp. 151-154.
Baldo et al., "Very high-efficiency green organic light-emitting devices based on electrophosphorescence," Applied Physics Letters, vol. 75, No. 1, Jul. 5, 1999, pp. 4-6.
Barry O'Brien et al.: White organic light emitting diodes using Pt-based red, green and blue phosphorescent dopants. Proc. SPIE, vol. 8829, pp. 1-6, Aug. 25, 2013.
Barry O'Brien et al., "High efficiency white organic light emitting diodes employing blue and red platinum emitters," Journal of Photonics for Energy, vol. 4, 2014, pp. 043597-1-8.
Brian W. D'Andrade et al., "Controlling Exciton Diffusion in Multilayer White Phosphorescent Organic Light Emitting Devices", Adv. Mater., vol. 14, No. 2, Jan. 16, 2002, pp. 147-151.
Chew, S. et al: Photoluminescence and electroluminescence of a new blue-emitting homoleptic iridium complex. Applied Phys. Letters; vol. 88, pp. 093510-1-093510-3, 2006.
Chi et al.; Transition-metal phosphors with cyclometalating ligands: fundamentals and applications, Chemical Society Reviews, vol. 39, No. 2, Feb. 2010, pp. 638-655.

Chi-Ming Che et al. "Photophysical Properties and OLEO Applications of Phosphorescent Platinum(II) Schiff Base Complexes," Chem. Eur. J., vol. 16, 2010, pp. 233-247.
Christoph Ulbricht et al., "Synthesis and Characterization of Oxetane-Functionalized Phosphorescent Ir(III)-Complexes", Macromol. Chem. Phys. 2009, 210, pp. 531-541.
D.F. O'Brien et al., "Improved energy transfer in electrophosphorescent devices," Appl. Phys. Lett., vol. 74, No. 3, Jan. 18, 1999, pp. 442-444.
Dan Wang et al., "Carbazole and arylamine functionalized iridium complexes for efficient electro-phosphorescent light-emitting diodes", Inorganica Chimica Acta 370 (2011) pp. 340-345.
Dileep A. K. Vezzu et al., "Highly Luminescent Tetradentate Bis-Cyclometalated Platinum Complexes: Design, Synthesis, Structure, Photophysics, and Electroluminescence Application," Inorg. Chem., vol. 49, 2010, pp. 5107-5119.
Dorwald; "Side Reactions in Organic Synthesis: A Guide to Successful Synthesis Design," Chapter 1, 2005 Wiley-VCH Verlag Gmbh & Co. KGaA, Wienheim, 32 pages.
Eric Turner et al., "Cyclometalated Platinum Complexes with Luminescent Quantum Yields Approaching 100%," Inorg. Chem., 2013, vol. 52, pp. 7344-7351.
Evan L. Williams et al., "Excimer-Based White Phosphorescent Organic Light Emitting Diodes with Nearly 100% Internal Quantum Efficiency," Adv. Mater., vol. 19, 2007, pp. 197-202.
Glauco Ponterini et al., "Comparison of Radiationless Decay Processes in Osmium and Platinum Porphyrins," J. Am. Chem. Soc., vol. 105, No. 14, 1983, pp. 4639-4645.
Guijie Li et al., "Efficient and stable red organic light emitting devices from a tetradentate cyclometalated platinum complex," Organic Electronics, 2014, vol. 15 pp. 1862-1867.
Guijie Li et al., "Modifying Emission Spectral Bandwidth of Phosphorescent Platinum(II) Complexes Through Synthetic Control," Inorg. Chem. 2017, 56, 8244-8256.
Guijie Li et al., Efficient and Stable White Organic Light-Emitting Diodes Employing a Single Emitter, Adv. Mater., 2014, vol. 26, pp. 2931-2936.
Hirohiko Fukagawa et al., "Highly Efficient and Stable Red Phosphorescent Organic Light-Emitting Diodes Using Platinum Complexes," Adv. Mater., 2012, vol. 24, pp. 5099-5103.
Hoe-Joo Seo et al., "Blue phosphorescent iridium(III) complexes containing carbazole-functionalized phenyl pyridine for organic light-emitting diodes: energy transfer from carbazolyl moieties to iridium(III) cores", RSC Advances, 2011, 1, pp. 755-757.
Huaijun Tang et al., "Novel yellow phosphorescent iridium complexes containing a carbazoleeoxadiazole unit used in polymeric light-emitting diodes", Dyes and Pigments 91 (2011) pp. 413-421.
Ivaylo Ivanov et al., "Comparison of the INDO band structures of polyacetylene, polythiophene, polyfuran, and polypyrrole," Synthetic Metals, vol. 116, Issues 1-3, Jan. 1, 2001, pp. 111-114.
Jack W. Levell et al., "Carbazole/iridium dendrimer side-chain phosphorescent copolymers for efficient light emitting devices", New J. Chem., 2012, vol. 36, pp. 407-413.
Jan Kalinowski et al., "Light-emitting devices based on organometallic platinum complexes as emitters," Coordination Chemistry Reviews, vol. 255, 2011, pp. 2401-2425.
Jeonghun Kwak et al., "Bright and Efficient Full-Color Colloidal Quantum Dot Light-Emitting Diodes Using an Inverted Device Structure," Nano Letters 12, Apr. 2, 2012, pp. 2362-2366.
Ji Hyun Seo et al., "Efficient blue-green organic light-emitting diodes based on heteroleptic tris-cyclometalated iridium (III) complexes". Thin Solid Films, vol. 517, pp. 1807-1810 (2009).
Kai Li et al., "Light-emitting platinum(II) complexes supported by tetradentate dianionic bis(N-heterocyclic carbene) ligands: towards robust blue electrophosphors," Chem. Sci., 2013, vol. 4, pp. 2630-2644.
Ke Feng et al., "Norbornene-Based Copolymers Containing Platinum Complexes and Bis(carbazolyl)benzene Groups in Their Side-Chains," Macromolecules, vol. 42, 2009, pp. 6855-6864.
Kumar, et al., "Near infrared phosphorescent polymeric nanomicelles: efficient optical probes for tumor imaging and detection,", ACS Appl Mater Interfaces, 2009, 1, 1474-1481.

(56) References Cited

OTHER PUBLICATIONS

Kwon-Hyeon Kim et al., "Controlling Emitting Dipole Orientation with Methyl Substituents on Main Ligand of Iridium Complexes for Highly Efficient Phosphorescent Organic Light-Emitting Diodes", Adv. Optical Mater. 2015, 3, pp. 1191-1196.

Kwon-Hyeon Kim et al., "Crystal Organic Light-Emitting Diodes with Perfectly Oriented Non-Doped Pt-Based Emitting Layer", Adv. Mater. 2016, 28, pp. 2526-2532.

Maestri et al., "Absorption Spectra and Luminescence Properties of Isomeric Platinum (II) and Palladium (II) Complexes Containing 1,1'-Biphenyldiyl, 2-Phenylpyridine, and 2,2'-Bipyridine as Ligands," Helvetica Chimica Acta, vol. 71, Issue 5, Aug. 10, 1988, pp. 1053-1059.

Marc Lepeltier et al., "Efficient blue green organic light-emitting devices based on a monofluorinated heteroleptic iridium(III) complex," Synthetic Metals, vol. 199, 2015, pp. 139-146.

Matthew J. Jurow et al., "Understanding and predicting the orientation of heteroleptic phosphors in organic light-emitting materials", Nature Materials, vol. 15, Jan. 2016, pp. 85-93.

Murakami; JP 2007324309, English machine translation from EPO, dated Dec. 13, 2007, 89 pages.

Nicholas R. Evans et al., "Triplet Energy Back Transfer in Conjugated Polymers with Pendant Phosphorescent Iridium Complexes," J. Am. Chem. Soc., vol. 128, 2006, pp. 6647-6656.

Satake et al., "Interconvertible Cationic and Neutral Pyridinylimidazole η3-Allylpalladium Complexes. Structural Assignment by 1H, 13C, and 15N NMR and X-ray Diffraction", Organometallics, vol. 18, No. 24, 1999, pp. 5108-5111.

Shih-Chun Lo et al. "High-Triplet-Energy Dendrons: Enhancing the Luminescence of Deep Blue Phosphorescent Indium(III) Complexes" J. Am. Chem. Soc., vol. 131, 2009, pp. 16681-16688.

Shiro Koseki et al., "Spin-orbit coupling analyses of the geometrical effects on phosphorescence in Ir(ppy)3 and its derivatives", J. Phys. Chem. C, vol. 117, pp. 5314-5327 (2013).

Shizuo Tokito et al. "Confinement of triplet energy on phosphorescent molecules for highly-efficient organic blue-light-emitting devices" Applied Physics Letters, vol. 83, No. 3, Jul. 21, 2003, pp. 569-571.

Sommer, et al., "Efficient Nier-Infrared Polymer and Organic Light-Emitting Diodes Based on Electrophosphorescence from (Tetraphenyltetranaptho[2,3]porphyrine)platinum(II)," ACS Appl Mater Interfaces, 2009, 1, 274-278.

Stefan Bernhard, "The First Six Years: A Report," Department of Chemistry, Princeton University, May 2008, 11 pages.

Stephen R. Forrest, "The path to ubiquitous and low-cost organic electronic appliances on plastic," Nature, vol. 428, Apr. 29, 2004, pp. 911-918.

Steven C. F. Kui et al., "Robust phosphorescent platinum(II) complexes with tetradentate O^N^C^N ligands: high efficiency OLEDs with excellent efficiency stability," Chem. Commun., 2013, vol. 49, pp. 1497-1499.

Steven C. F. Kui et al., "Robust Phosphorescent Platinum(II) Complexes Containing Tetradentate O^N^C^N Ligands: Excimeric Excited State and Application in Organic White-Light-Emitting Diodes," Chem. Eur. J., 2013, vol. 19, pp. 69-73.

Sylvia Bettington et al. "Tris-Cyclometalated Iridium(III) Complexes of Carbazole(fluorenyl)pyridine Ligands: Synthesis, Redox and Photophysical Properties, and Electrophosphorescent Light-Emitting Diodes" Chemistry: A European Journal, 2007, vol. 13, pp. 1423-1431.

Tyler Fleetham et al., "Efficient "pure" blue OLEDs employing tetradentate Pt complexes with a narrow spectral bandwidth," Advanced Materials (Weinheim, Germany), Vo. 26, No. 41, 2014, pp. 7116-7121.

Tyler Fleetham et al., "Efficient Red-Emitting Platinum Complex with Long Operational Stability," ACS Appl. Mater. Interfaces 2015, 7, 16240-16246.

V. Adamovich et al., "High efficiency single dopant white electrophosphorescent light emitting diodes", New J. Chem, vol. 26, pp. 1171-1178. 2002.

Vanessa Wood et al., "Colloidal quantum dot light-emitting devices," Nano Reviews 1, Jul. 2010, pp. 5202. (7 pages).

Wong. Challenges in organometallic research—Great opportunity for solar cells and OLEDs. Journal of Organometallic Chemistry 2009, vol. 694, pp. 2644-2647.

Xiao-Chu Hang et al., "Highly Efficient Blue-Emitting Cyclometalated Platinum(II) Complexes by Judicious Molecular Design," Angewandte Chemie, International Edition, vol. 52, Issue 26, Jun. 24, 2013, pp. 6753-6756.

Xiaofan Ren et al., "Ultrahigh Energy Gap Hosts in Deep Blue Organic Electrophosphorescent Devices," Chem. Mater., vol. 16, 2004, pp. 4743-4747.

Xin Li et al., "Density functional theory study of photophysical properties of iridium (III) complexes with phenylisoquinoline and phenylpyridine ligands", The Journal of Physical Chemistry C, 2011, vol. 115, No. 42, pp. 20722-20731.

Ying Yang et al., "Induction of Circularly Polarized Electroluminescence from an Achiral Light-Emitting Polymer via a Chiral Small-Molecule Dopant," Advanced Materials, vol. 25, Issue 18, May 14, 2013, pp. 2624-2628.

Z Liu et al., "Green and blue-green phosphorescent heteroleptic iridium complexes containing carbazole-functionalized beta-diketonate for non-doped organic light-emitting diodes", Organic Electronics 9 (2008) pp. 171-182.

Z Xu et al., "Synthesis and properties of iridium complexes based 1,3,4-oxadiazoles derivatives", Tetrahedron 64 (2008) pp. 1860-1867.

Zhi-Qiang Zhu et. al., "Efficient Cyclometalated Platinum(II) Complex with Superior Operational Stability," Adv. Mater. 29 (2017) 1605002, pp. 1-5.

Zhi-Qiang Zhu et.al., "Harvesting All Electrogenerated Excitons through Metal Assisted Delayed Fluorescent Materials," Adv. Mater. 27 (2015) 2533-2537.

\* cited by examiner

FLUORINATED PORPHYRIN DERIVATIVES FOR OPTOELECTRONIC APPLICATIONS

CROSS-REFERENCE TO RELATED APPLICATIONS

The present application is a 35 U.S.C. § 371 national phase application from, and claiming priority to, International Patent Application No. PCT/US2019/041911, filed Jul. 16, 2019, which claims priority under 35 U.S.C. § 119(e) to U.S. Provisional Patent Application No. 62/698,639, filed Jul. 16, 2018, all of which are incorporated by reference herein in their entireties.

STATEMENT REGARDING FEDERALLY SPONSORED RESEARCH OR DEVELOPMENT

This invention was made with government support under 0748867 awarded by the National Science Foundation. The government has certain rights in the invention.

TECHNICAL FIELD

This invention relates to fluorinated porphyrin derivatives for optoelectronic applications such as organic light-emitting diodes (OLEDs), organic photovoltaics, organic concentrators, and hydrogen generation systems.

BACKGROUND OF THE INVENTION

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

Metal phthalocyanines (MPcs), metal porphyrins, and their derivatives have been investigated for over a hundred years. Phthalocyanines (Pcs) are used as blue and green colorants for photographic, paint, printing, plastics, and textile industries. Copper phthalocyanine (CuPc), which has a good hole mobility ($5\times10^{-3}$ cm$^2$/V·s) and strong absorption in the range of 550-750 nm with peak values of extinction coefficient more than over $10^5$ L·[mol·cm]$^{-1}$, has been incorporated into organic light emitting diodes (OLEDs) as a hole injection material and into organic photovoltaic cells as donor-type absorbers. Porphyrin-based compounds are of interest in molecular electronics and supramolecular building blocks. Most porphyrins and azaporphyrins have high molecular weights and tend to have high sublimation temperatures, a factor in maintaining high purity of materials. However, porphyrins with high sublimation temperatures can decompose, thereby reducing production yield.

There is need in the art for novel materials for optoelectronic devices. The present invention fulfills this unmet need.

SUMMARY OF THE INVENTION

The present invention relates to a complex represented by one of General Formulas I-V and to optoelectronic devices, including organic light-emitting diodes, comprising said complex.

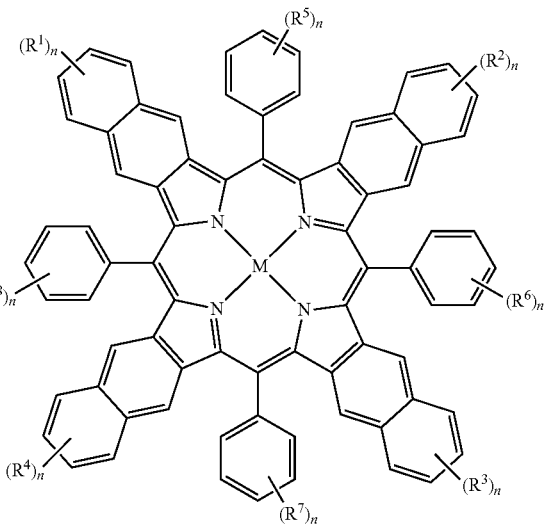

General Formula I

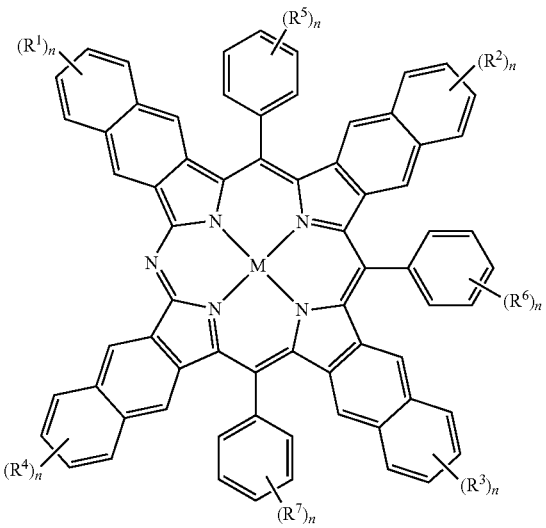

General Formula II

-continued

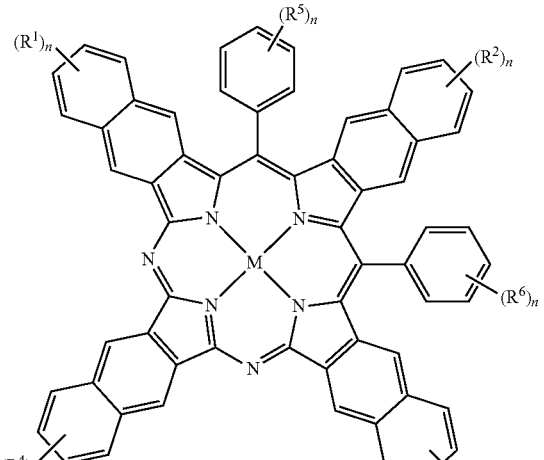

General Formula III

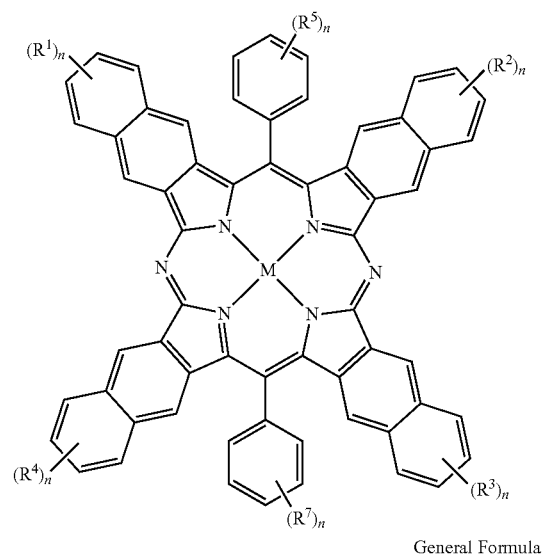

General Formula IV

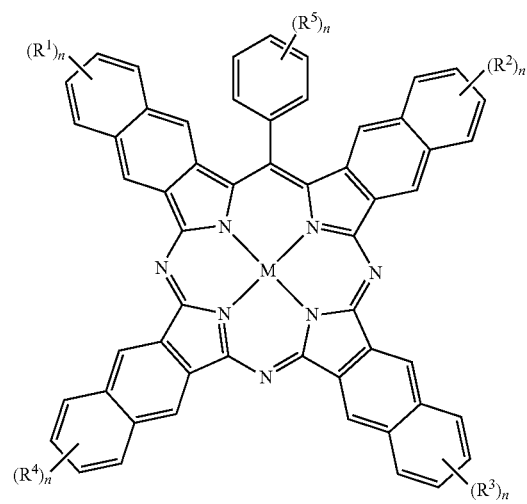

General Formula V wherein:

M represents $Pt^{2+}$, $Pd^{2+}$, $Zn^{2+}$, or $Mg^{2+}$;

each $R^1$, $R^2$, $R^3$, and $R^4$ independently represents hydrogen, deuterium, halide, nitro, nitrile, hydroxyl, thiol, methyl-$d_3$, phenyl-$d_5$, amino, or substituted or unsubstituted $C_1$-$C_4$ alkyl, alkoxy, aryl, or amino;

each $R^5$, $R^6$, $R^7$, and $R^8$, when present, independently represents hydrogen, deuterium, fluoride, nitrile, methyl-$d_3$, phenyl-$d_5$, or substituted or unsubstituted $C_1$-$C_4$ alkyl or aryl; and each n is independently an integer, valency permitting.

DETAILED DESCRIPTION

Figure 1:
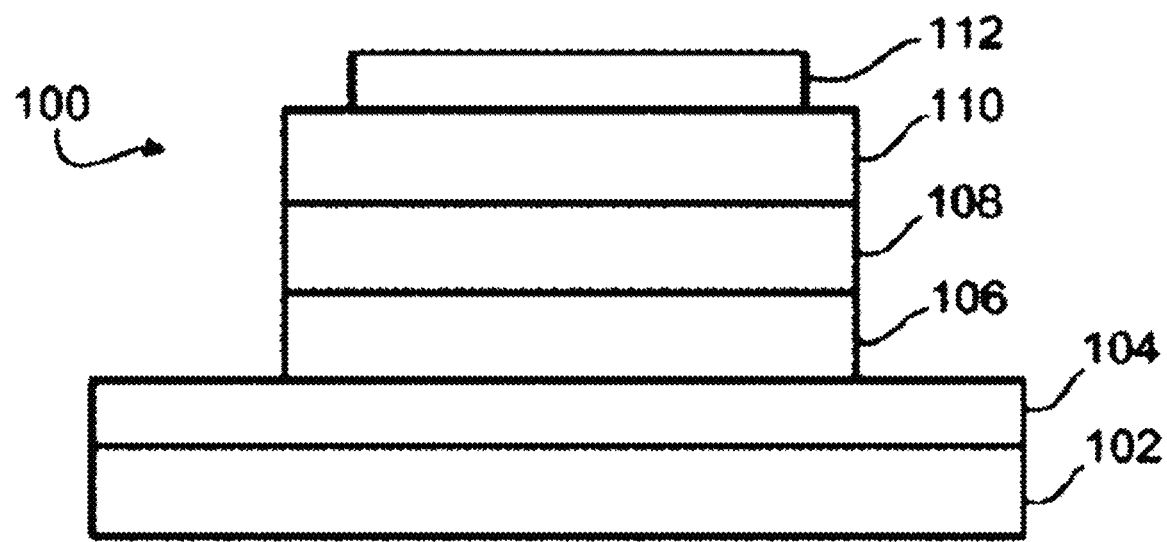
FIG. 1 depicts an organic light-emitting device (OLED).
Figure 2A:
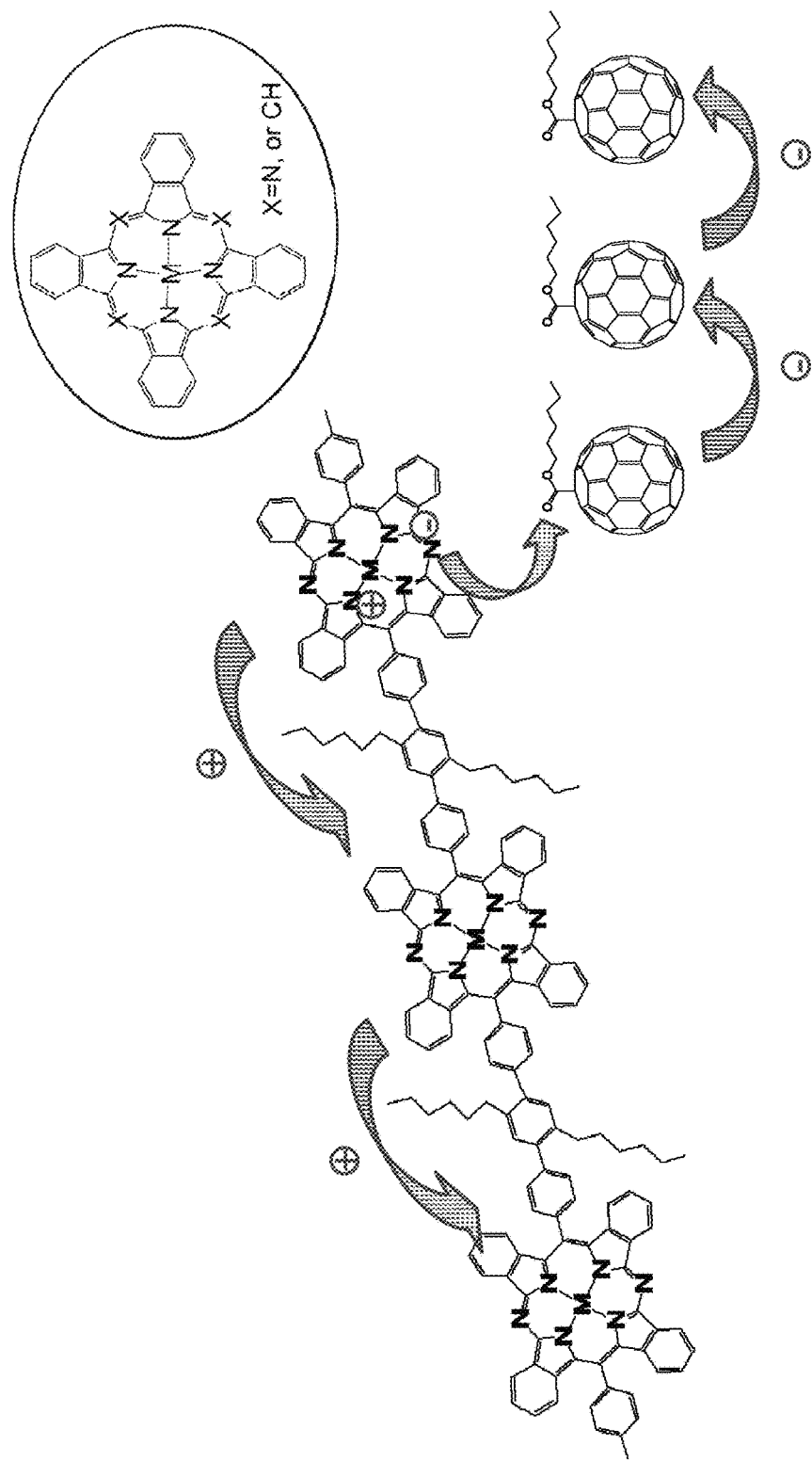
FIGS. 2A-2E show steps in a synthetic procedure.
Figure 2B:
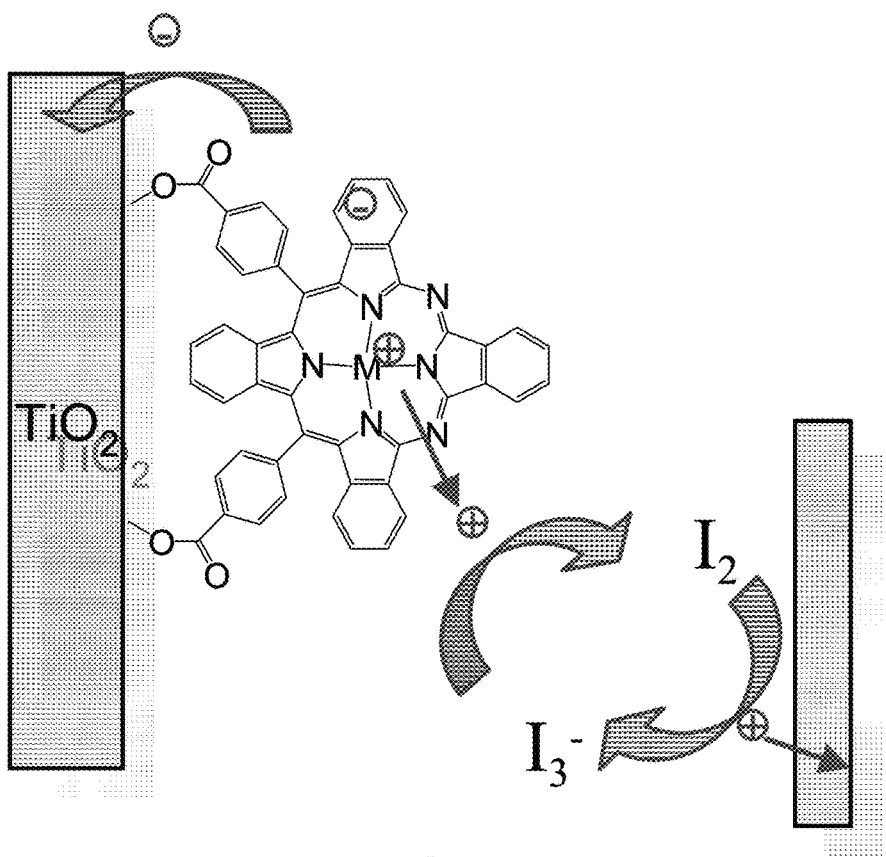
Figure 2C:
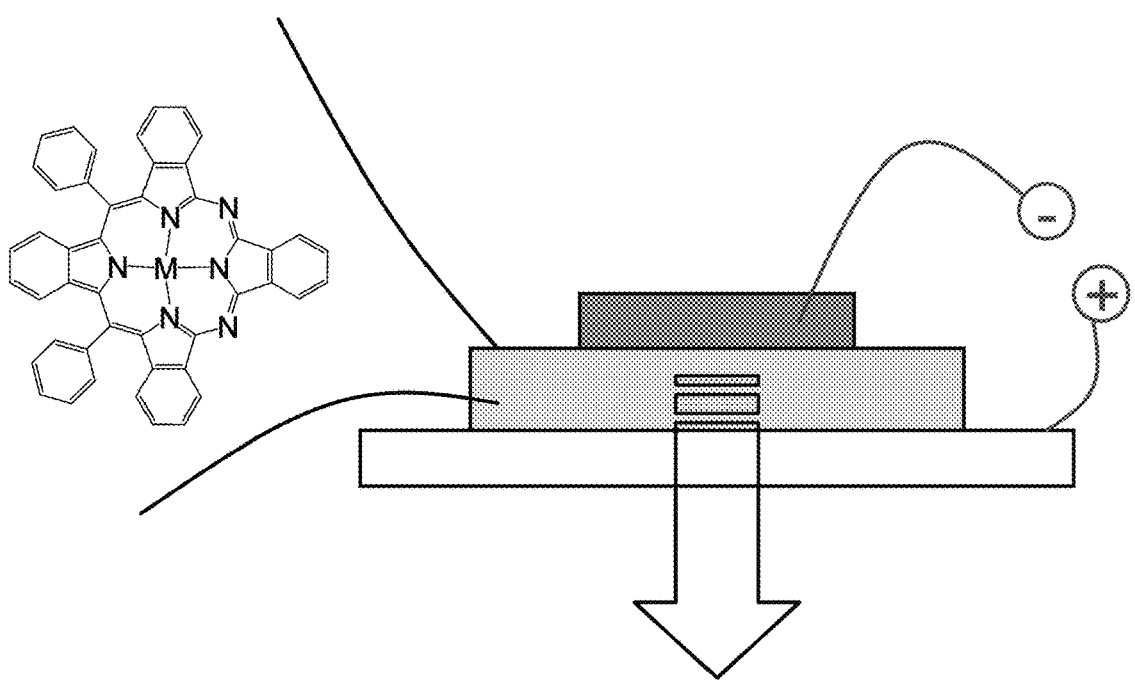
Figure 2D:
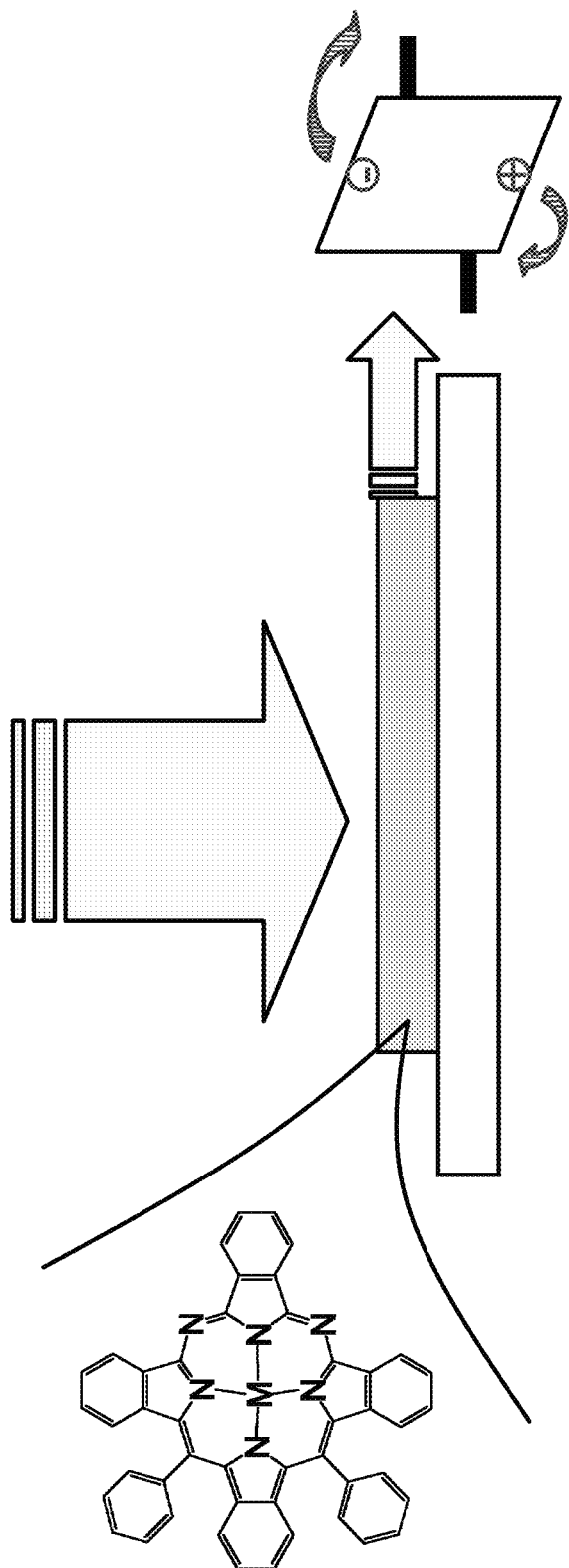
Figure 2E:
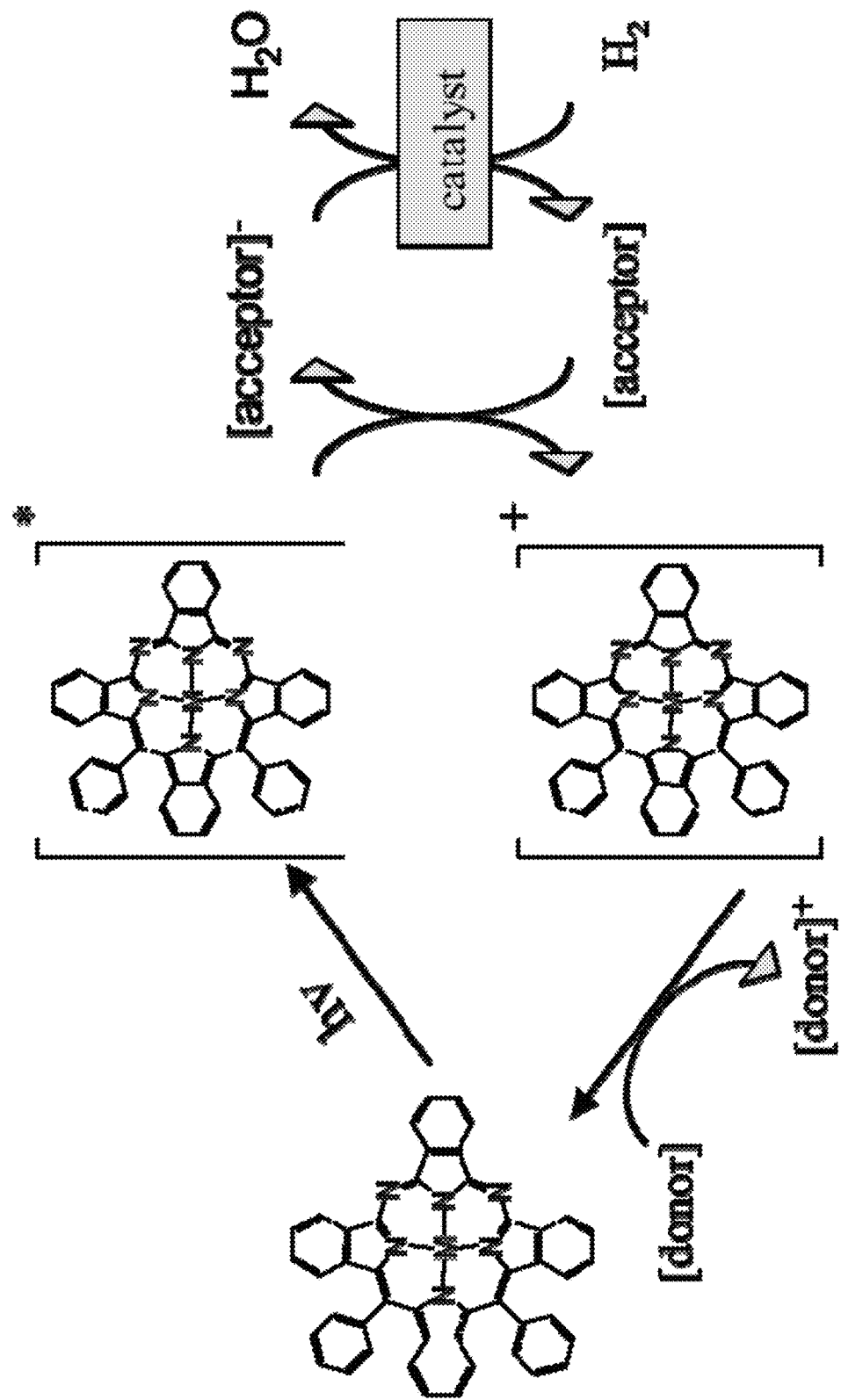

Porphyrin and azaporphyrin derivatives with fluorine functional groups or analogs demonstrate improved thermal and chemical stability and enhanced performance in optoelectronic applications. These complexes are suitable for use as donor-type materials for photovoltaic cells, absorbers for dye-sensitized solar cells, emitters for red and near infra-red organic light-emitting diodes (OLEDs), absorbers and re-emitters for organic concentrators (e.g., large area organic film for collection of sunlight for small-size and high efficiency inorganic photovoltaics, and absorbers for hydro-generation.

Definitions

It is to be understood that the figures and descriptions of the present invention have been simplified to illustrate elements that are relevant for a clear understanding of the present invention, while eliminating, for the purpose of clarity, many other elements found in the art related to organic light emitting devices and the like. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods, and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As referred to herein, a linking atom or a linking group can connect two groups such as, for example, an N and C group. The linking atom can optionally, if valency permits, have other chemical moieties attached. For example, in one aspect, an oxygen would not have any other chemical groups attached as the valency is satisfied once it is bonded to two groups (e.g., N and/or C groups). In another aspect, when carbon is the linking atom, two additional chemical moieties can be attached to the carbon. Suitable chemical moieties include, but are not limited to, hydrogen, hydroxyl, alkyl, alkoxy, =O, halogen, nitro, amine, amide, thiol, aryl, heteroaryl, cycloalkyl, and heterocyclyl.

The term "cyclic structure" or the like terms used herein refer to any cyclic chemical structure which includes, but is not limited to, aryl, heteroaryl, cycloalkyl, cycloalkenyl, and heterocyclyl.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. The notation "$C_n$alkyl" as used herein refers to an alkyl group having n carbon atoms. Thus, for example, the term "$C_1$-$C_4$ alkyl" as used herein refers to a branched or unbranched saturated hydrocarbon group of 1 to 4 carbon atoms, such as methyl, ethyl, n-propyl, isopropyl, n-butyl, isobutyl, s-butyl, and t-butyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as -$OA^1$ where $A^1$ is alkyl or cycloalkyl as defined above. "Alkoxy" also includes polymers of alkoxy groups as just described; that is, an alkoxy can be a polyether such as -$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bond, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula C(O)H. Throughout this specification "C(O)" is a short hand notation for a carbonyl group, i.e., C=O.

The terms "amine" or "amino" as used herein are represented by the formula -$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O), or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "heterocyclyl," as used herein refers to single and multi-cyclic non-aromatic ring systems and "heteroaryl" as used herein refers to single and multi-cyclic aromatic ring systems: in which at least one of the ring members is other than carbon. The term "heterocyclyl" includes azetidine, dioxane, furan, imidazole, isothiazole, isoxazole, morpholine, oxazole, oxazole, including, 1,2,3-oxadiazole, 1,2,5-oxadiazole and 1,3,4-oxadiazole, piperazine, piperidine, pyrazine, pyrazole, pyridazine, pyridine, pyrimidine, pyrrole, pyrrolidine, tetrahydrofuran, tetrahydropyran, tetrazine, including 1,2,4,5-tetrazine, tetrazole, including 1,2,3,4-tetrazole and 1,2,4,5-tetrazole, thiadiazole, including, 1,2,3-thiadiazole, 1,2,5-thiadiazole, and 1,3,4-thiadiazole, thiazole, thiophene, triazine, including 1,3,5-triazine and 1,2,4-triazine, triazole, including, 1,2,3-triazole, 1,3,4-triazole, and the like.

The term "halide" as used herein includes fluoride, chloride, bromide, and iodide.

The term "hydroxyl" as used herein is represented by the formula OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —N$_3$.

The term "nitro" as used herein is represented by the formula —NO$_2$.

The term "nitrile" as used herein is represented by the formula —CN.

The term "thiol" as used herein is represented by the formula —SH.

The term "ureido" as used herein refers to a urea group of the formula —NHC(O)NH$_2$ or —NHC(O)NH—.

The term "phosphoramide" as used herein refers to a group of the formula —P(O)(NA$^1$A$^2$)$_2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "carbamoyl" as used herein refers to an amide group of the formula CONA$^1$A$^2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "sulfamoyl" as used herein refers to a group of the formula S(O)$_2$NA$^1$A$^2$, where A$^1$ and A$^2$ can be, independently, hydrogen or an alkyl, cycloalkyl, alkoxy, alkenyl, cycloalkenyl, alkynyl, cycloalkynyl, aryl, or heteroaryl group as described herein.

The term "silyl" as used herein is represented by the formula SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ is hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ is hydrogen or an alkyl, cycloalkyl, alkenyl, cycloalkenyl, alkynyl, cycloalkynyl, aryl, or heteroaryl group as described herein. The term "sulfone" as used herein is represented by the formula A$^1$S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A$^1$S(O)A$^2$, where Aland A$^2$ can be, independently, an alkyl, cycloalkyl, alkenyl, cycloalkenyl, alkynyl, cycloalkynyl, aryl, or heteroaryl group as described herein.

Contemplated herein, any occurrence of hydrogen (H), or any unsubstituted position, can independently be replaced with deuterium (D). The notation "-d$_n$" represents a group in which n of the hydrogens are replaced with deuterium. For example, methyl-d$_3$ represents a methyl group having three deuterium atoms bound thereto.

"R," "R$^1$," "R$^2$," "R$^3$," "R$^n$," where n is an integer, as used herein can, independently, include hydrogen or one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within a second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. It is also contemplated that, in certain aspects, unless expressly indicated to the contrary, individual substituents can be further optionally substituted (i.e., further substituted or unsubstituted).

In some aspects, a structure of a compound can be represented by a formula:

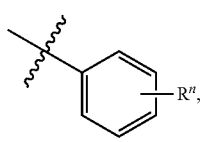

which is understood to be equivalent to a formula:

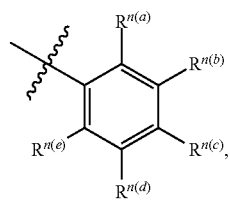

wherein n is typically an integer. That is, $R^n$ is understood to represent up to five independent non-hydrogen substituents, $R^{n(a)}$, $R^{n(b)}$, $R^{n(c)}$, $R^{(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Several references to $R^1$, $R^2$, $R^3$, $R^4$, $R^5$, $R^6$, etc. are made in chemical structures and moieties disclosed and described herein. Any description of $R^1$, $R^2$, $R^3$, $R^4$, $R^5$, $R^6$, etc. in the specification is applicable to any structure or moiety reciting $R^1$, $R^2$, $R^3$, $R^4$, $R^5$, $R^6$, etc. respectively.

In defining various terms, "$R^1$", "$R^2$", "$R^3$", "$R^4$", etc. are used herein as generic symbols to represent various specific substituents. These symbols can be any substituent, not limited to those disclosed herein, and when they are defined to be certain substituents in one instance, they can, in another instance, be defined as some other substituents.

Compounds of the Invention

In one aspect, the present invention relates to fluorinated porphyrins and porphyrin derivatives shown in General Formulas I-V.

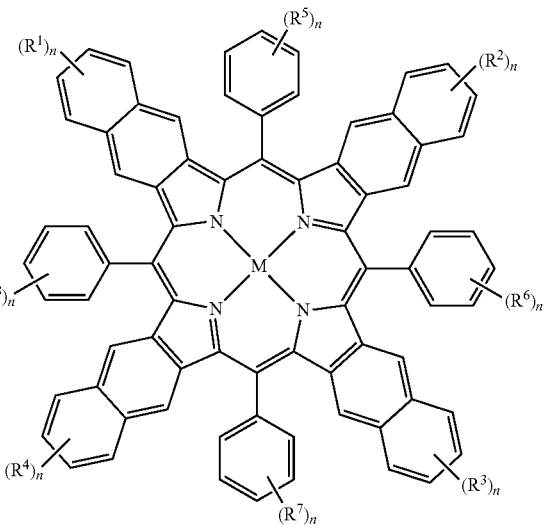

General Formula I

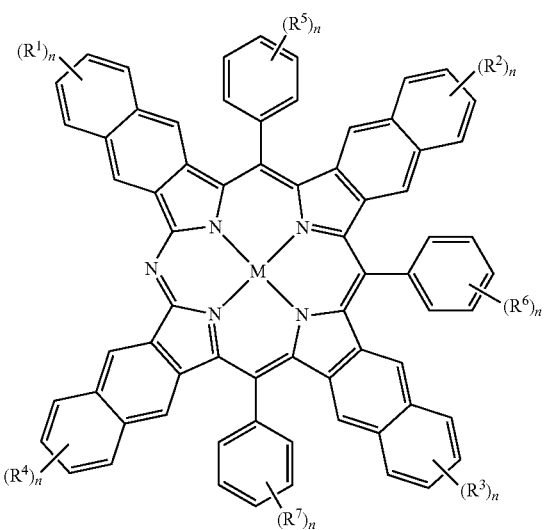

General Formula II

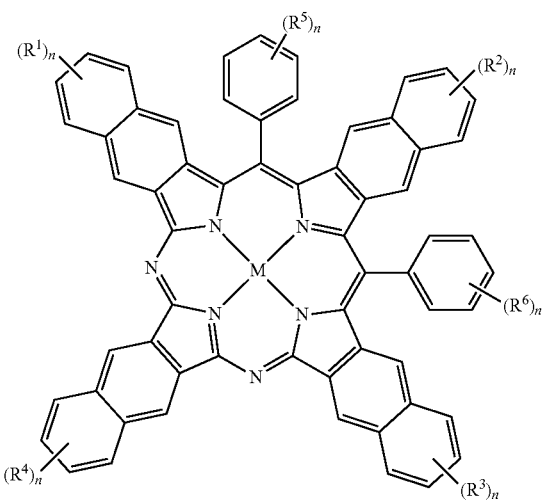

General Formula III

-continued

General Formula IV

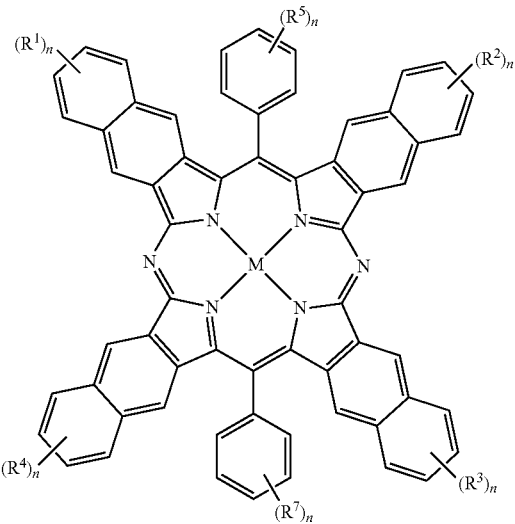

General Formula V

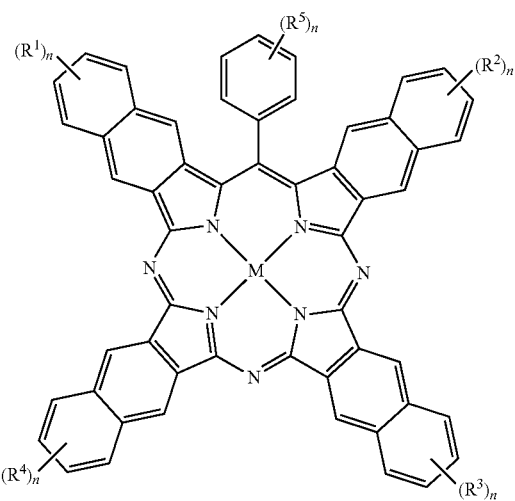

wherein:

M represents $Pt^{2+}$, $Pd^{2+}$, $Zn^{2+}$, or $Mg^{2+}$;

each $R^1$, $R^2$, $R^3$, and $R^4$ independently represents hydrogen, deuterium, halide, nitro, nitrile, hydroxyl, thiol, methyl-$d_3$, phenyl-$d_5$, amino, or substituted or unsubstituted $C_1$-$C_4$ alkyl, alkoxy, aryl, or amino;

each $R^5$, $R^6$, $R^7$, and $R^8$, when present, independently represents hydrogen, deuterium, fluoride, nitrile, methyl-$d_3$, phenyl-$d_5$, or substituted or unsubstituted $C_1$-$C_4$ alkyl or aryl; and each n is independently an integer, valency permitting.

As depicted, n is typically 4 or 5. Thus, $(R^x)_n$ refers to $R^{xa}$, $R^{xb}$, $R^{xc}$, and $R^{xd}$, where x is 1 to 4, n=4, and each of $R^{xa}$, $R^{xb}$, $R^{xc}$, and $R^{xd}$ independently represents hydrogen, deuterium, halide (e.g., fluoride), nitro, nitrile, hydroxyl, thiol, methyl-$d_3$, phenyl-$d_5$, amino, or substituted or unsubstituted $C_1$-$C_4$ alkyl, alkoxy, aryl, or amino. Similarly, $(R^y)_n$ refers to $R^{ya}$, $R^{yb}$, $R^{yc}$, $R^{yd}$, and $R^{ye}$, where y is 5 to 8, n=5, and each of $R^{5a}$, $R^{5b}$, $R^{5c}$, $R^{5d}$, and $R^{5e}$ independently represents hydrogen, deuterium, fluoride, nitrile, methyl-$d_3$, phenyl-$d_5$, or substituted or unsubstituted $C_1$-$C_4$ alkyl or aryl.

In some embodiments, each occurrence of $R^5$, $R^6$, $R^7$, and $R^8$, when present, independently represents hydrogen, deuterium, fluoride, chloride, methyl, methyl-$d_3$, t-butyl, $CF_3$, or nitrile.

Examples of complexes of General Formulas I-V are provided below. These examples are shown with M=$Pt^{2+}$ for convenience. However, this disclosure covers counterpart examples with M=$Pd^{2+}$, $Zn^{2+}$, or $Mg^{2+}$.

Examples of complexes of General Formula I are shown below.

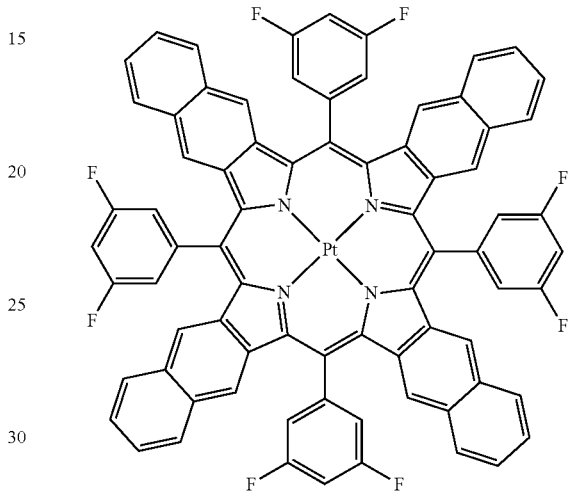

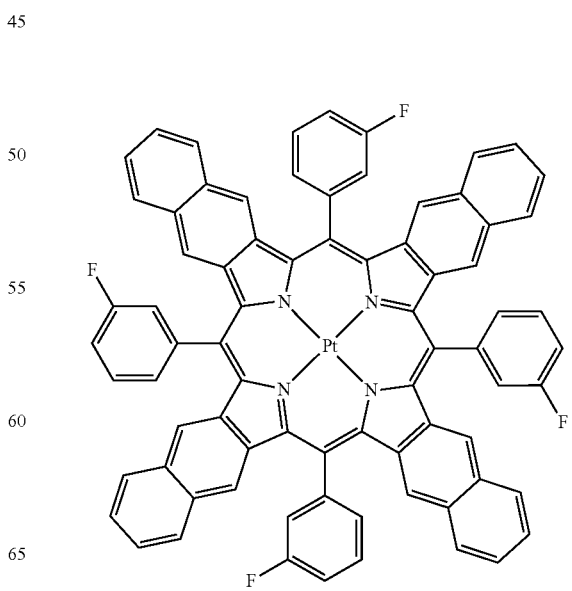

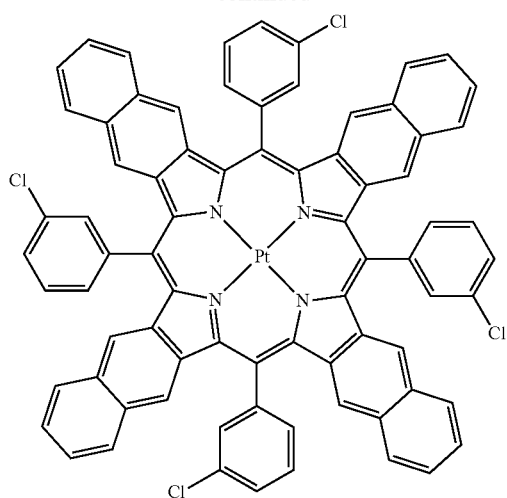
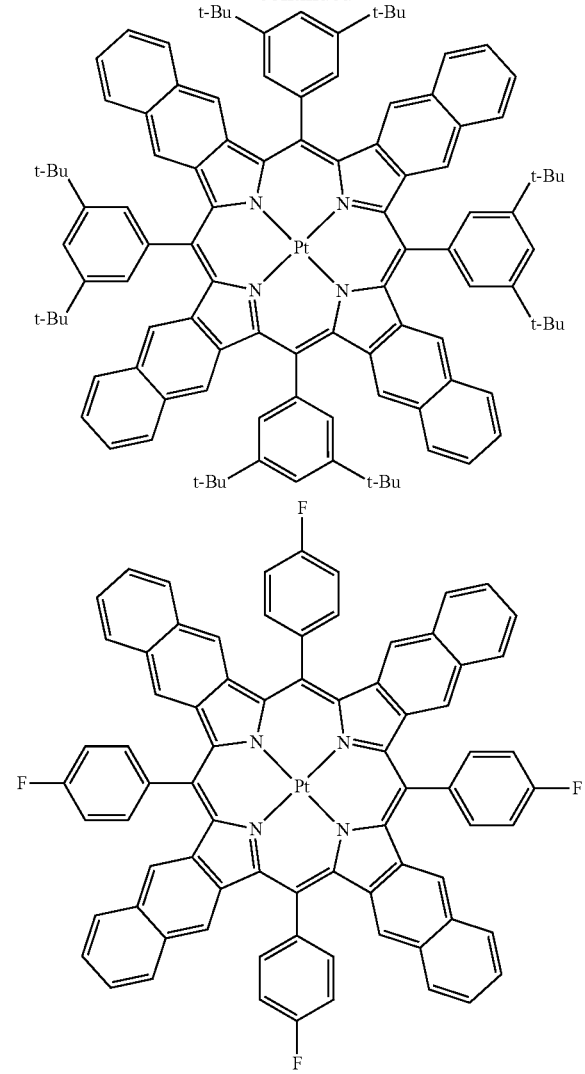
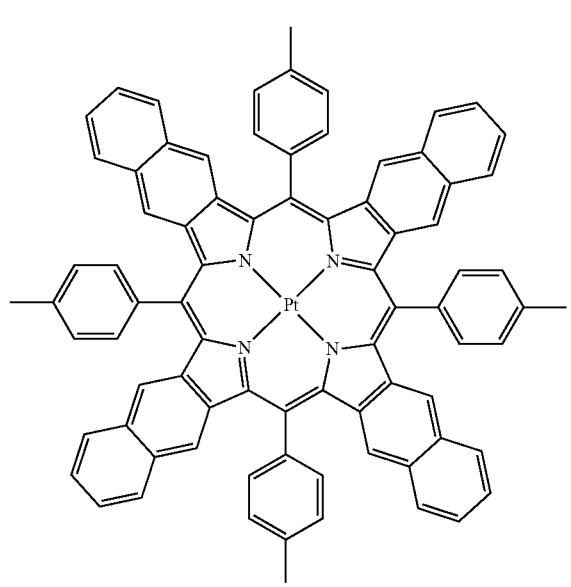
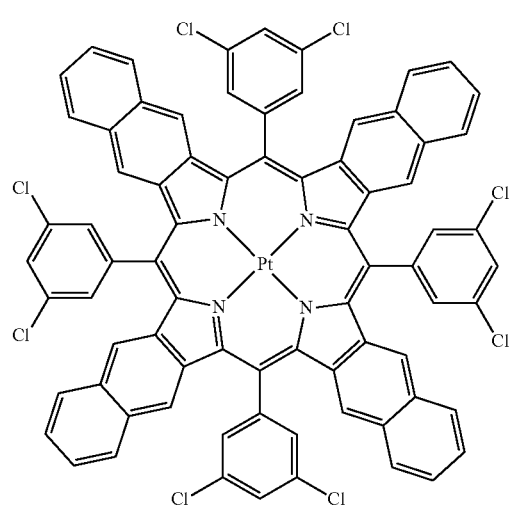

-continued
17
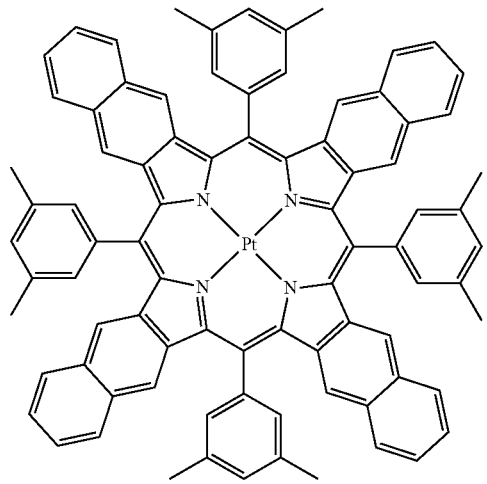
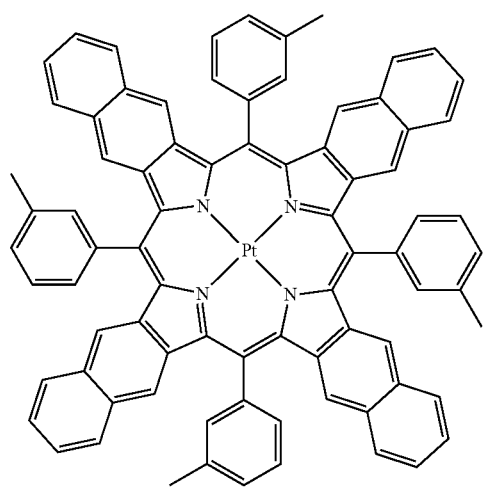
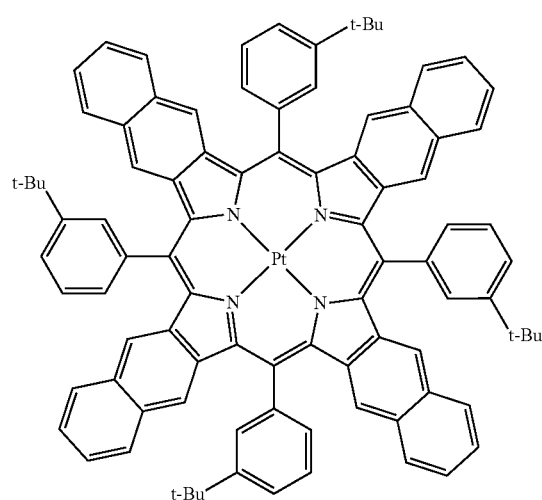
-continued
18
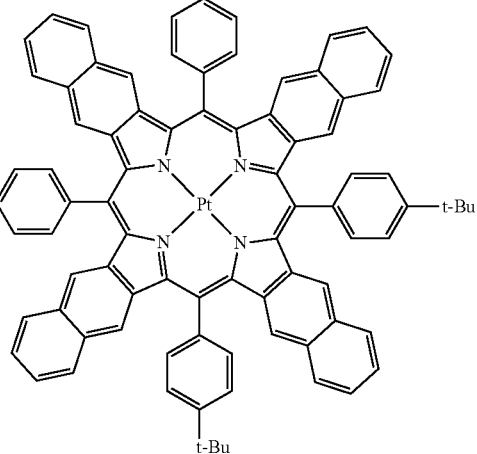
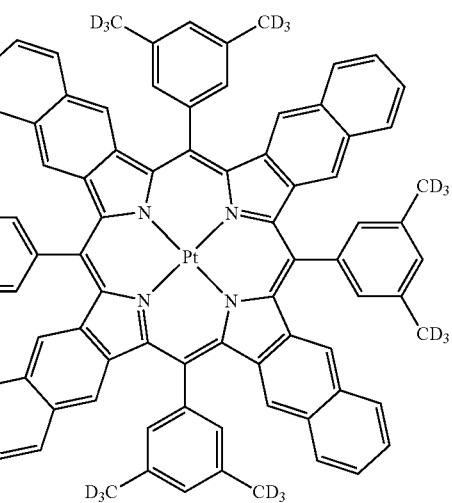
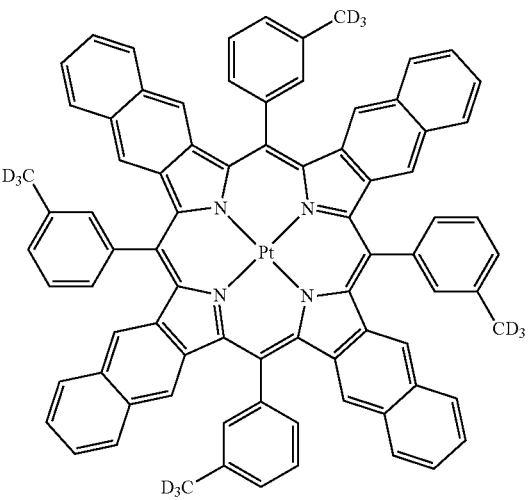

-continued
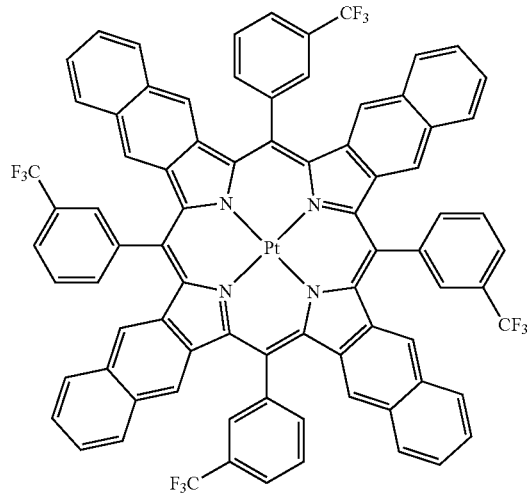
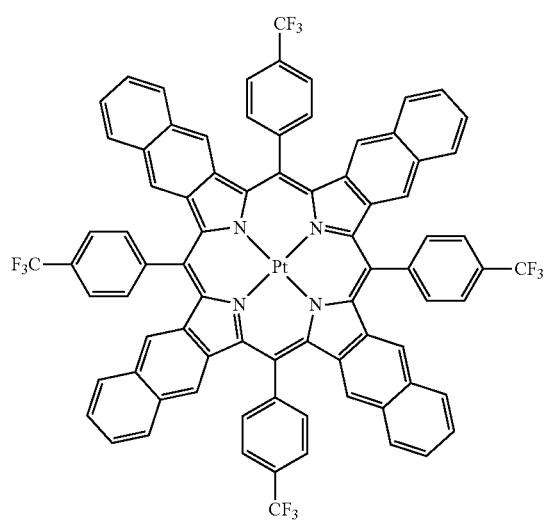
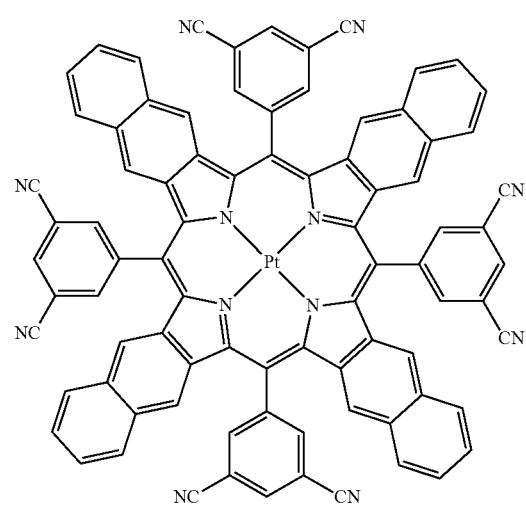
-continued
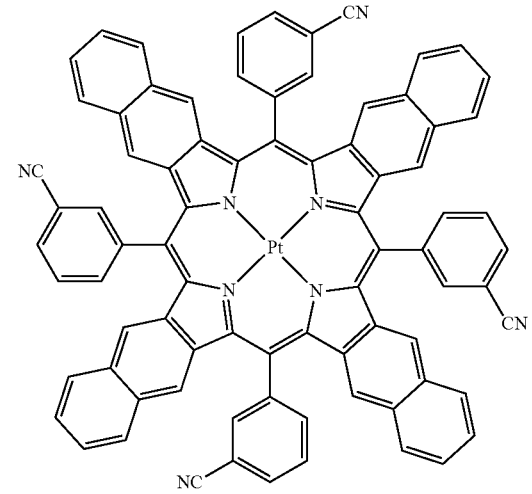
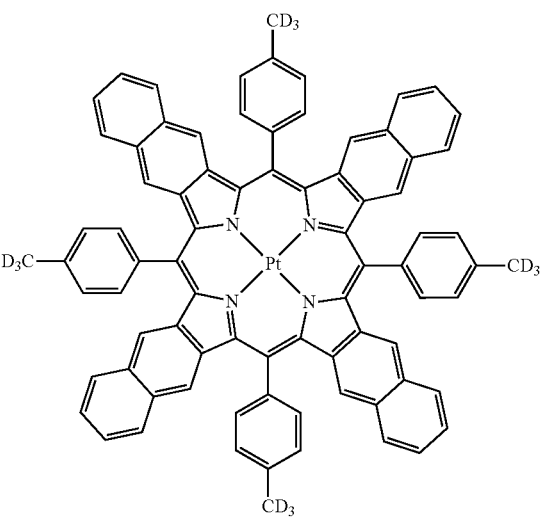
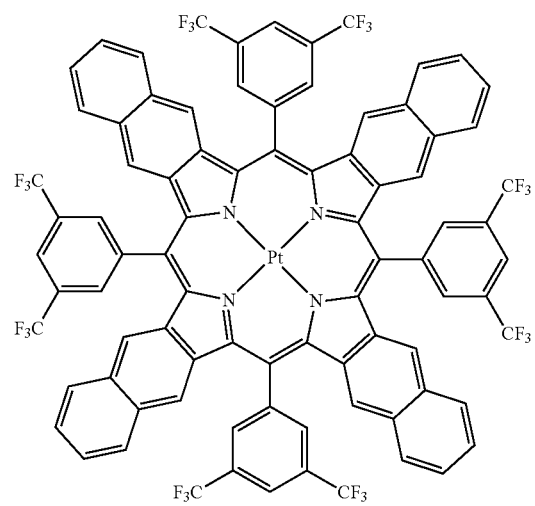

-continued
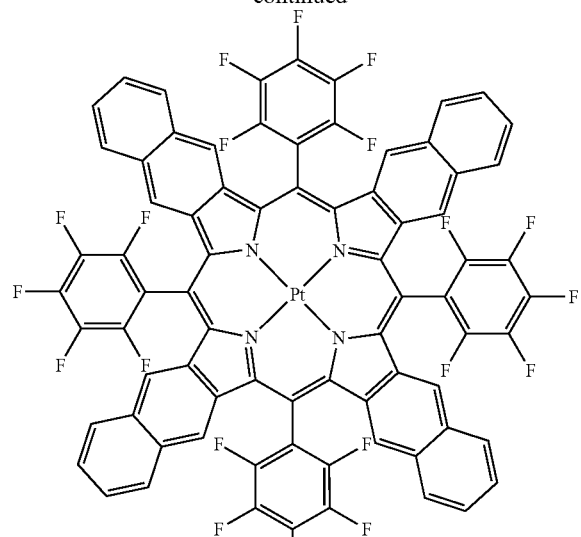
Examples of complexes of General Formula II are shown below.
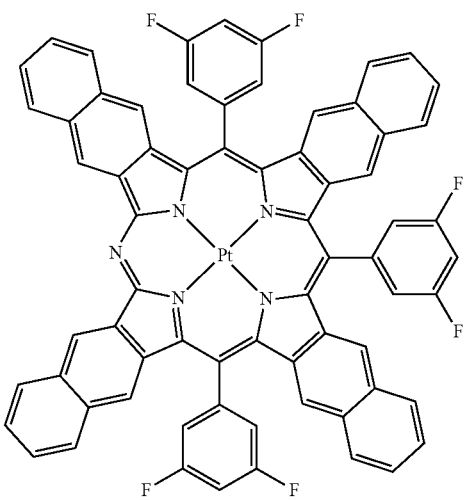
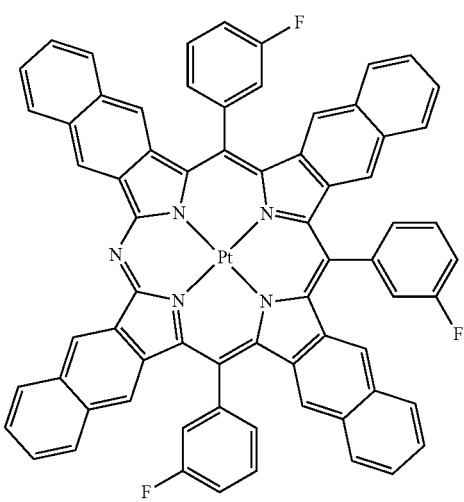
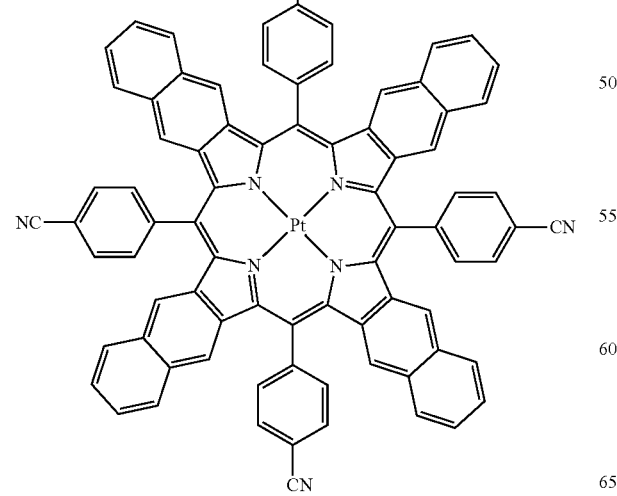
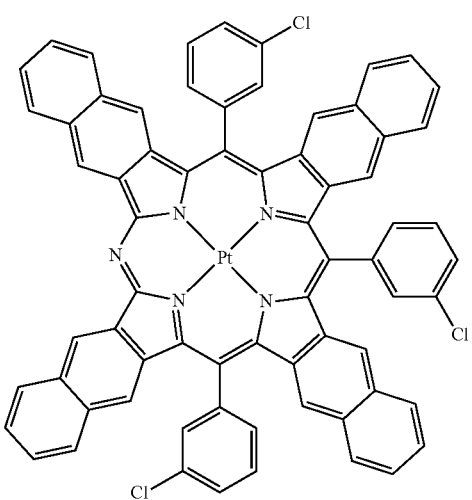

-continued
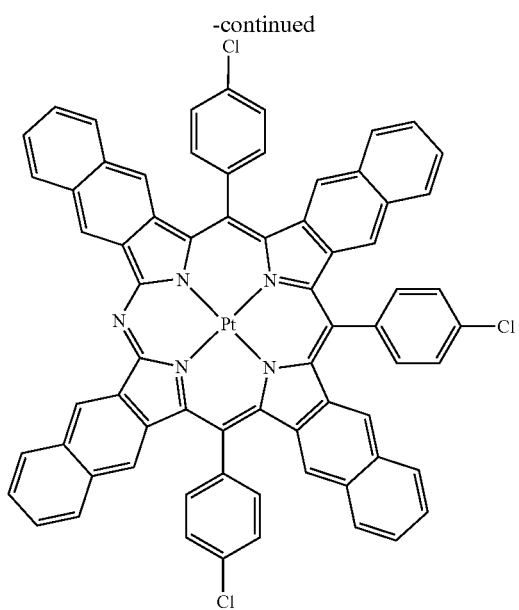
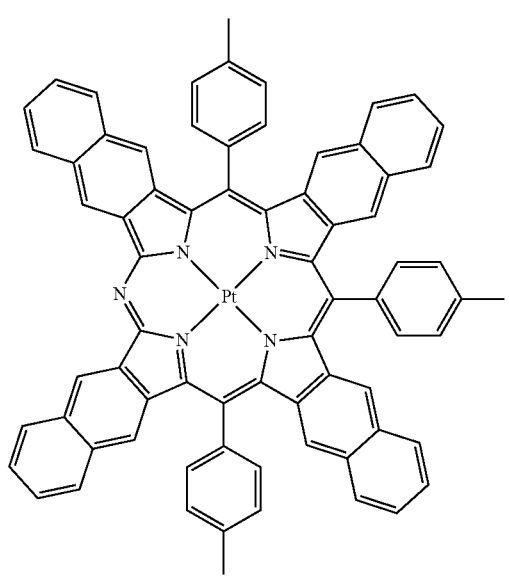
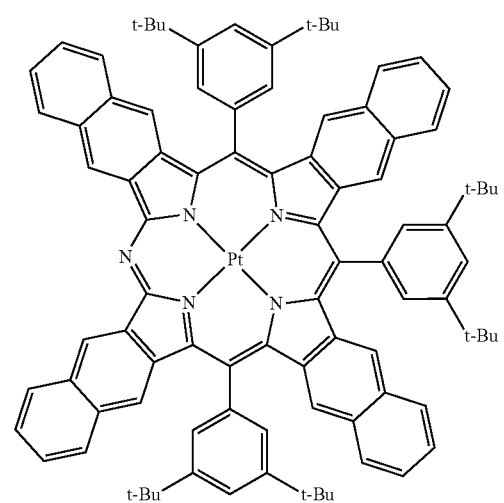
-continued
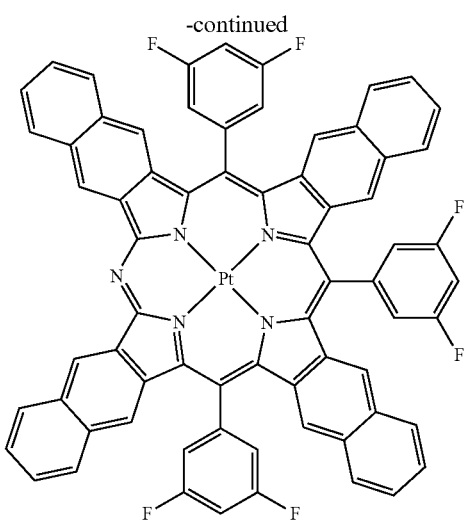
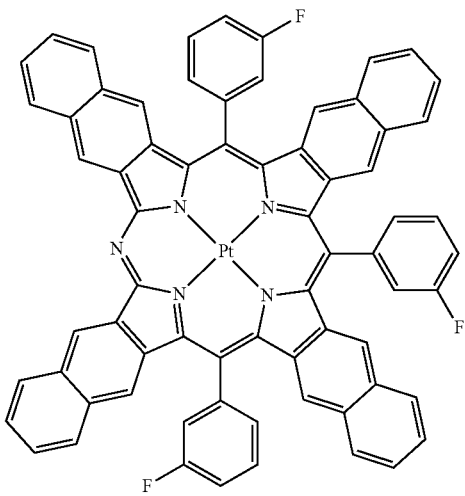
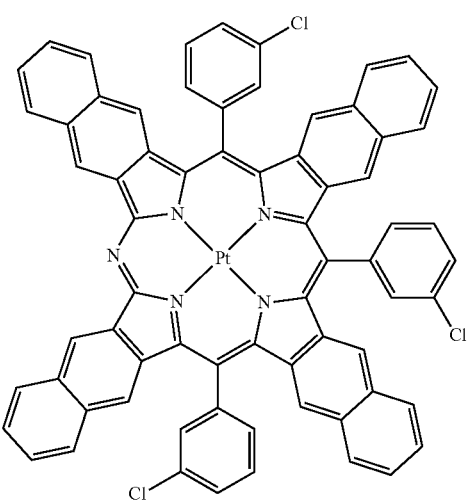

-continued
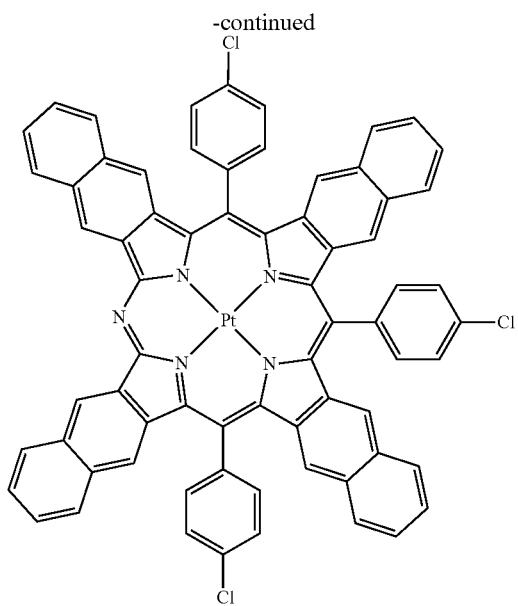
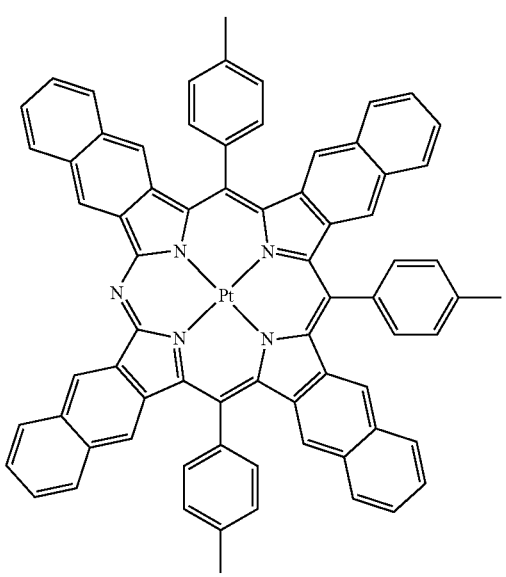
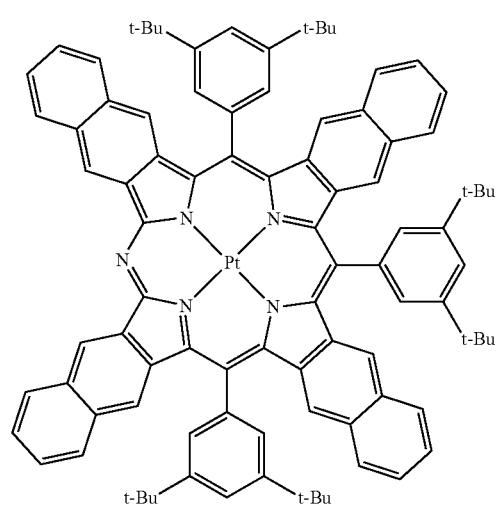
-continued
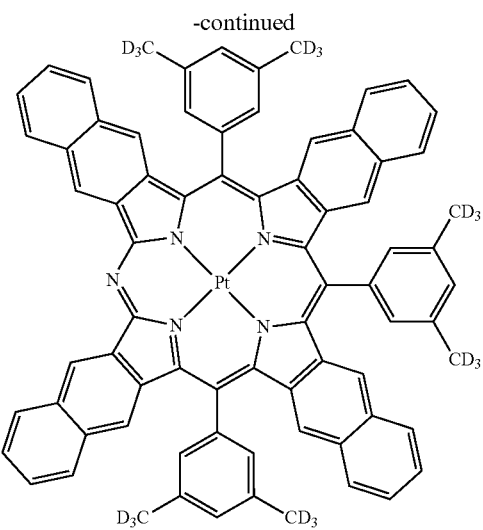
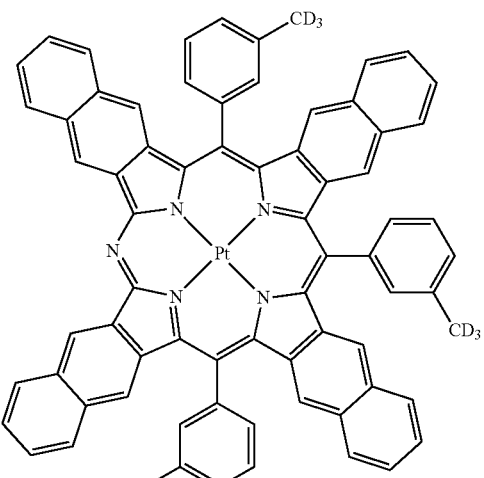
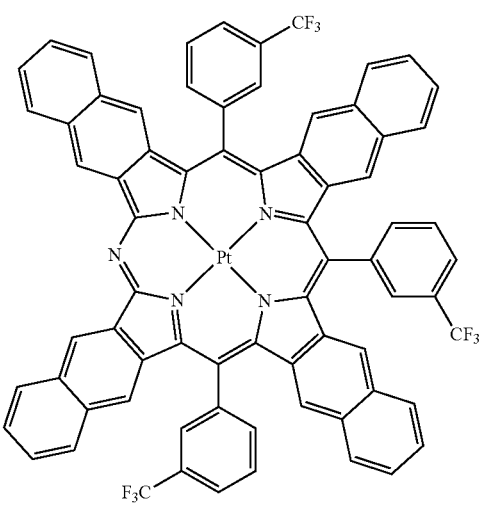

-continued
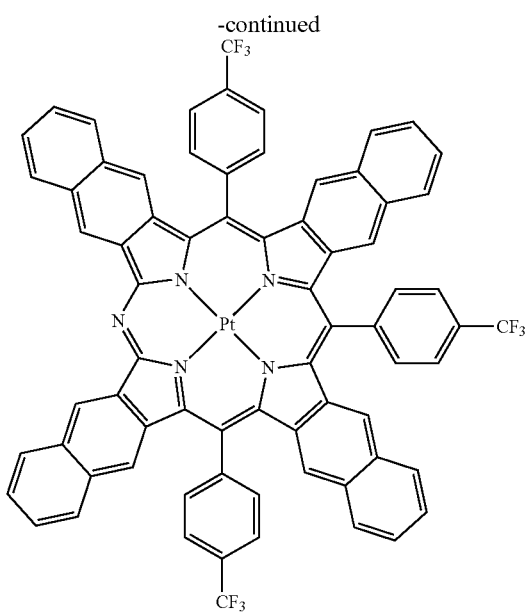
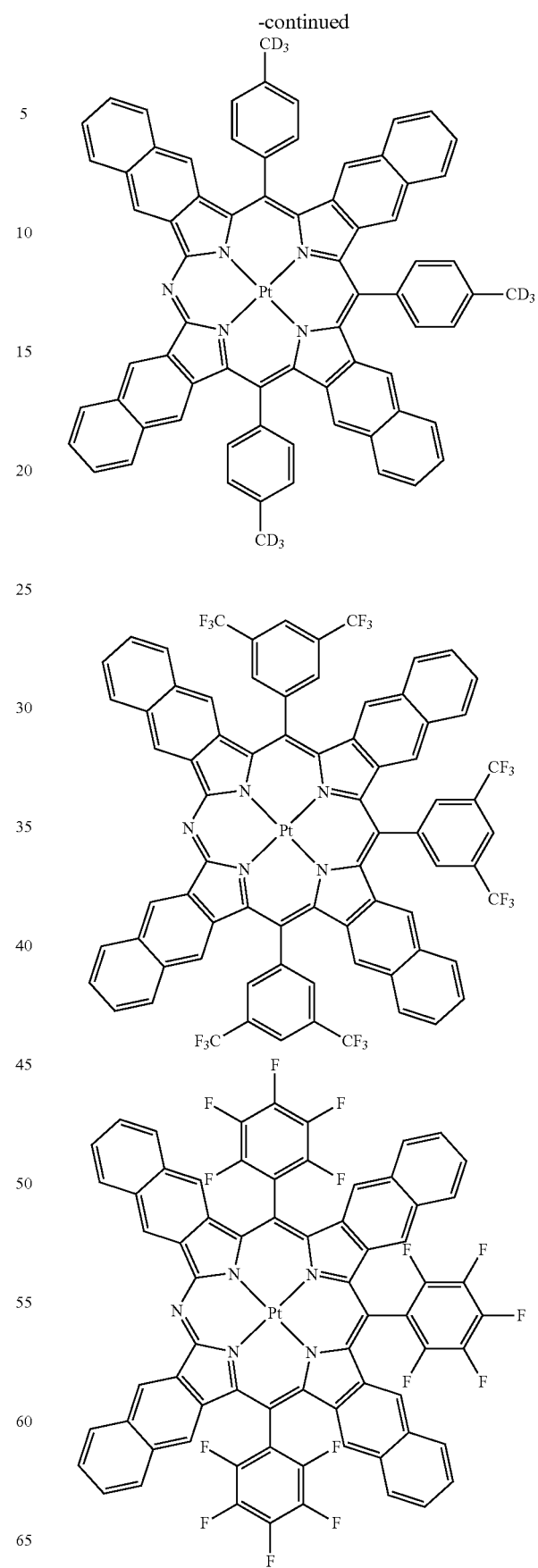

-continued
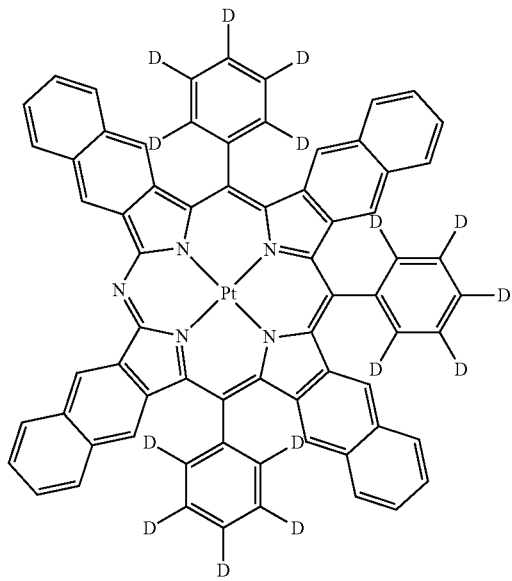
Examples of complexes of General Formula III are shown below.
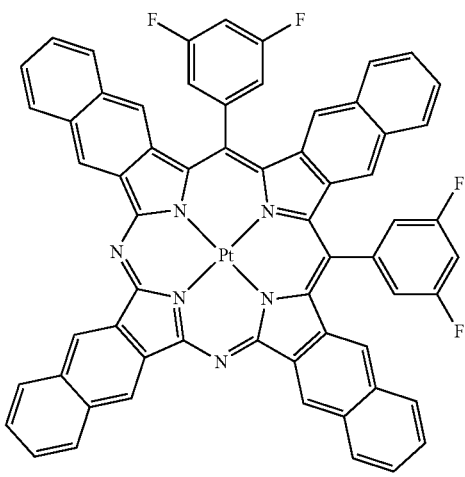
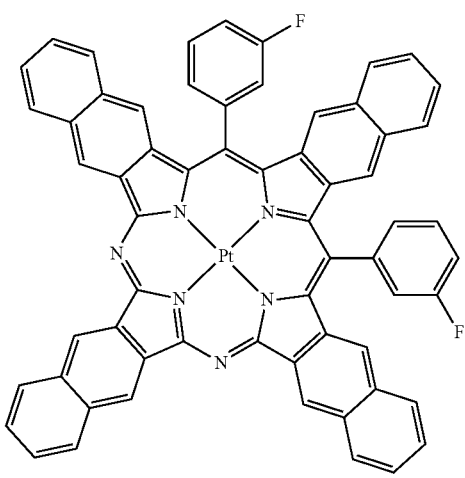
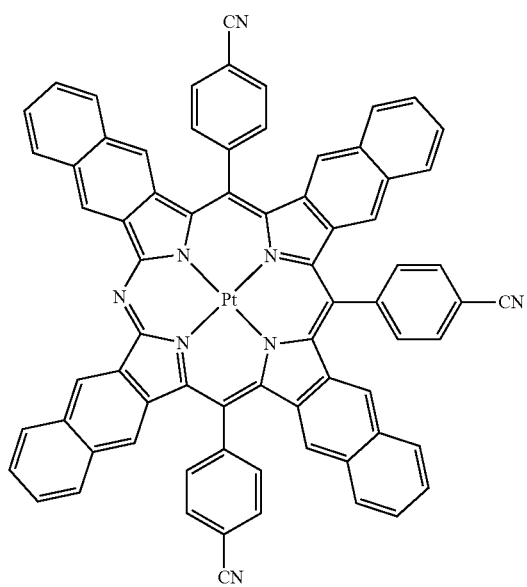
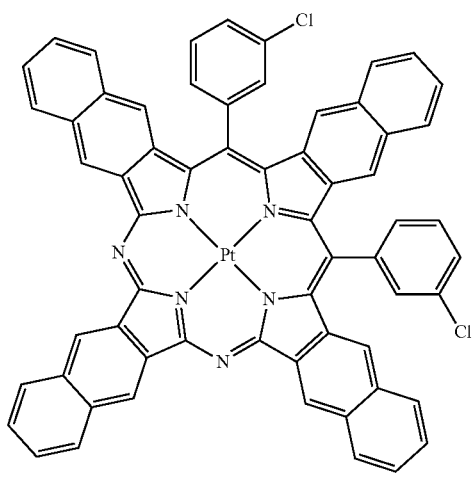

31
-continued
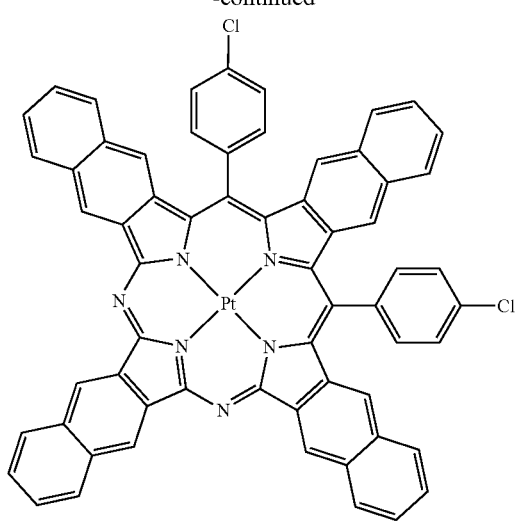
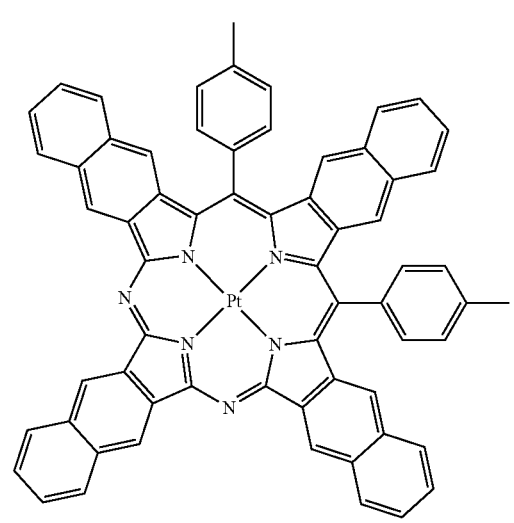
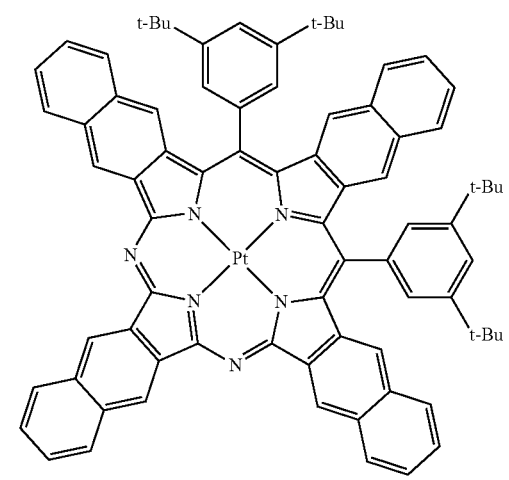
32
-continued
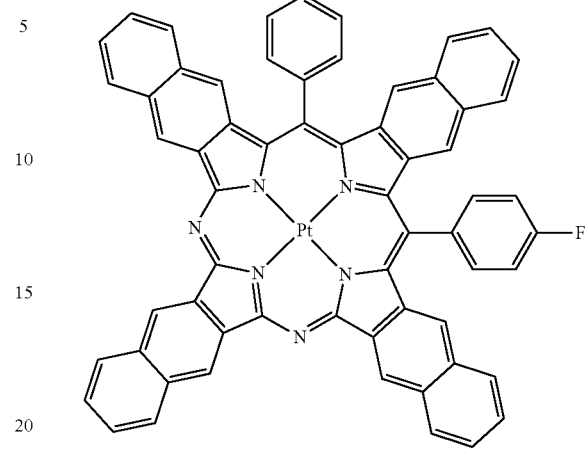
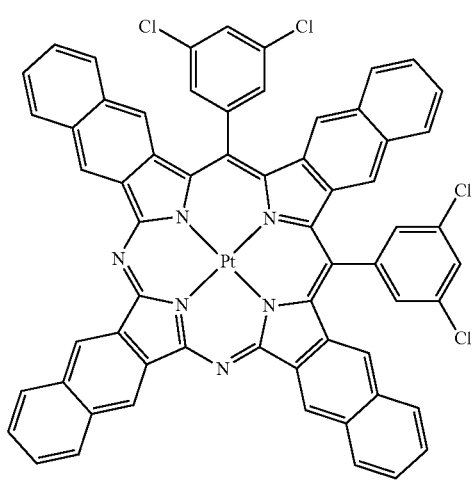
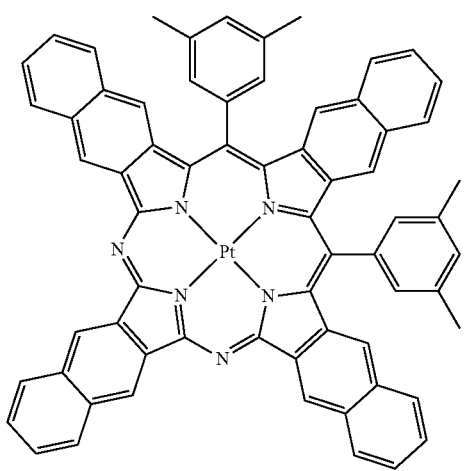

33
-continued
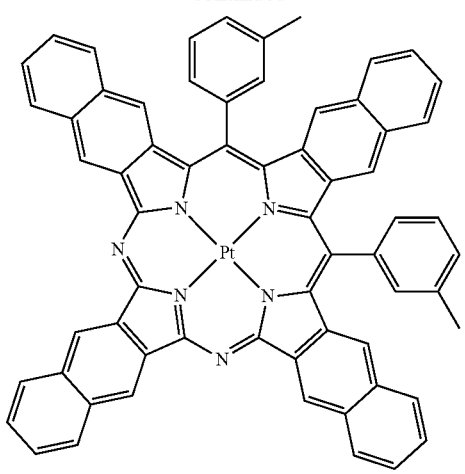
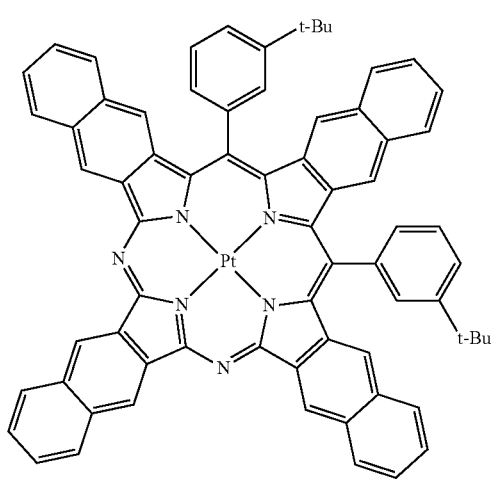
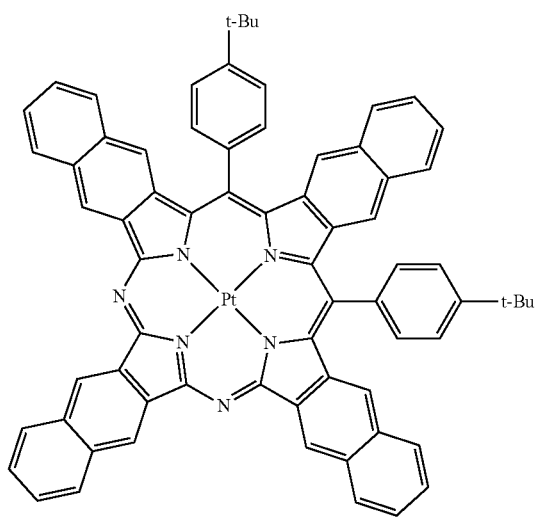
34
-continued
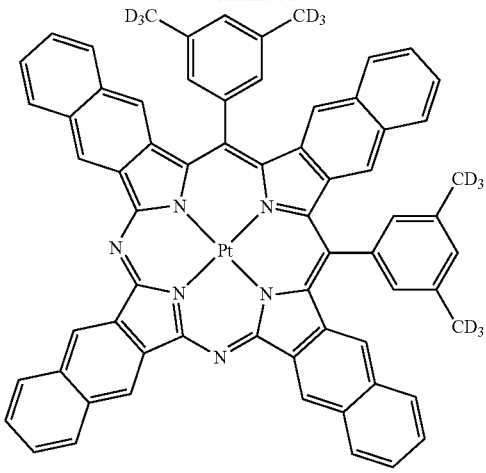
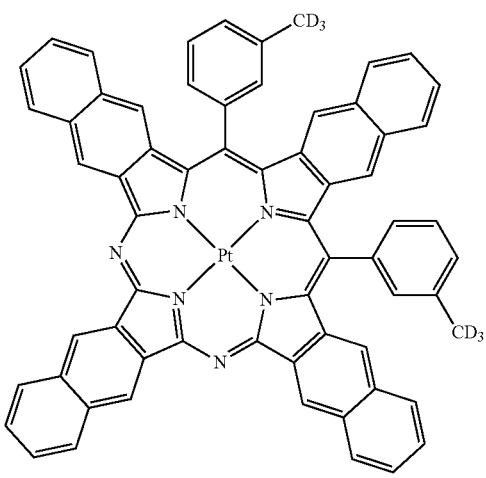
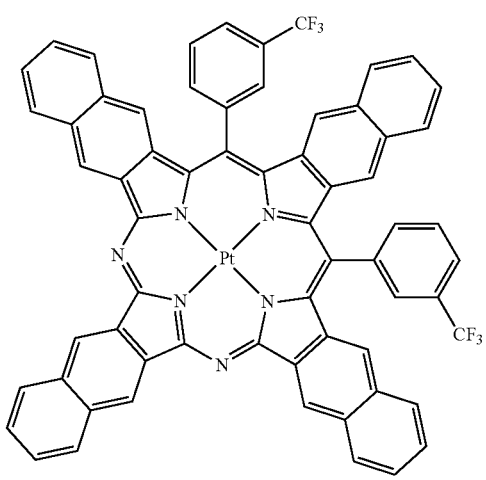

-continued
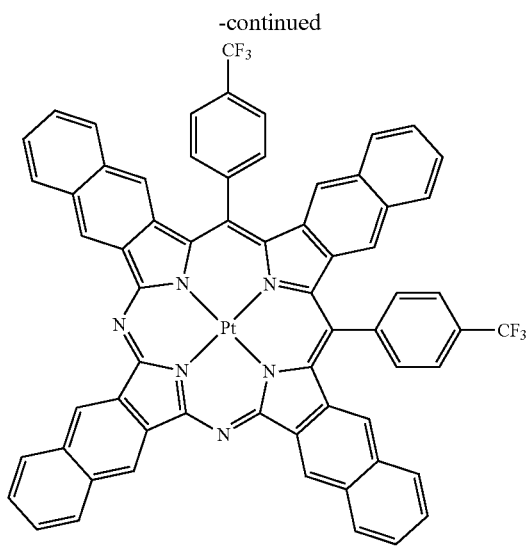
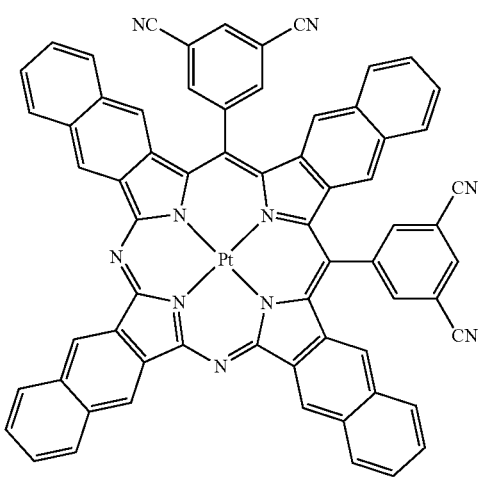
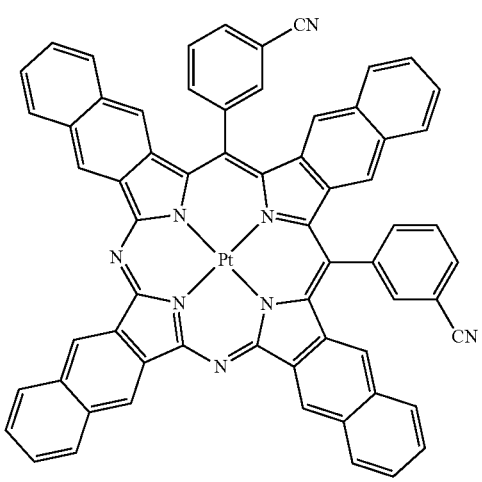
-continued
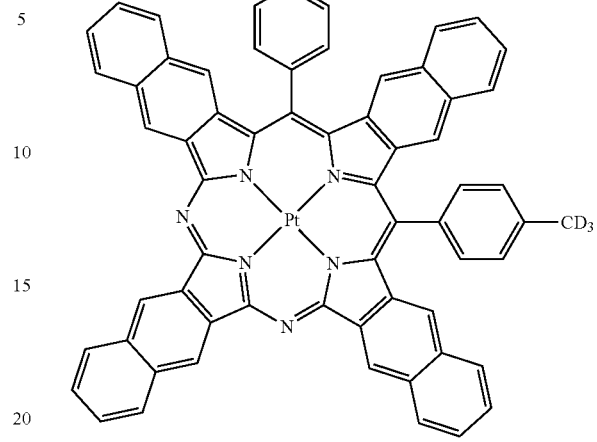
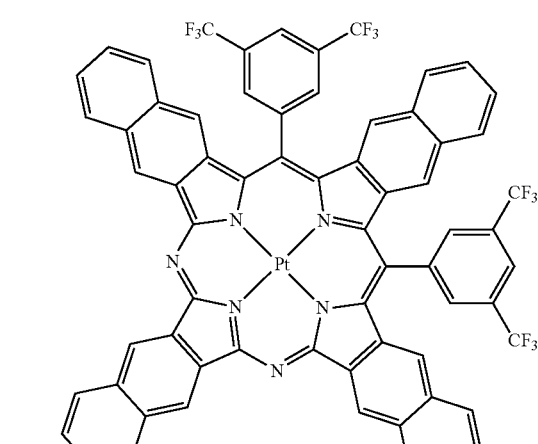
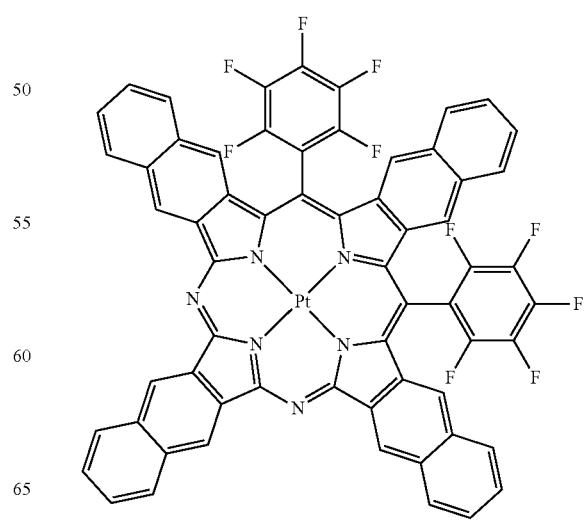

37
-continued
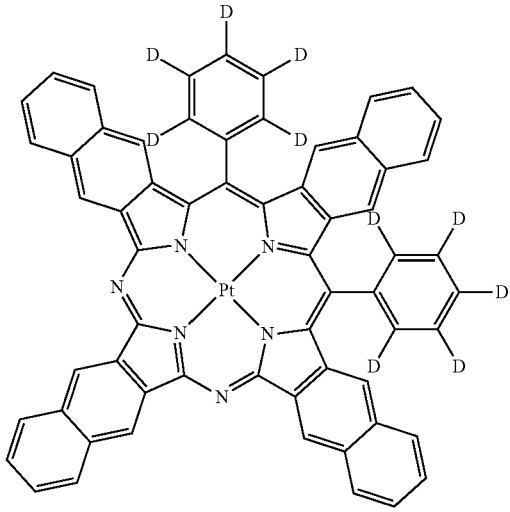
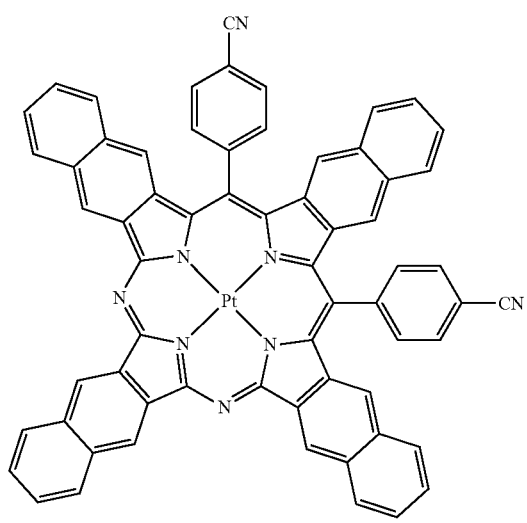
Examples of complexes of General Formula IV are shown below.
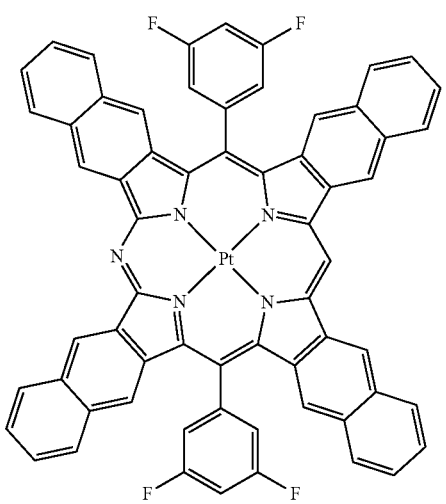
38
-continued
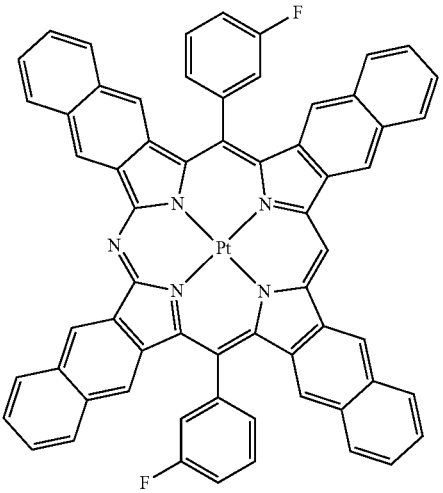
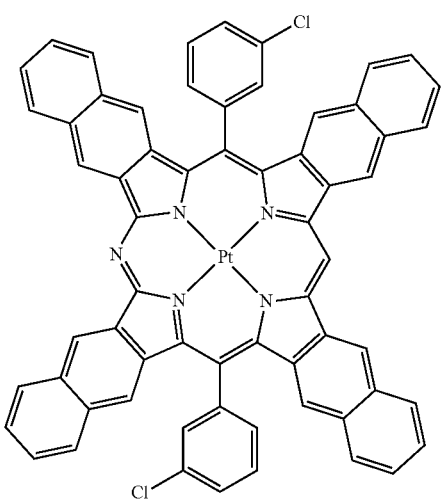
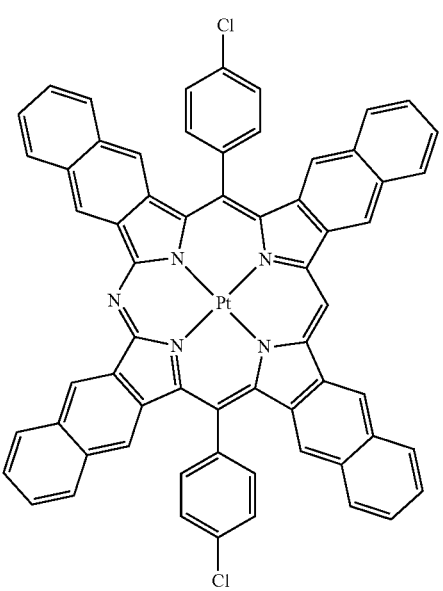

39
-continued
40
-continued
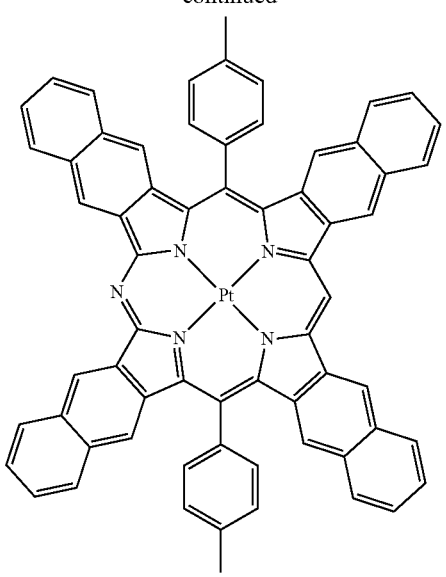
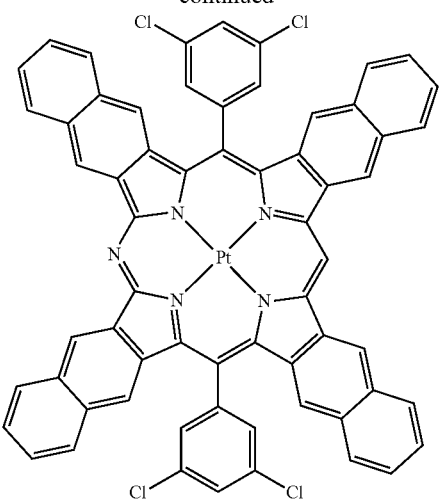
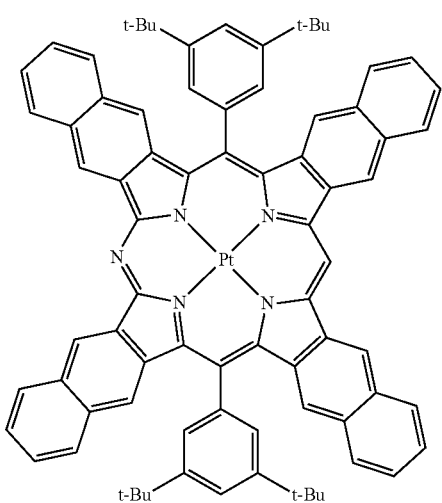
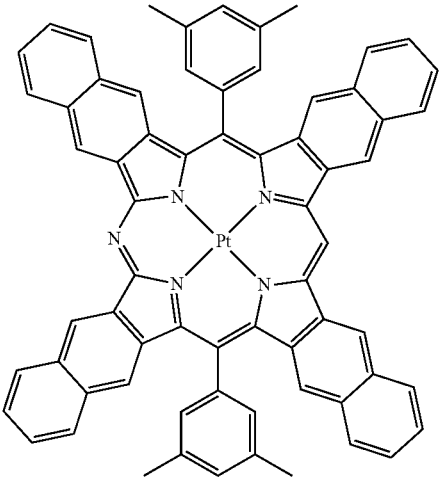
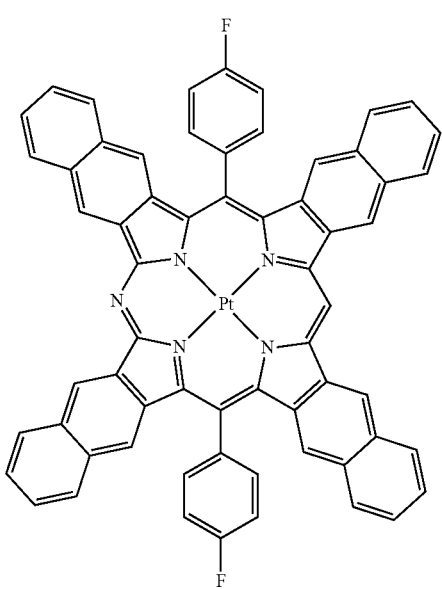
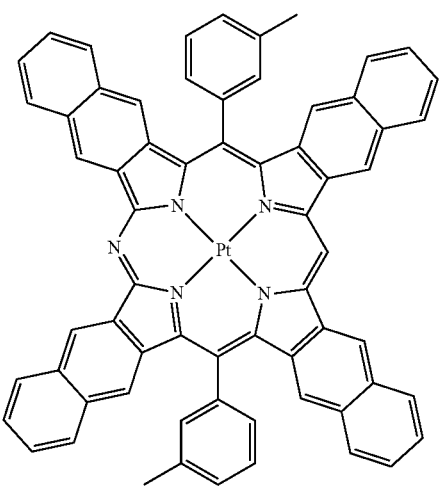

-continued
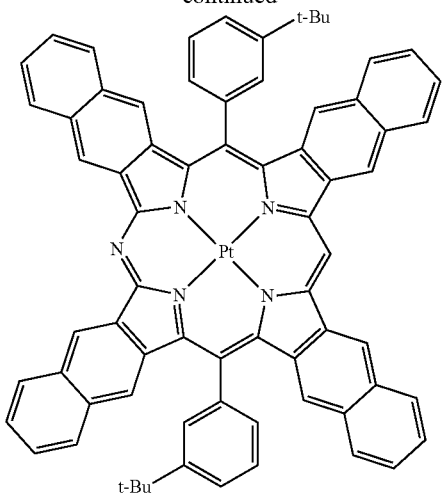
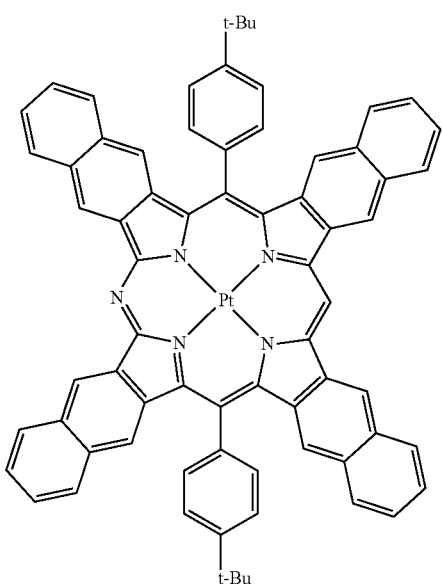
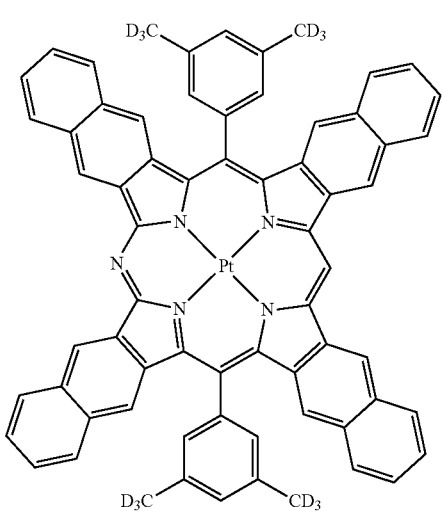
-continued
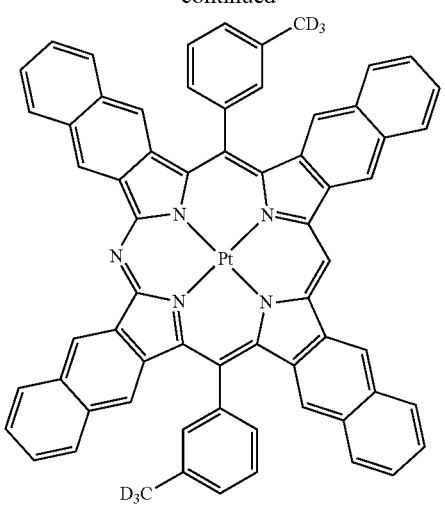
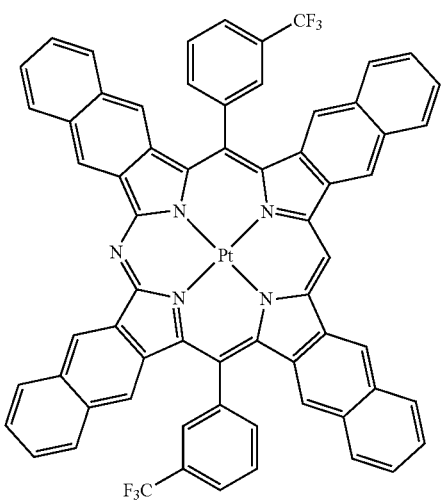
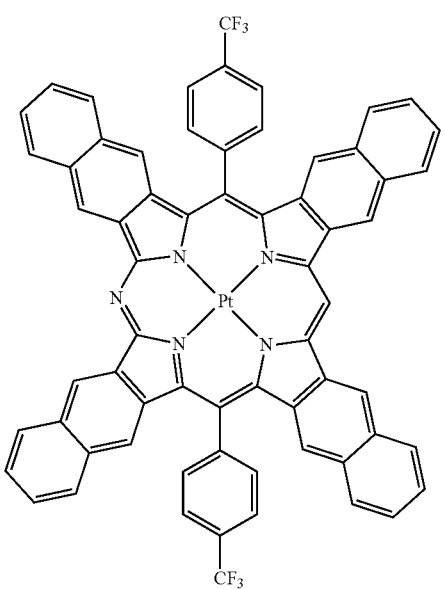

-continued
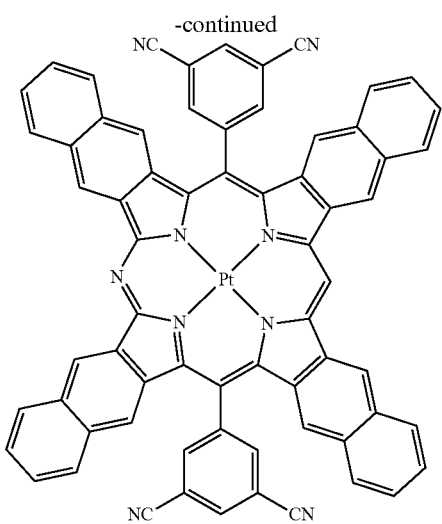
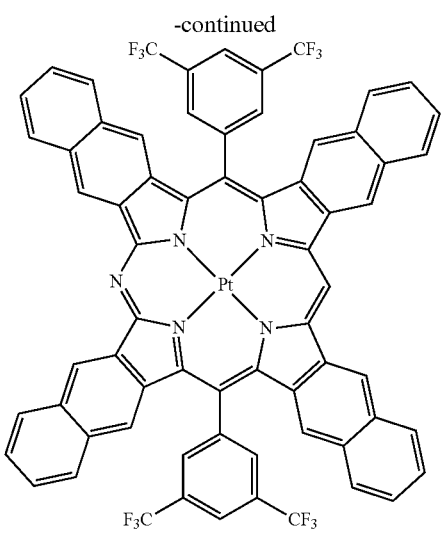
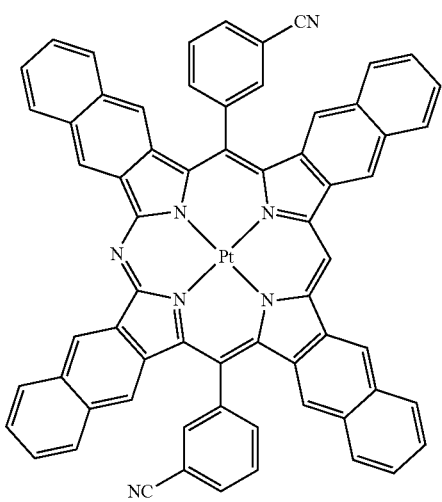
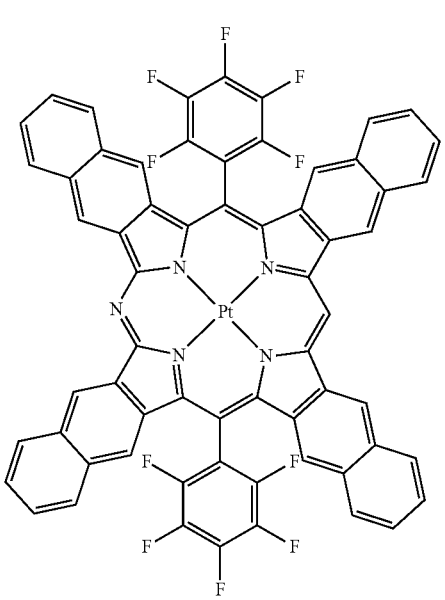
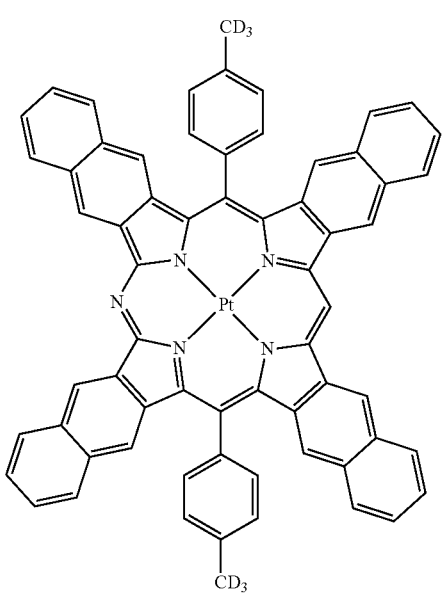
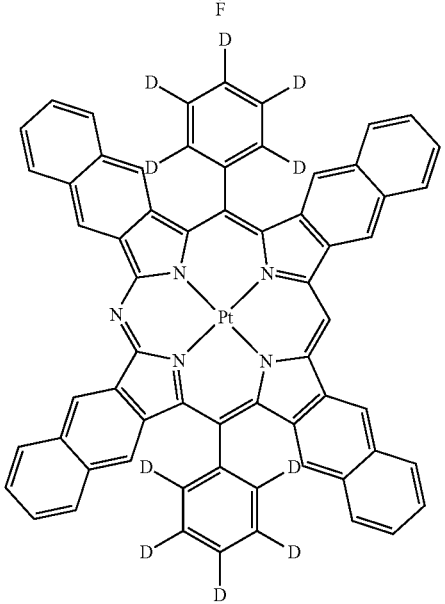

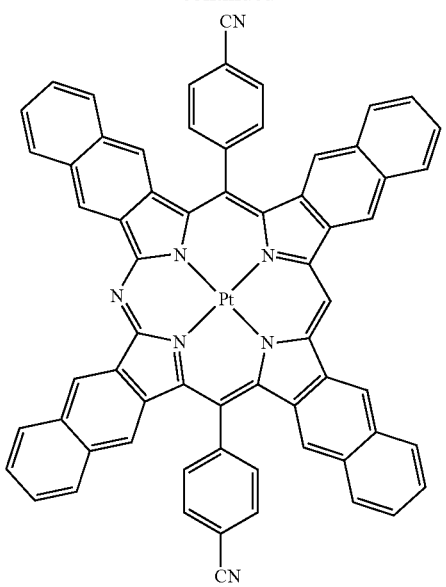
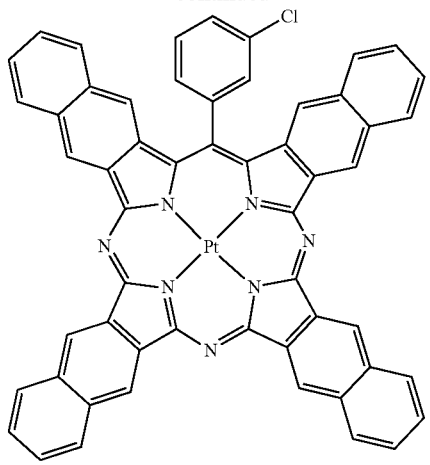
Examples of complexes of General Formula V are shown below.
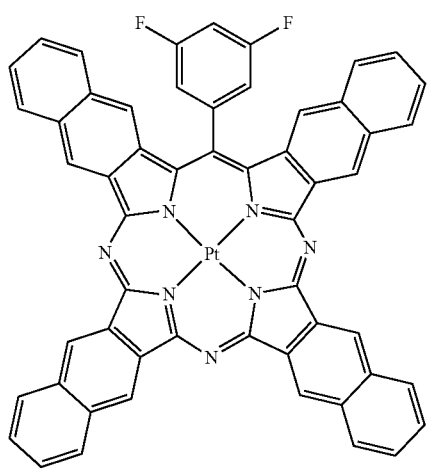
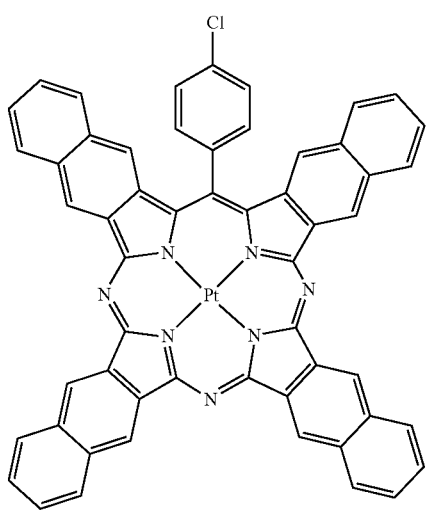
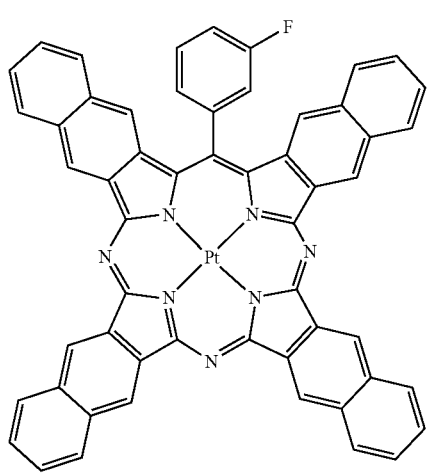
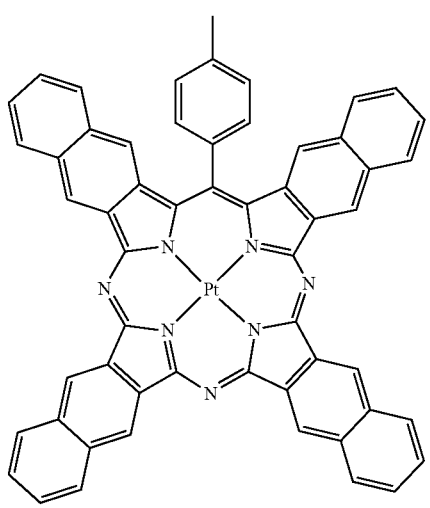

47
-continued
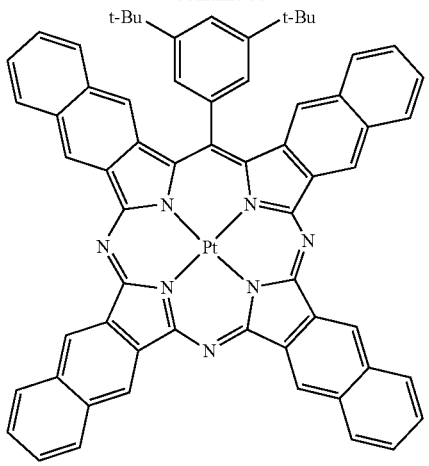
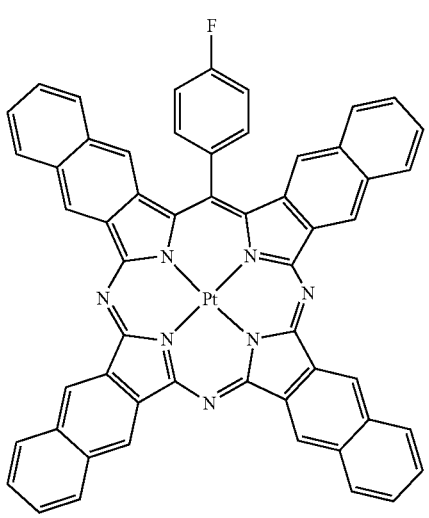
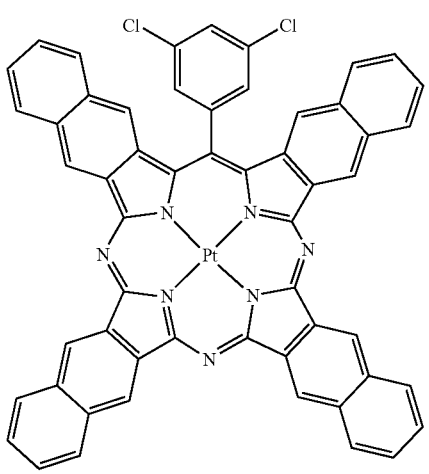
48
-continued
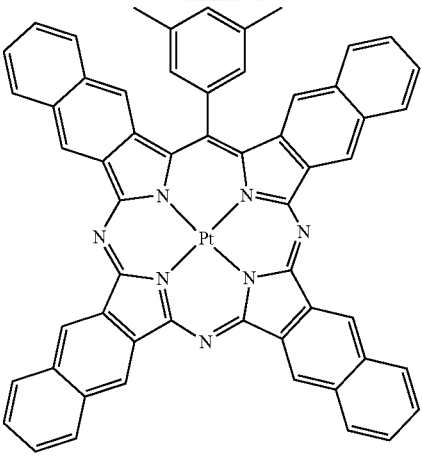
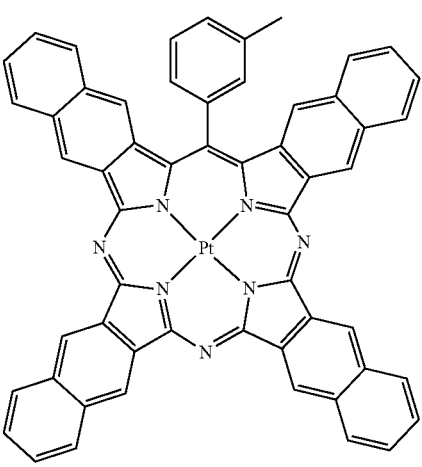
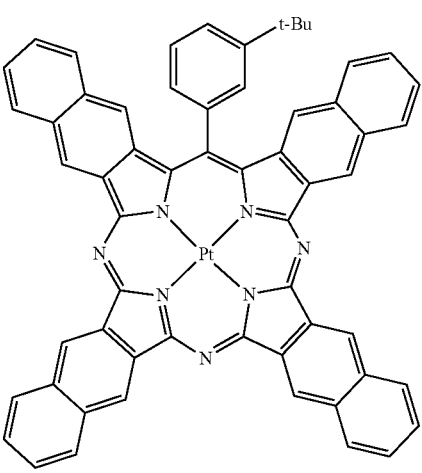

49
-continued
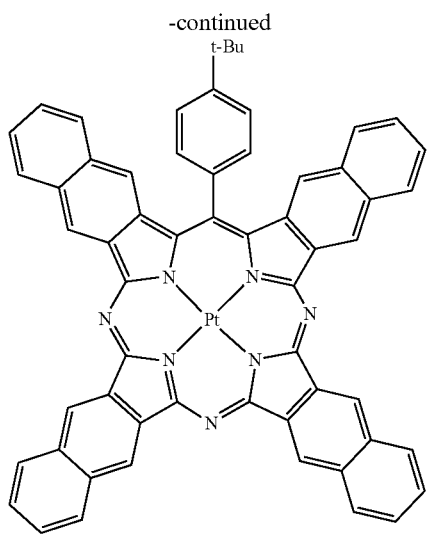
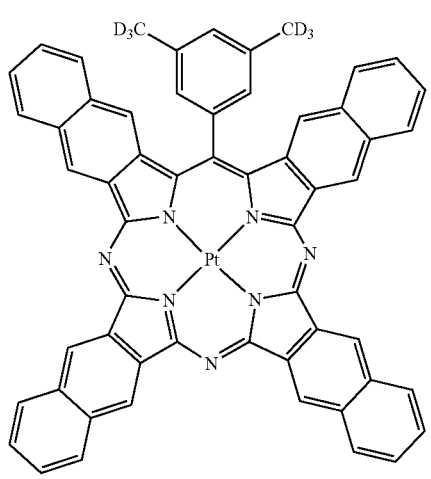
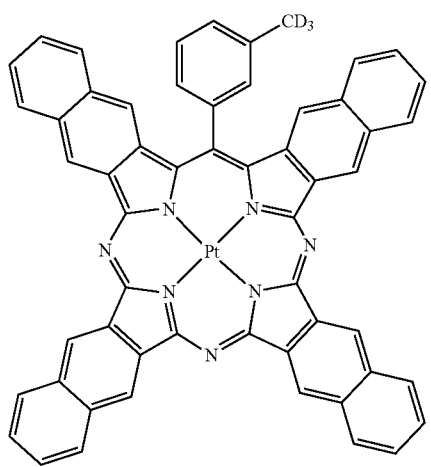
50
-continued
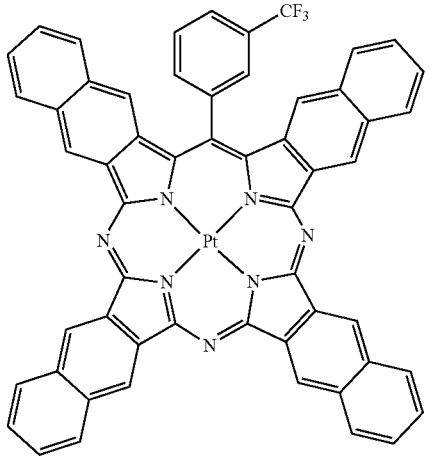
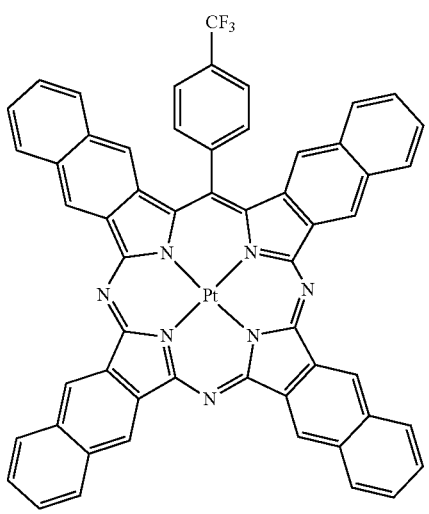
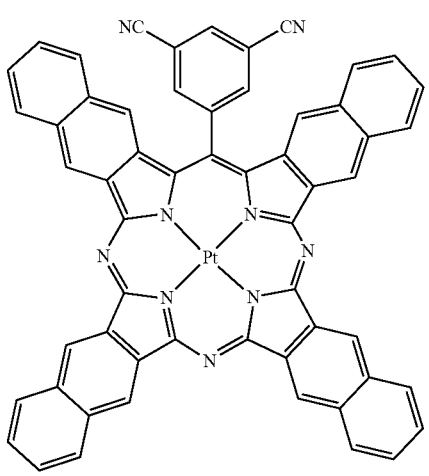

51
-continued
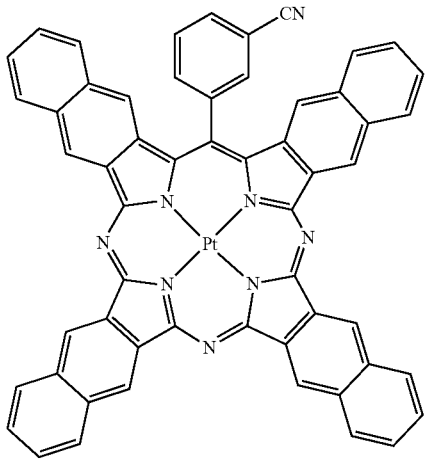
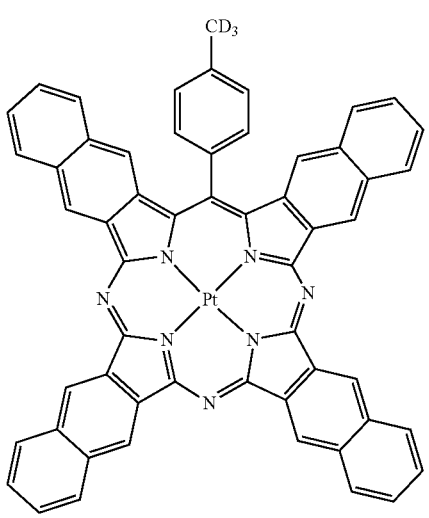
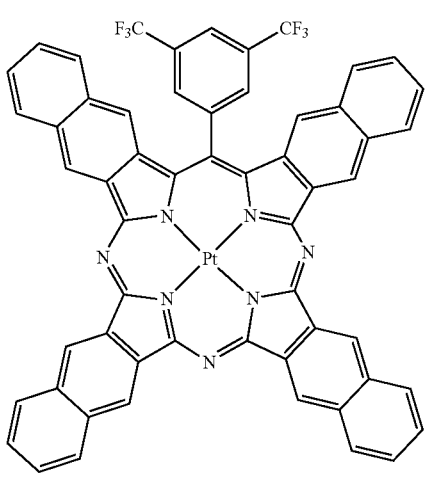
52
-continued
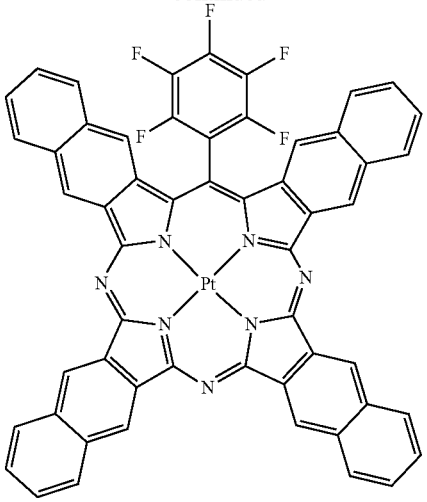
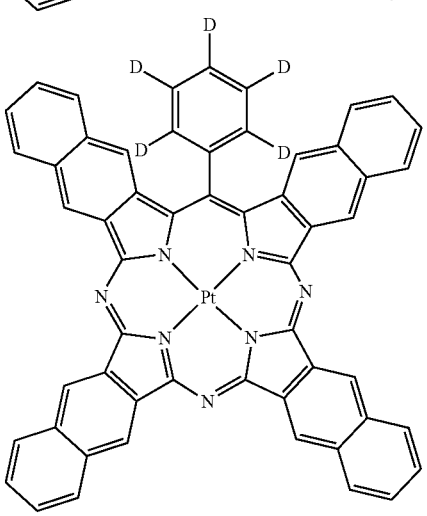
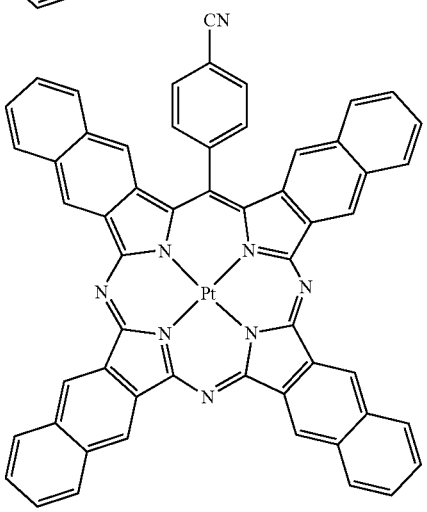
Compositions and Devices of the Invention
Also disclosed herein are devices comprising one or more compound and/or compositions disclosed herein.
In one aspect, the device is an electro-optical device. Electro-optical devices include, but are not limited to, photo-absorbing devices such as solar- and photo-sensitive devices, organic light emitting diodes (OLEDs), photo-emitting devices, or devices capable of both photo-absorption and emission and as markers for bio-applications. For example, the device can be an OLED.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. Such devices are disclosed herein which comprise one or more of the compounds or compositions disclosed herein.

OLEDs can be produced by methods known to those skilled in the art. In general, the OLED is produced by successive vapor deposition of the individual layers onto a suitable substrate. Suitable substrates include, for example, glass, inorganic materials such as ITO or IZO or polymer films. For the vapor deposition, customary techniques may be used, such as thermal evaporation, chemical vapor deposition (CVD), physical vapor deposition (PVD) and others.

In an alternative process, the organic layers may be coated from solutions or dispersions in suitable solvents, in which case coating techniques known to those skilled in the art are employed. Suitable coating techniques are, for example, spin-coating, the casting method, the Langmuir-Blodgett ("LB") method, the inkjet printing method, dip-coating, letterpress printing, screen printing, doctor blade printing, slit-coating, roller printing, reverse roller printing, offset lithography printing, flexographic printing, web printing, spray coating, coating by a brush or pad printing, and the like. Among the processes mentioned, in addition to the aforementioned vapor deposition, preference is given to spin-coating, the inkjet printing method and the casting method since they are particularly simple and inexpensive to perform. In the case that layers of the OLED are obtained by the spin-coating method, the casting method or the inkjet printing method, the coating can be obtained using a solution prepared by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide, water and mixtures thereof.

Compounds described herein can be used in a light emitting device such as an OLED. FIG. 1 depicts a cross-sectional view of an OLED 100. OLED 100 includes substrate 102, anode 104, hole-transporting material(s) (HTL) 106, light processing material 108, electron-transporting material(s) (ETL) 110, and a metal cathode layer 112. Anode 104 is typically a transparent material, such as indium tin oxide. Light processing material 108 may be an emissive material (EML) including an emitter and a host.

In various aspects, any of the one or more layers depicted in FIG. 1 may include indium tin oxide (ITO), poly(3,4-ethylenedioxythiophene) (PEDOT), polystyrene sulfonate (PSS), N,N'-di-1-naphthyl-N,N-diphenyl-1,1'-biphenyl-4,4'diamine (NPD), 1,1-bis((di-4-tolylamino)phenyl)cyclohexane (TAPC), 2,6-Bis(N-carbazolyl)pyridine (mCpy), 2,8-bis(diphenylphosphoryl)dibenzothiophene (PO15), LiF, Al, or a combination thereof.

Light processing material 108 may include one or more compounds of the present disclosure optionally together with a host material. The host material can be any suitable host material known in the art. In one embodiment, the emission color of an OLED is determined by the emission energy (optical energy gap) of the light processing material 108, which can be tuned by tuning the electronic structure of the emitting compounds, the host material, or both. Both the hole-transporting material in the HTL layer 106 and the electron-transporting material(s) in the ETL layer 110 may include any suitable hole-transporter known in the art.

Compounds described herein may exhibit phosphorescence. Phosphorescent OLEDs (i.e., OLEDs with phosphorescent emitters) typically have higher device efficiencies than other OLEDs, such as fluorescent OLEDs. Light emitting devices based on electrophosphorescent emitters are described in more detail in WO2000/070655 to Baldo et al., which is incorporated herein by this reference for its teaching of OLEDs, and in particular phosphorescent OLEDs.

As contemplated herein, an OLED of the present invention may include an anode, a cathode, and an organic layer disposed between the anode and the cathode. The organic layer may include a host and a phosphorescent dopant. The organic layer can include a compound of the invention and its variations as described herein.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In one embodiment, the consumer product is selected from the group consisting of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, and a sign.

In some embodiments of the emissive region, the emissive region further comprises a host, wherein the host comprises at least one selected from the group consisting of metal complex, triphenylene, carbazole, dibenzothiophene, dibenzofuran, dibenzoselenophene, aza-triphenylene, aza-carbazole, aza-dibenzothiophene, aza-dibenzofuran, and aza-dibenzoselenophene.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of CnH2n+1, OCnH2n+1, OAr1, N(CnH2n+1)2, N(Ar1)(Ar2), CH=CH—CnH2n+1, C≡C—CnH2n+1, Ar1, Ar1-Ar2, and CnH2n-Ar1, or the host has no substitutions. In the preceding substituents n can range from 1 to 10; and Ar1 and Ar2 can be independently selected from the group consisting of benzene, biphenyl, naphthalene, triphenylene, carbazole, and heteroaromatic analogs thereof. The host can be an inorganic compound. For example, a Zn containing inorganic material e.g. ZnS.

Suitable hosts may include, but are not limited to, mCP (1,3-bis(carbazol-9-yl)benzene), mCPy (2,6-bis(N-carbazolyl)pyridine), TCP (1,3,5-tris(carbazol-9-yl)benzene), TCTA (4,4',4"-tris(carbazol-9-yl)triphenylamine), TPBi (1,3,5-tris(1-phenyl-1-H-benzimidazol-2-yl)benzene), mCBP (3,3-di(9H-carbazol-9-yl)biphenyl), pCBP (4,4'-bis(carbazol-9-yl)biphenyl), CDBP (4,4'-bis(9-carbazolyl)-2,2'-dimethylbiphenyl), DMFL-CBP (4,4'-bis(carbazol-9-yl)-9,9-dimethylfluorene), FL-4CBP (4,4'-bis(carbazol-9-yl)-9,9-bis(9-phenyl-9H-carbazole)fluorene), FL-2CBP (9,9-bis(4-carbazol-9-yl)phenyl)fluorene, also abbreviated as CPF), DPFL-CBP (4,4'-bis(carbazol-9-yl)-9,9-ditolylfluorene), FL-2CBP (9,9-bis(9-phenyl-9H-carbazole)fluorene), Spiro-CBP (2,2',7,7'-tetrakis(carbazol-9-yl)-9,9'-spirobifluorene), ADN (9,10-di(naphth-2-yl)anthracene), TBADN (3-tert-butyl-9,10-di(naphth-2-yl)anthracene), DPVBi (4,4'-bis(2,2-diphenylethen-1-yl)-4,4'-dimethylphenyl), p-DMDPVBi (4,4'-bis(2,2-diphenylethen-1-yl)-4,4'-dimethylphenyl), TDAF (tert(9,9-diarylfluorene)), BSBF (2-(9,9'-spirobifluoren-2-yl)-9,9'-spirobifluorene), TSBF (2,7-bis(9,9'-spirobifluoren-2-yl)-9,9'-spirobifluorene), BDAF (bis(9,9-diarylfluorene)), p-TDPVBi (4,4'-bis(2,2-diphenylethen-1-yl)- 4,4'-di-(tert-butyl)phenyl), TPB3 (1,3,5-tri(pyren-1-yl)benzene, PBD (2-(4-biphenylyl)-5-(4-tert-butylphenyl)-1,3,4-oxadiazole), BCP (2,9-dimethyl-4,7-diphenyl-1,10-phenanthroline), BP-OXD-Bpy (6,6'-bis[5-(biphenyl-4-yl)-1,3,4-oxadiazo-2-yl]-2,2'-bipyridyl), NTAZ (4-(naphth-1-yl)-3,5-diphenyl-4H-1,2,4-triazole), Bpy-OXD (1,3-bis[2-(2,2'-bipyrid-6-yl)-1,3,4oxadiazo-5-yl]benzene), BPhen (4,7-diphenyl-1,10-phenanthroline), TAZ (3-(4-biphenylyl)-4-phenyl-5-tert-butylphenyl-1,2,4-triazole), PADN (2-phenyl-9,10-di(naphth-2-yl)anthracene), Bpy-FOXD (2,7-bis[2-(2,2'-bipyrid-6-yl)-1,3,4-oxadiazol-5-yl]-9,9-dimethylfluorene), OXD-7 (1,3-bis[2-(4-tert-butylphenyl)-1,3,4-oxadiazol-5-yl]benzene), HNBphen (2-(naphth-2-yl)-4,7-diphenyl-1,10-phenanthroline), NBphen (2,9-bis(naphth-2-yl)-4,7-diphenyl-1,10-phenanthroline), 3TPYMB (tris(2,4,6-trimethyl-3-(pyrid-3-yl)phenyl)borane), 2-NPIP (1-methyl-2-(4-(naphth-2-yl)phenyl)-1H-imidazo[4,5-f]-[1,10]phenanthroline), Liq (8-hydroxyquinolinolatolithium), and Alq (bis(2-methyl-8-quinolinolate)-4-(phenylphenolato) aluminum), and also of mixtures of the aforesaid substances.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoOx; a p-type semiconducting organic compound, such as 1,4,5,8,9,12-Hexaazatriphenylenehexacarbonitrile; a metal complex, and a cross-linkable compounds.

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

One or more additional emitter dopants may be used in conjunction with the compound of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

In yet another aspect of the present disclosure, a formulation that comprises the novel compound disclosed herein is described. The formulation can include one or more components selected from the group consisting of a solvent, a host, a hole injection material, hole transport material, and an electron transport layer material, disclosed herein.

EXPERIMENTAL EXAMPLES

The following examples are put forth so as to provide those of ordinary skill in the art with a complete disclosure and description of how the complexes, compositions, articles, devices and/or methods claimed herein are made and evaluated, and are intended to be purely exemplary and are not intended to be limiting in scope. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Various methods for the preparation method of the complexes and devices described herein are recited in the examples. These methods are provided to illustrate various methods of preparation, but are not intended to limit any of the methods recited herein. Accordingly, one of skill in the art in possession of this disclosure could readily modify a recited method or utilize a different method to prepare one or more of the complexes and devices described herein. The following aspects are only exemplary and are not intended to be limiting in scope. Temperatures, catalysts, concentrations, reactant compositions, and other process conditions can vary, and one of skill in the art, in possession of this disclosure, could readily select appropriate reactants and conditions for a desired complex and devices.

This invention is to design porphyrins and azaporphyrin derivatives by adding fluorine functional groups or analogs, which will improve the thermal and chemical stability of porphyrin derivatives, enabling them available for optoelectronic applications.

FIGS. 2A-2E show steps in a synthetic procedure.

Example 1: Synthesis of PtTPTNP-F$_8$

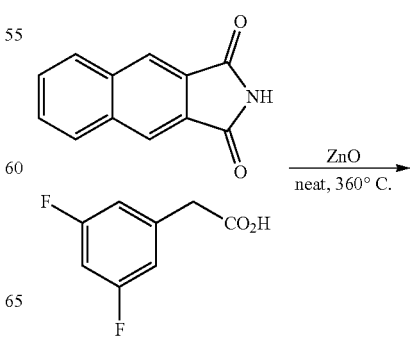

-continued

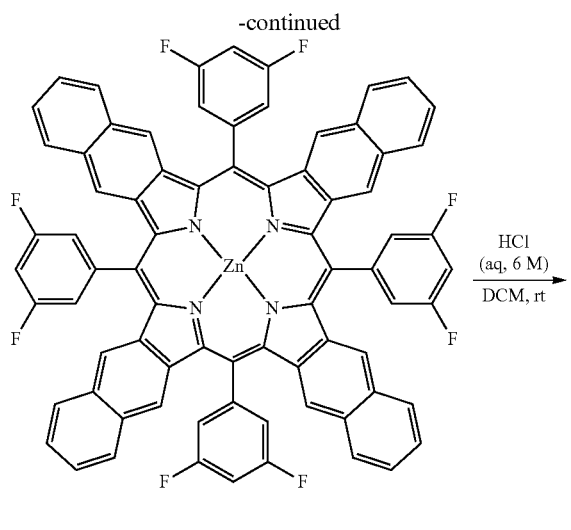

Example 2: Synthesis of ZnTPTNP-F$_8$

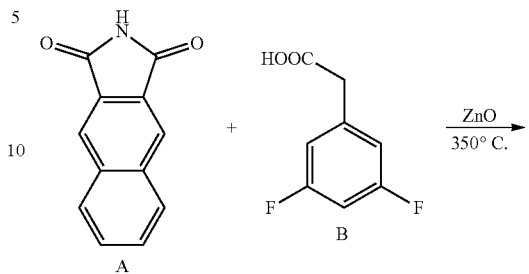

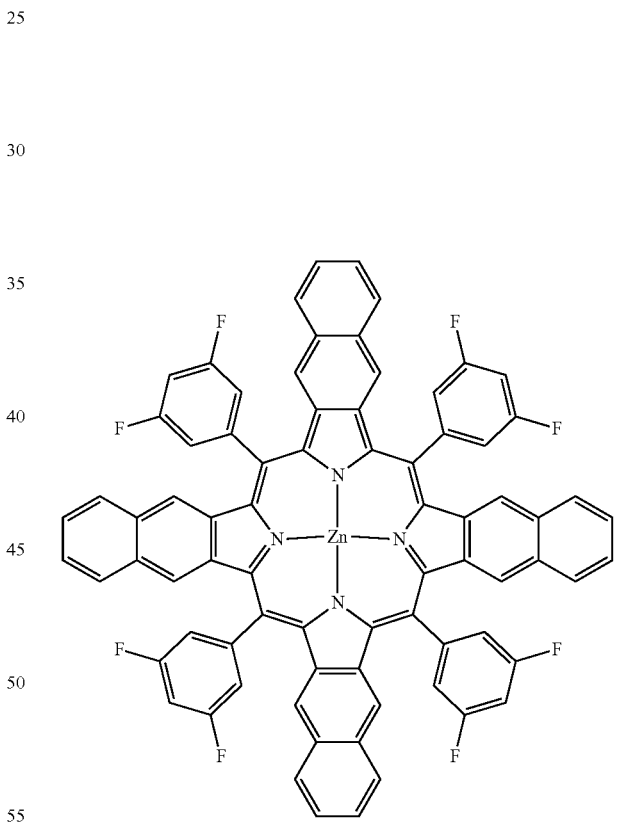

Compound B (1.72 g, 100 mmol) was added to a 100 ml three-neck flask and heated to 250° C. When B was completely melted, compound A (1.97 g 100 mmol) was added gradually in small portions. After 15 min, ZnO (200 mg, 25 mmol) was added to the mixture and the resulting mixture was heated to 350° C. for 24 hours under a nitrogen atmosphere. The reaction mixture was cooled down to room temperature. The residue was purified via column chromatography on silica with dichloromethane (DCM) as the eluent.

Example 3: Synthesis of H₂TPTNP-F₈

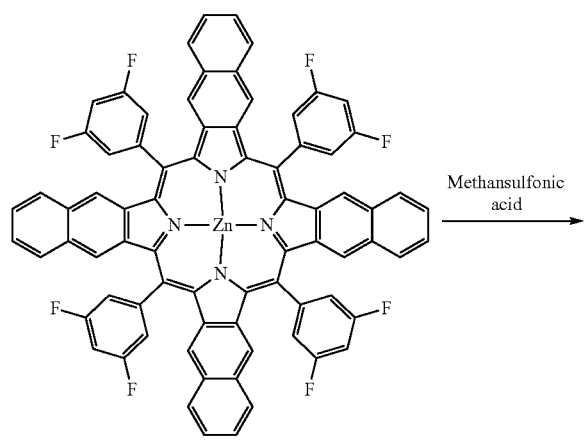

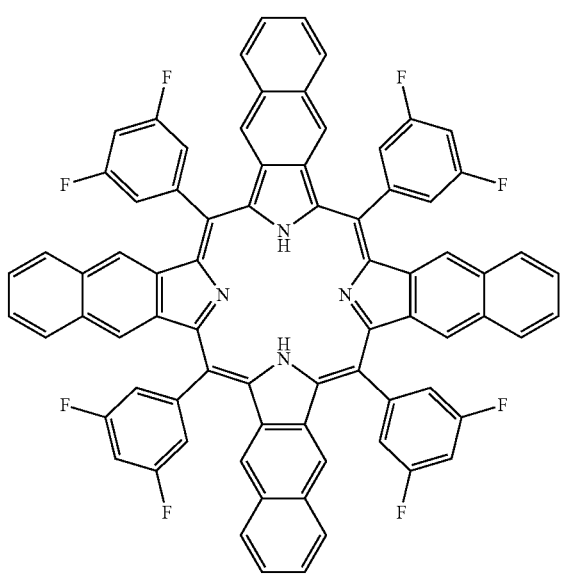

ZnTNTBP-F₈ (100 mg) was dissolved in 20 mL of methansulfonic acid, and the color changed from green to deep red. The mixture was stirred for 30 min at room temperature. The solution was poured into 100 ml of water, and the the precipitated solid was collected, washed with water several times, and dried.

Example 4: Synthesis of PtTPTNP-F₈

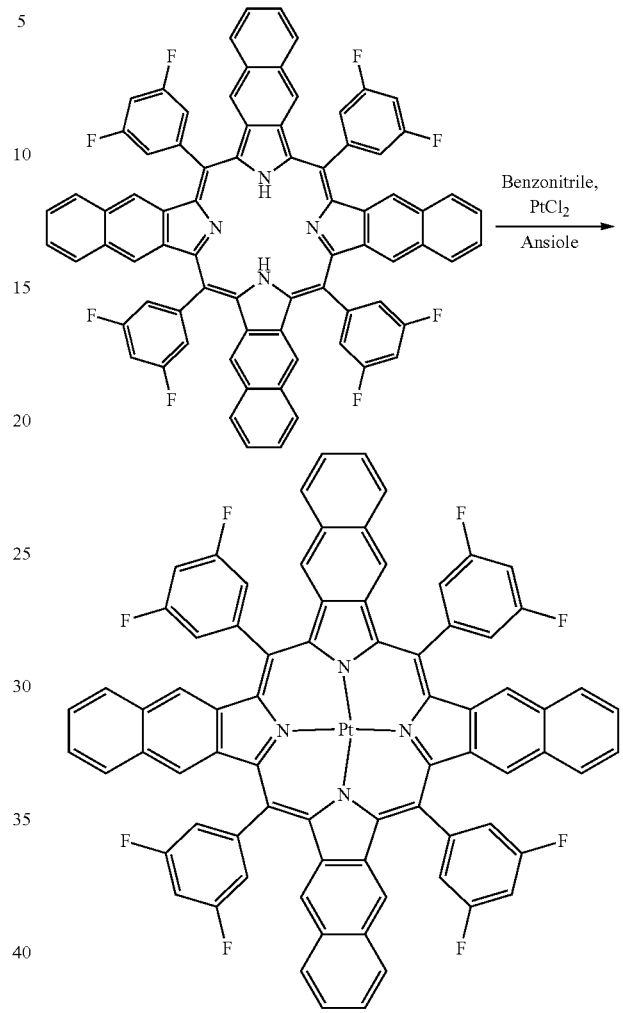

Figure 3:
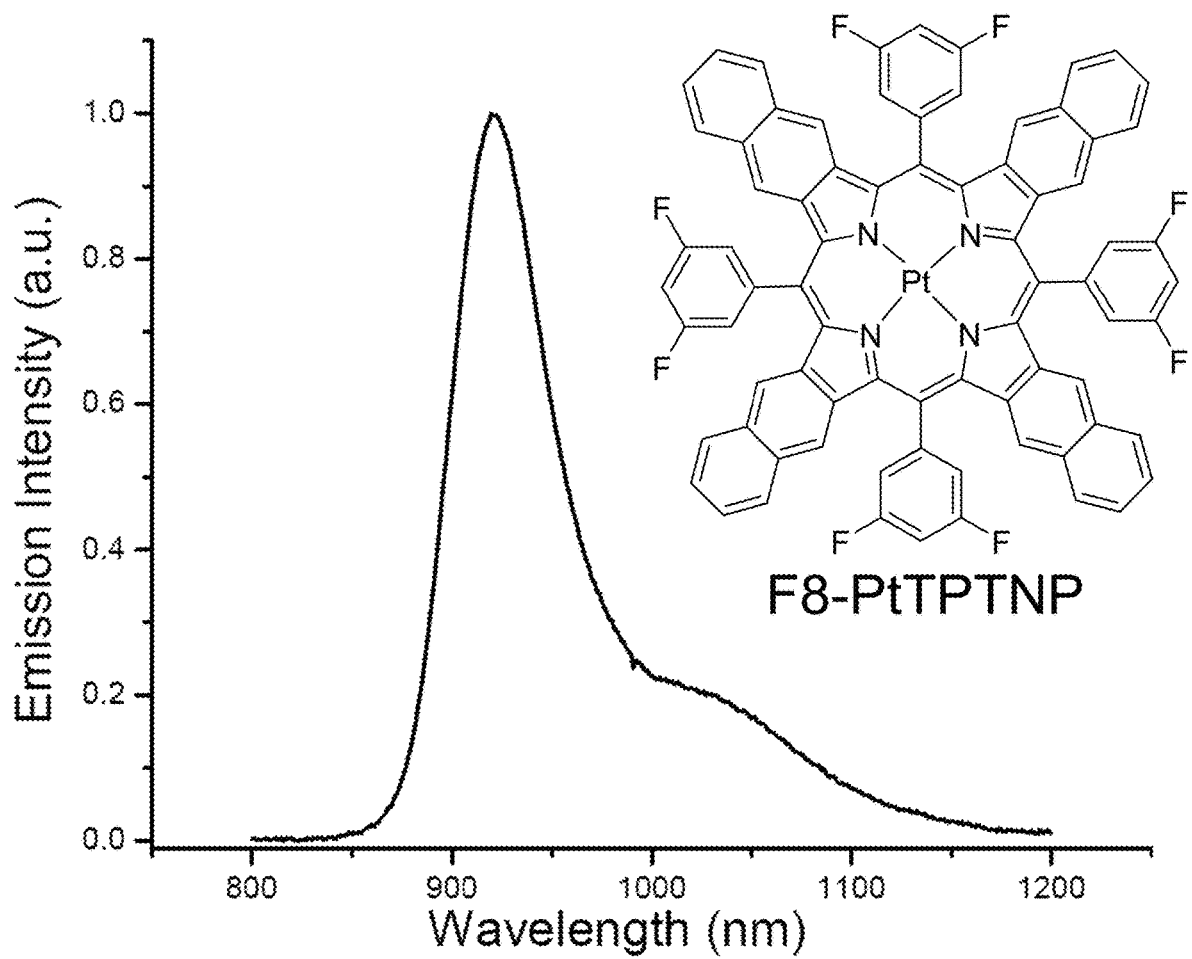
FIG. 3 shows a room temperature emission spectrum of PtTPTNP-Fs in tetrahydrofuran solution, prepared as described in Example 4.

PtCl$_2$ (80 mg, 0.3 mmol) was added to 1 mL of benzonitrile and the mixture was heated to 100° C. for 1 hour until the solution turned to clear. H$_2$TNTBP-F$_8$ (312 mg, 0.27 mmol) and 20 ml of anisole were added to the solution and the resulting mixture was heated to reflux for 24 hours under a nitrogen atmosphere. The solution was cooled down to room temperature and the solvent was removed by reduced pressure. The residue was purified via column chromatography on Al$_2$O$_3$ with DCM as the eluent. FIG. 3 shows a room temperature emission spectrum of PtTPTNP-Fs in tetrahydrofuran solution.

Figure 4:
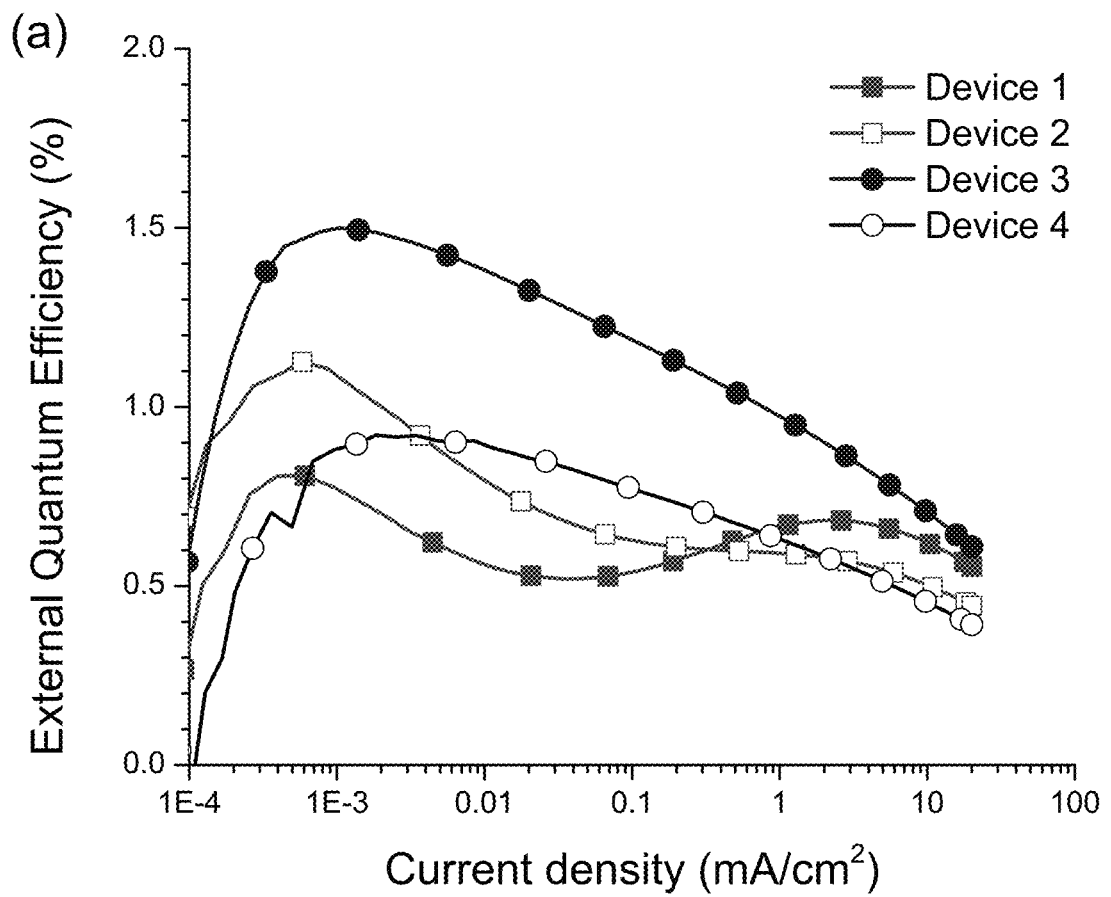
FIG. 4 is a plot of external quantum efficiency versus current density for devices in the structure: ITO/HATCN (10 nm)/NPD (40 nm)/EBL/4% F8-PtTPTNP: Alq3 (25 nm)/HBL/BPyTP (40 nm)/Liq (2 nm)/Al, where in device 1: EBL=TrisPCz (10 nm), HBL=BAlq (10 nm); in device 2: EBL=TrisPCz (10 nm), HBL=none; in device 3: EBL=none, HBL=BAlq (10 nm); in device 4: EBL=HBL=none.
Figure 5:
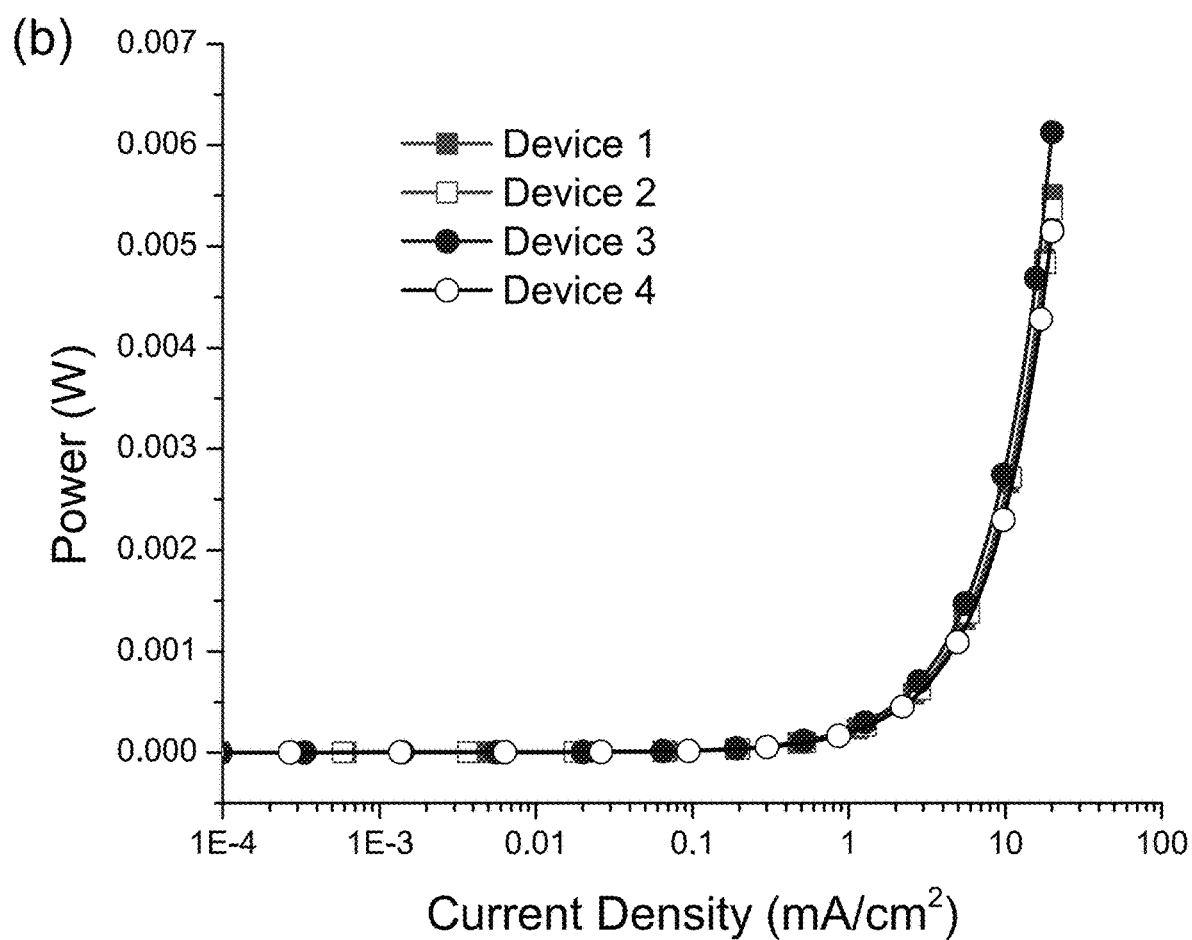
FIG. 5 is a plot of optic power versus current density for devices in the structure: ITO/HATCN (10 nm)/NPD (40 nm)/EBL/4% F8-PtTPTNP: Alq3 (25 nm)/HBL/BPyTP (40 nm)/Liq (2 nm)/Al, where in device 1: EBL=TrisPCz (10 nm), HBL=BAlq (10 nm); in device 2: EBL=TrisPCz (10 nm), HBL=none; in device 3: EBL=none, HBL=BAlq (10 nm); in device 4: EBL=HBL=none.
Figure 6:
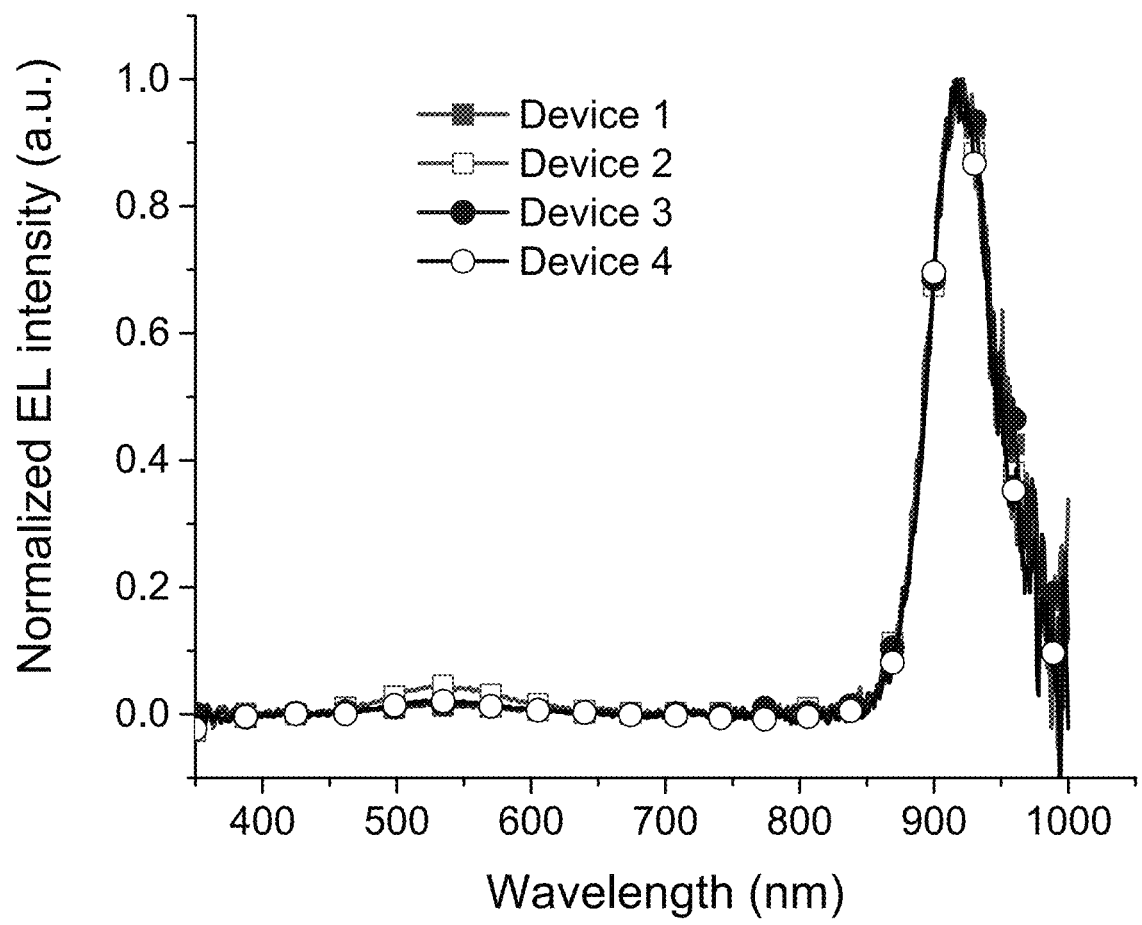
FIG. 6 depicts the electroluminescent spectra of devices in the structure: ITO/HATCN (10 nm)/NPD (40 nm)/EBL/4% F8-PtTPTNP: Alq3 (25 nm)/HBL/BPyTP (40 nm)/Liq (2 nm)/Al, where in device 1: EBL=TrisPCz (10 nm), HBL=BAlq (10 nm); in device 2: EBL=TrisPCz (10 nm), HBL=none; in device 3: EBL=none, HBL=BAlq (10 nm); in device 4: EBL=HBL=none.

Devices were prepared having the following structures: ITO/HATCN (10 nm)/NPD (40 nm)/EBL/4% F8-PtTPTNP:Alq3 (25 nm)/HBL/BPyTP (40 nm)/Liq (2 nm)/Al, where in device 1: EBL=TrisPCz (10 nm), HBL=BAlq (10 nm); in device 2: EBL=TrisPCz (10 nm), HBL=none; in device 3: EBL=none, HBL=BAlq (10 nm); in device 4: EBL=HBL=none. FIG. 4 is a plot of external quantum efficiency versus current density for the four devices. FIG. 5 is a plot of optic power versus current density for the four devices. FIG. 6 depicts the electroluminescent spectra of the four devices.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A complex represented by one of General Formulas I-V:

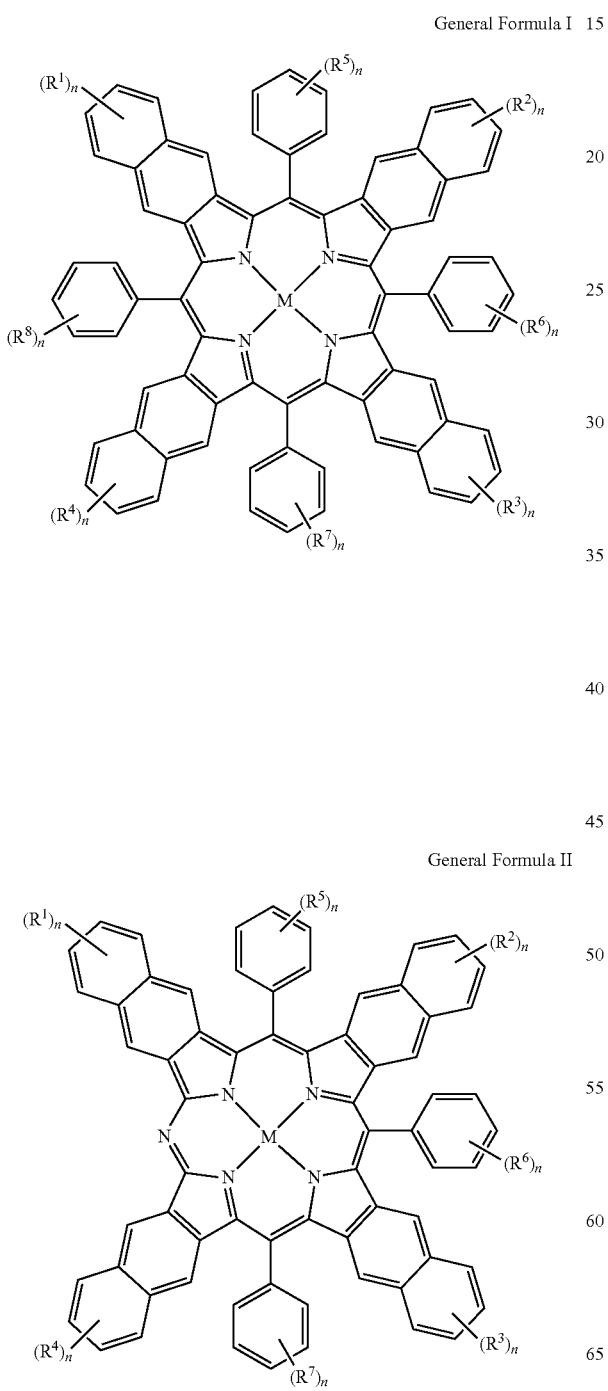

wherein:

M represents $Pt^{2+}$, $Pd^{2+}$, $Zn^{2+}$, or $Mg^{2+}$;

each $R^1$, $R^2$, $R^3$, and $R^4$ independently represents hydrogen, deuterium, halide, nitro, nitrile, hydroxyl, thiol, methyl-$d_3$, phenyl-$d_5$, amino, or substituted or unsubstituted $C_1$-$C_4$ alkyl, alkoxy, aryl, or amino;

each $R^5$, $R^6$, $R^7$, and $R^8$, when present, independently represents hydrogen, deuterium, fluoride, chloride, nitrile, methyl-$d_3$, phenyl-$d_5$, or substituted or unsubstituted $C_1$-$C_4$ alkyl or aryl; and each n is independently an integer, valency permitting;

wherein when the complex is represented by General Formula I, then at least one of the following conditions (i) and (ii) is satisfied:

(i) at least one of $R^5$ to $R^8$ is present and represents a substituent selected from the group consisting of chloride, methyl-d3, and phenyl-d5; or (ii) two occurrences of $R^5$ are present as fluoride at the 3- and 5-positions.

2. The complex of claim 1, represented by one of the following structures:

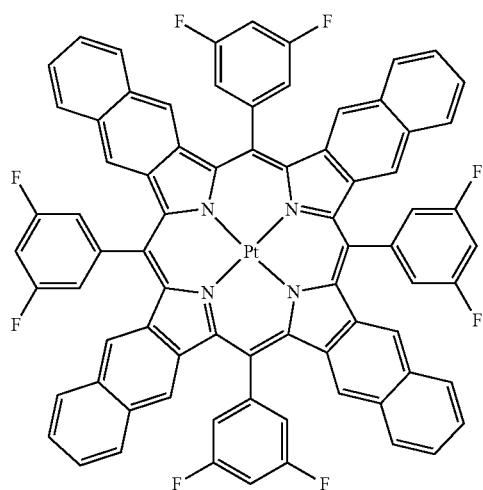

-continued

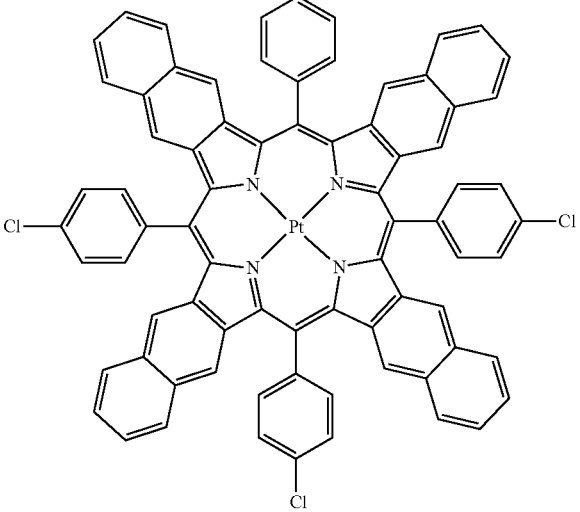

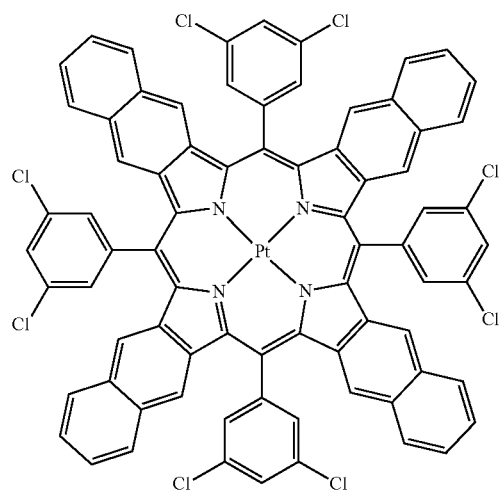

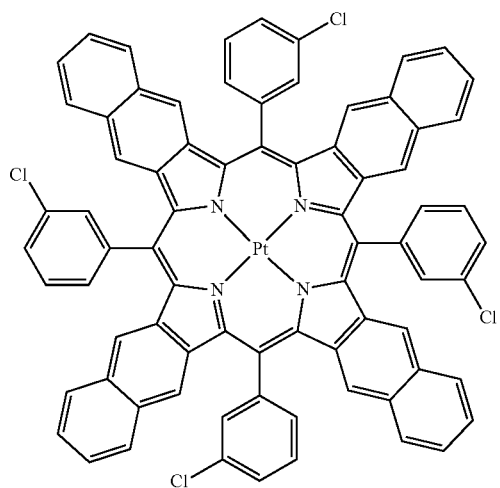

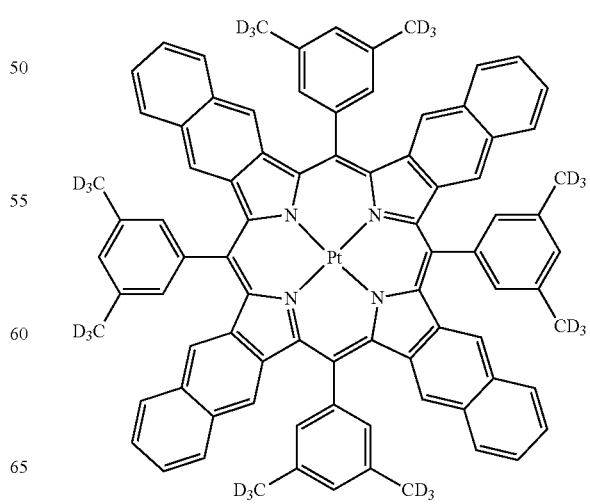

-continued
67
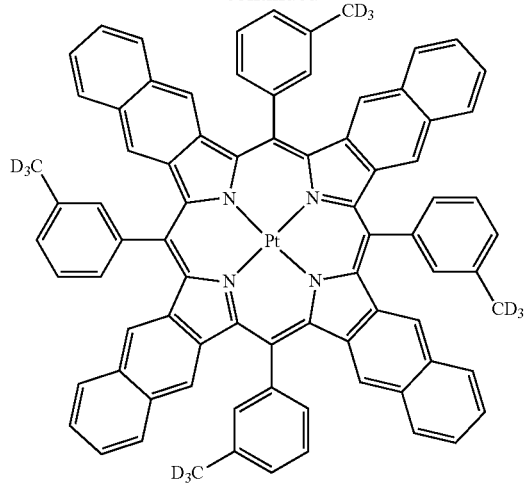
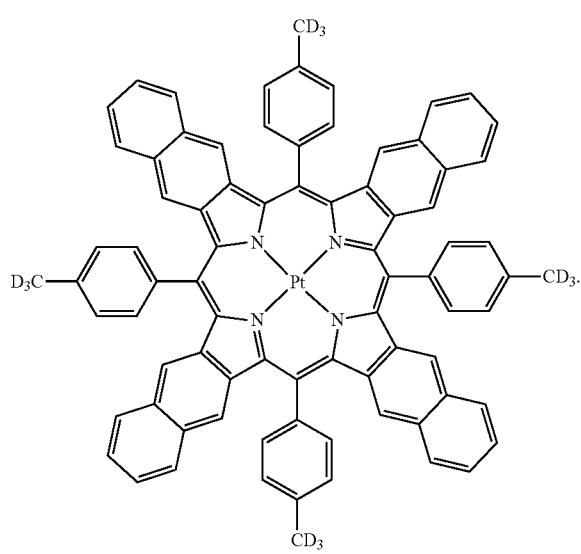
3. The complex of claim 1, represented by one of the following structures:
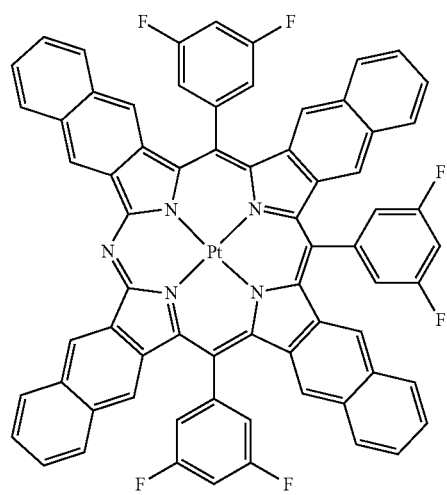
-continued
68
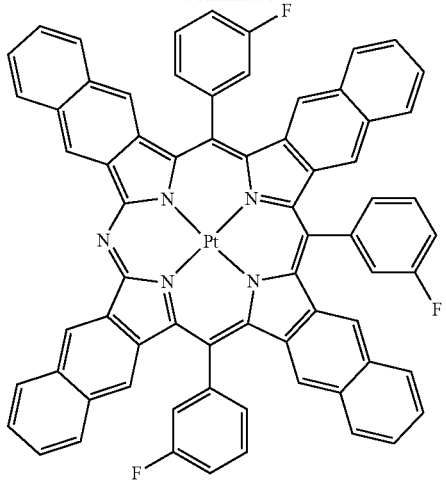
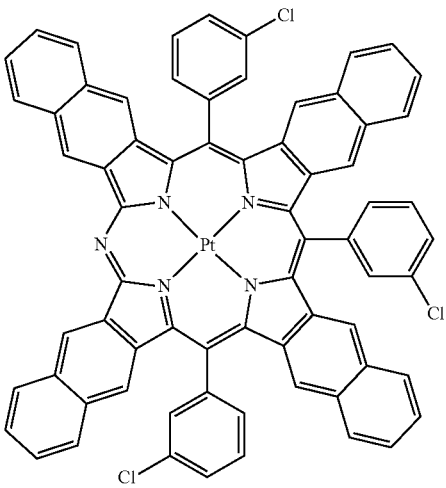
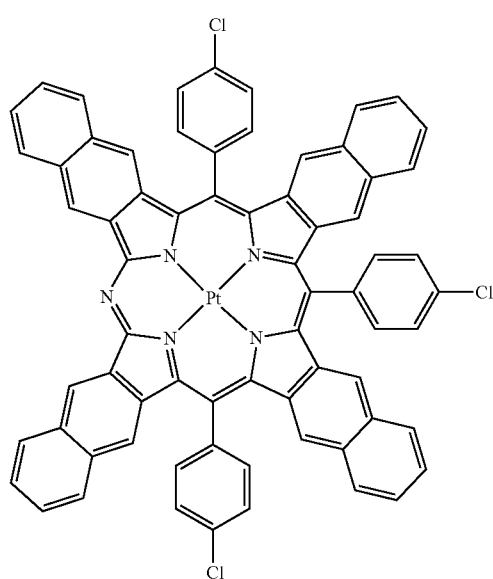

69
-continued
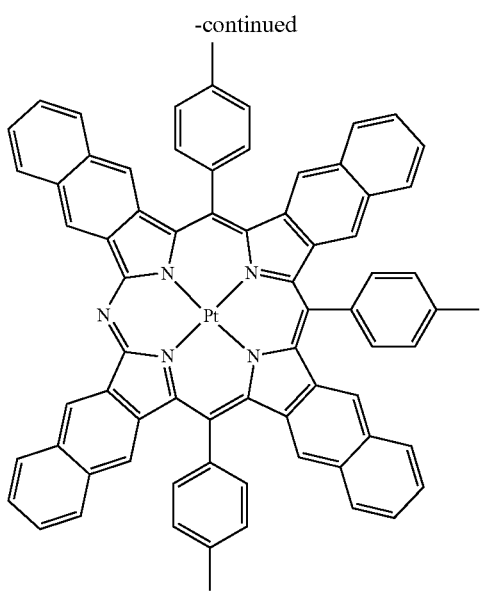
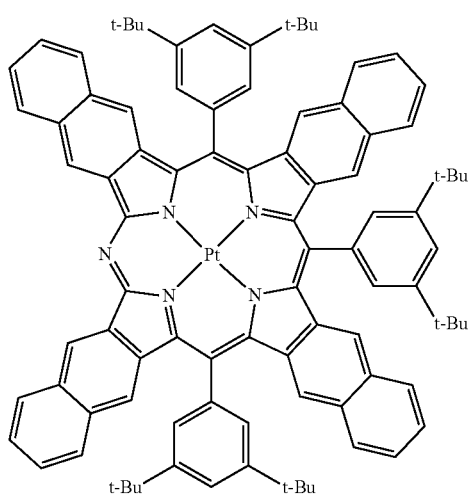
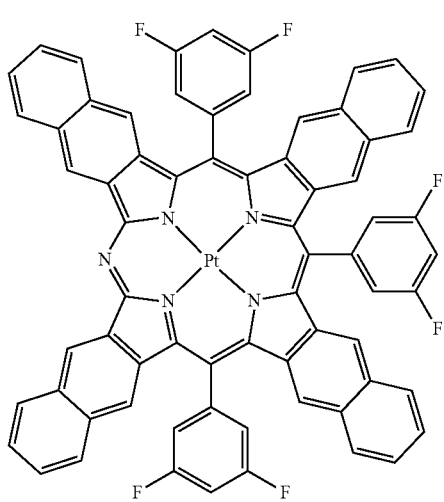
70
-continued
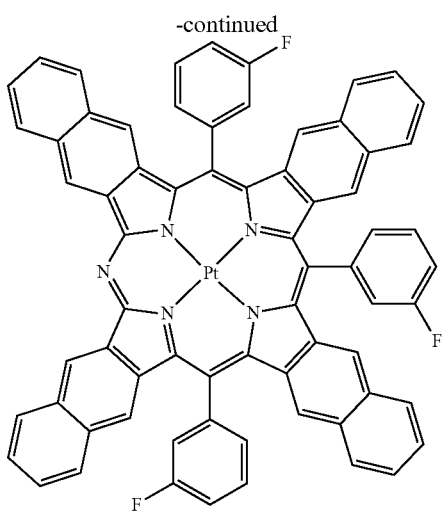
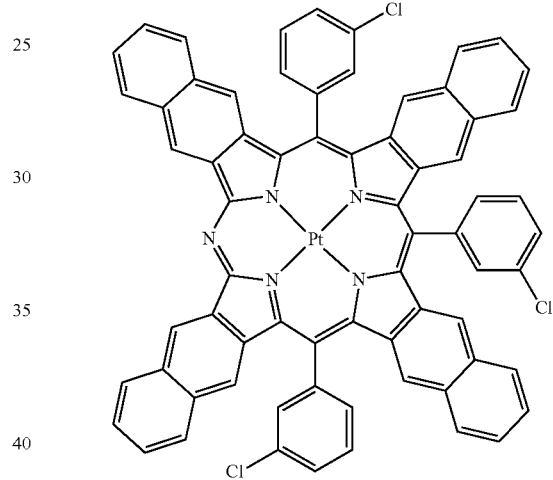
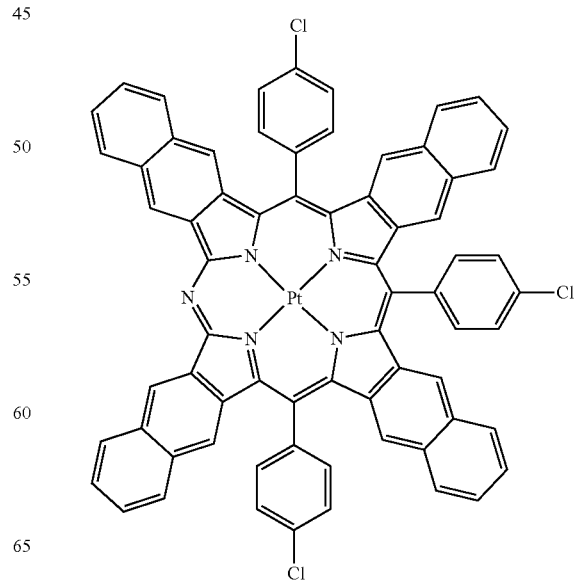

-continued
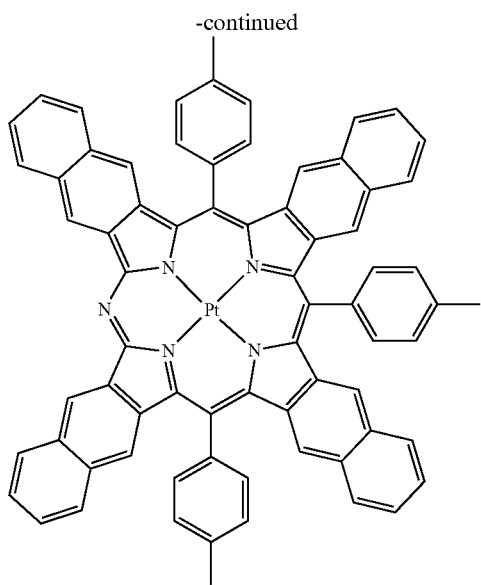
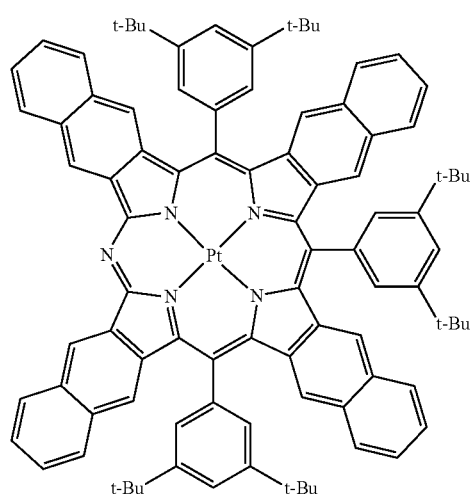
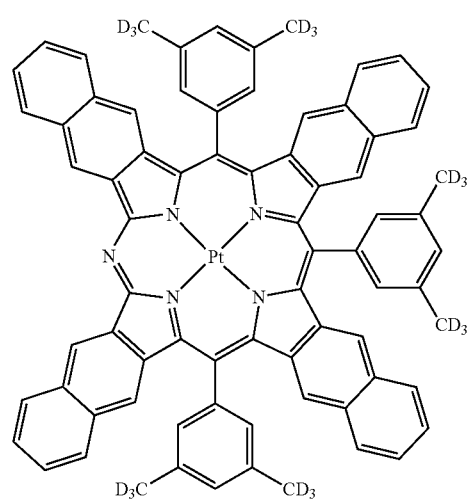
-continued
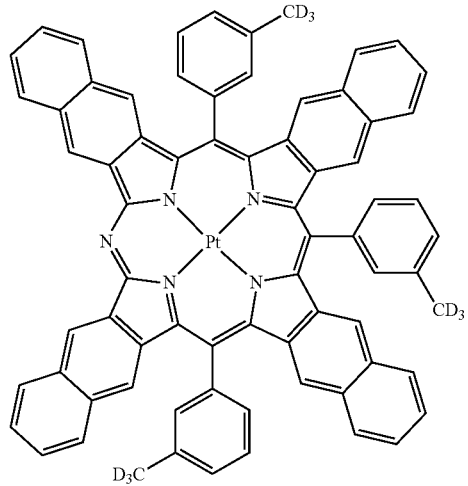
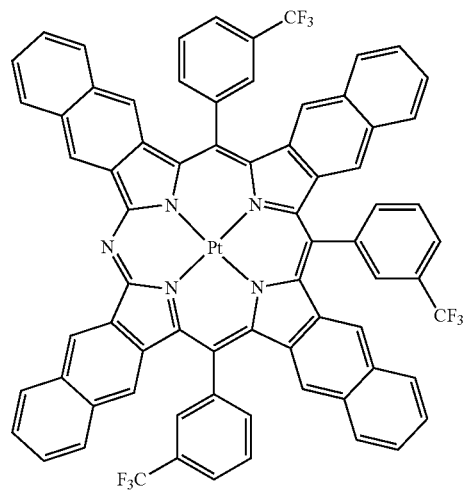
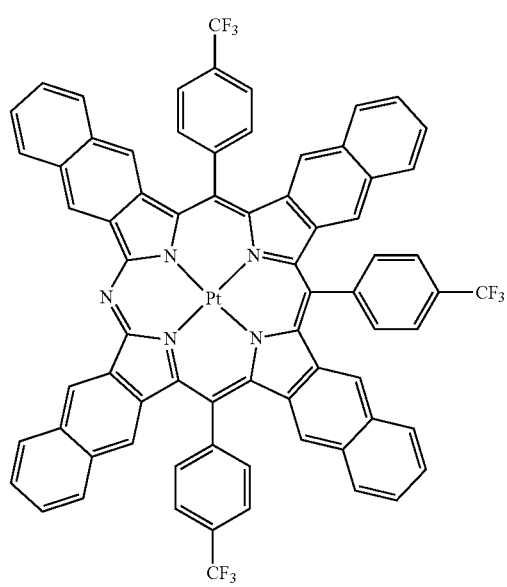

73
-continued
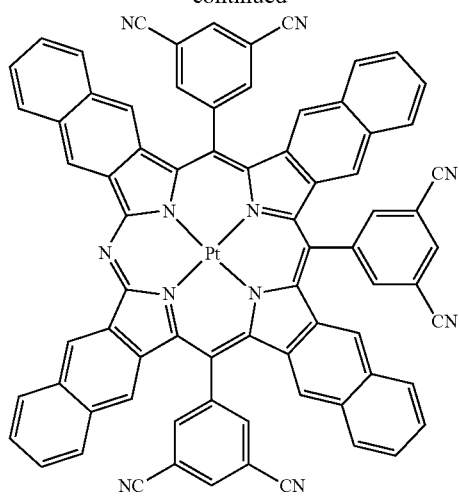
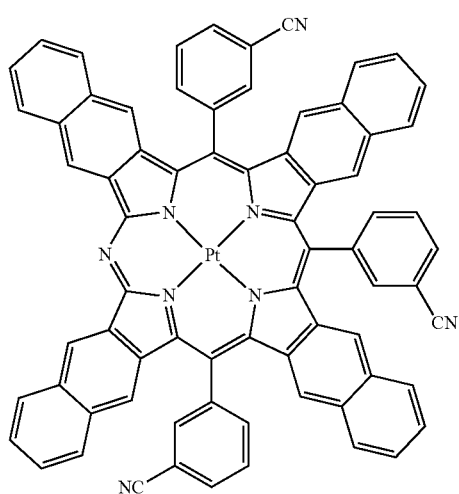
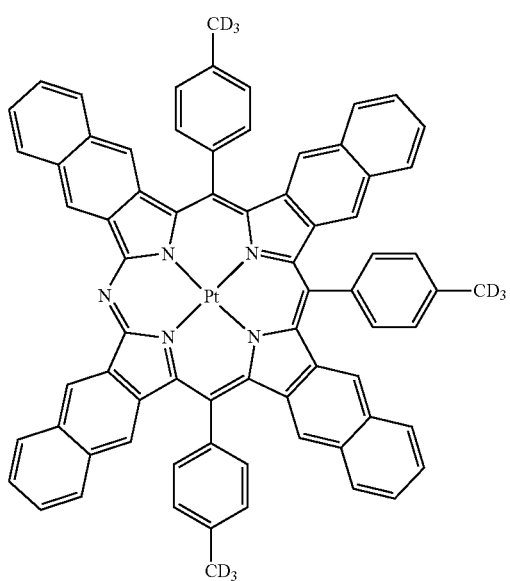
74
-continued
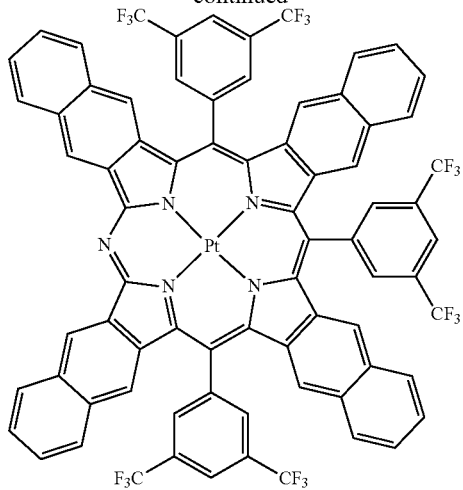
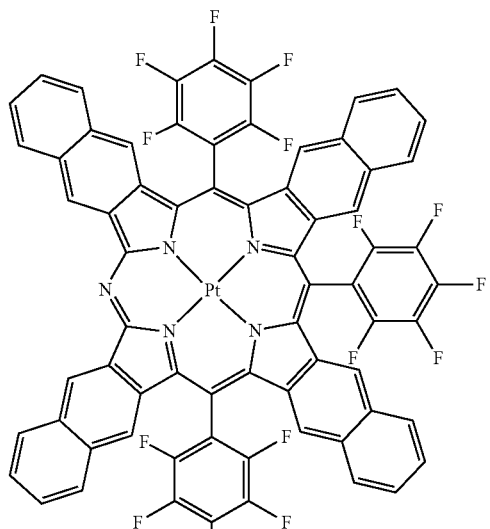
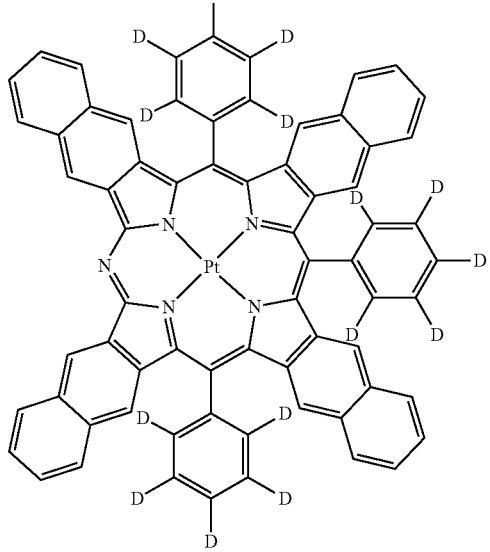

-continued
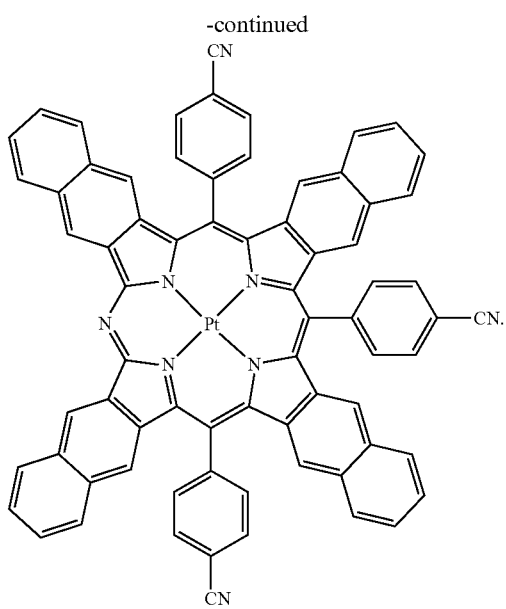
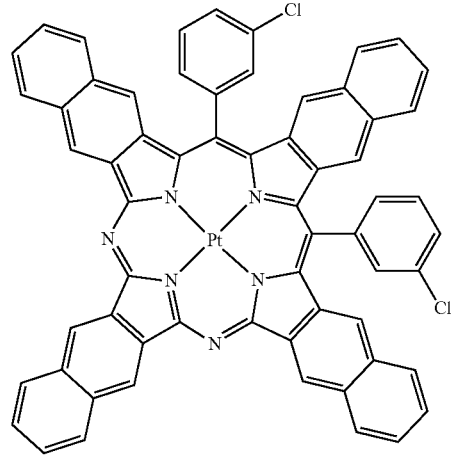
4. The complex of claim 1, represented by one of the following structures.
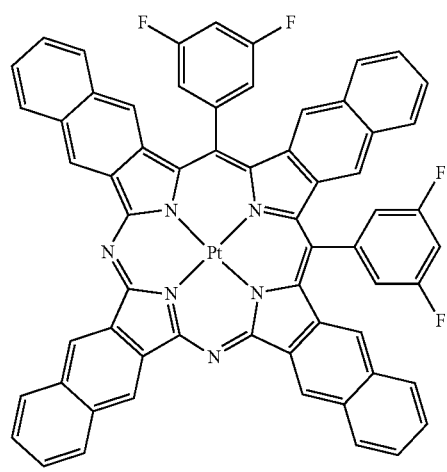
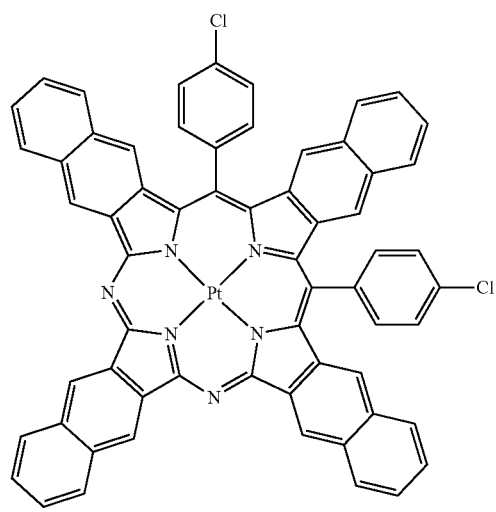
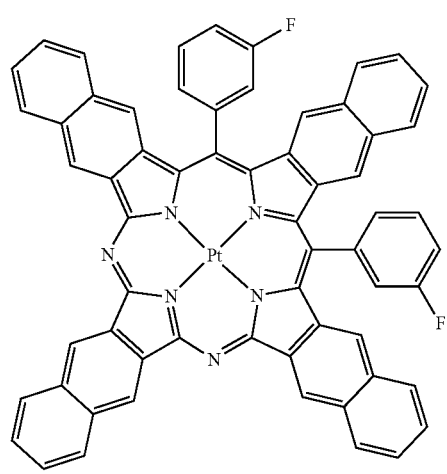
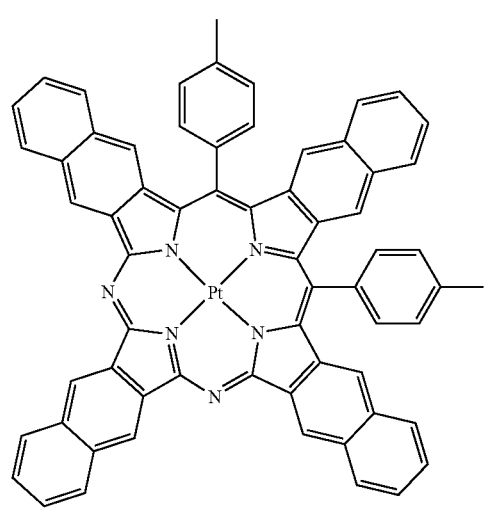

77
-continued
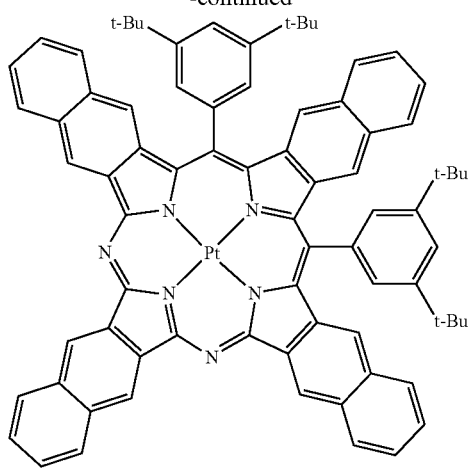
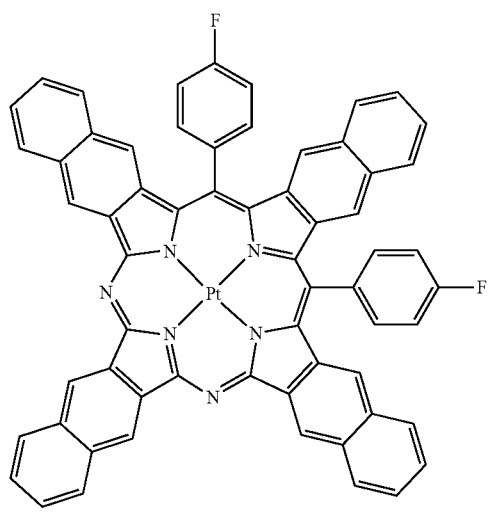
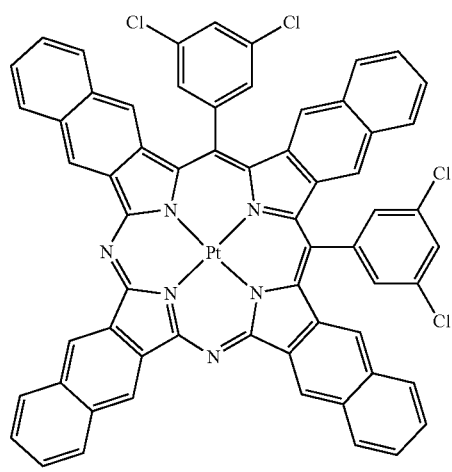
78
-continued
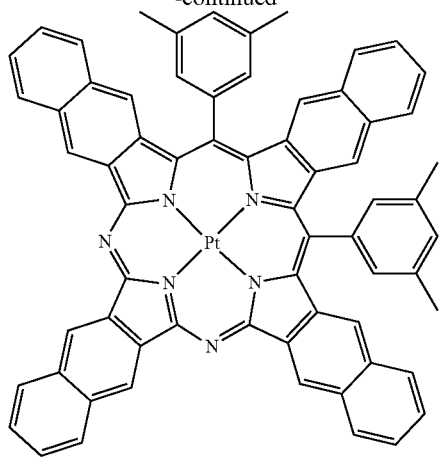
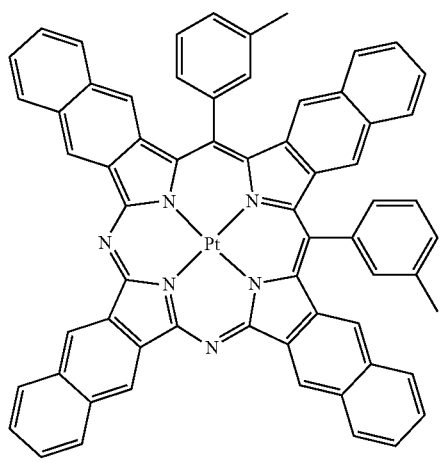
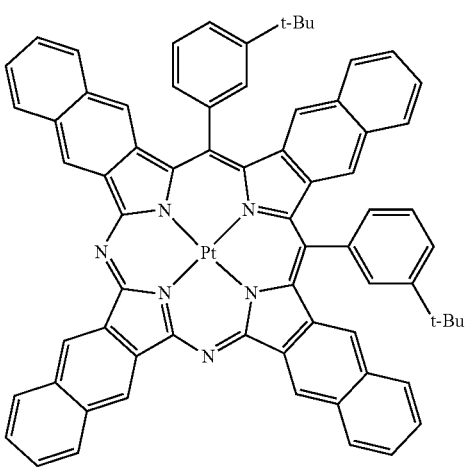

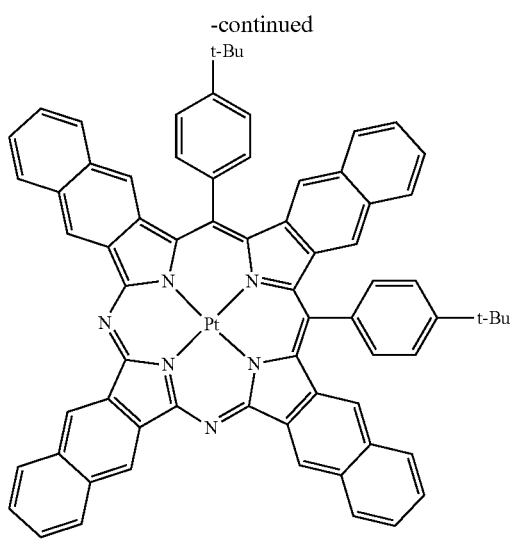
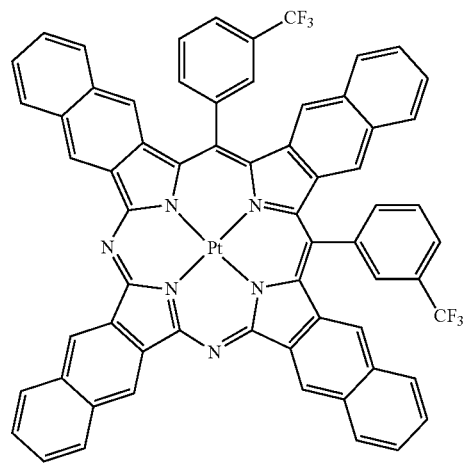
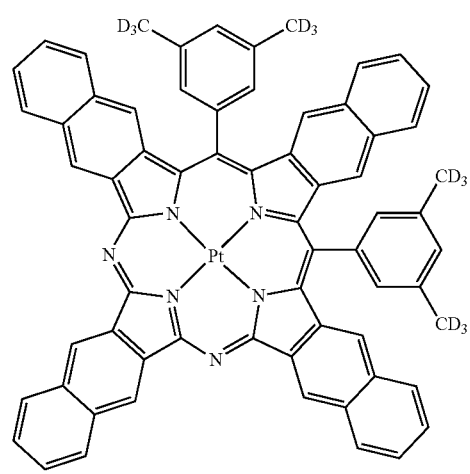
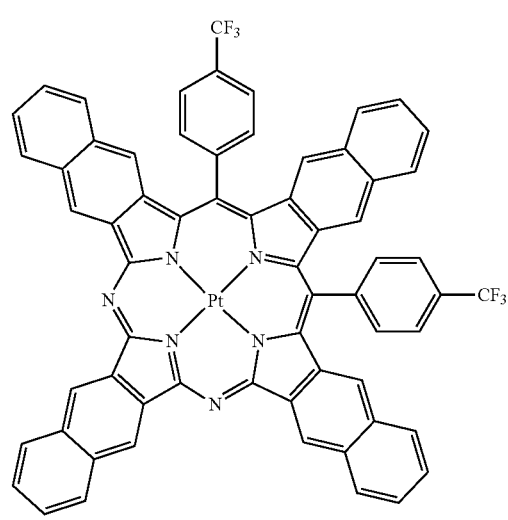
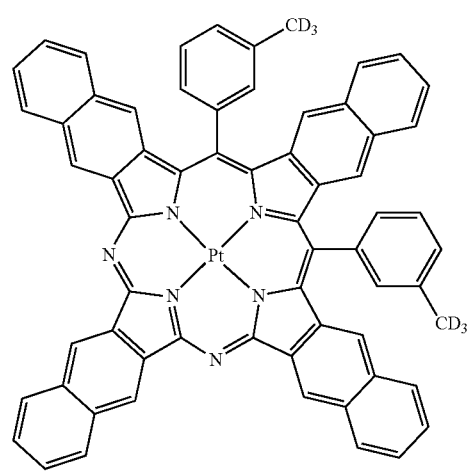
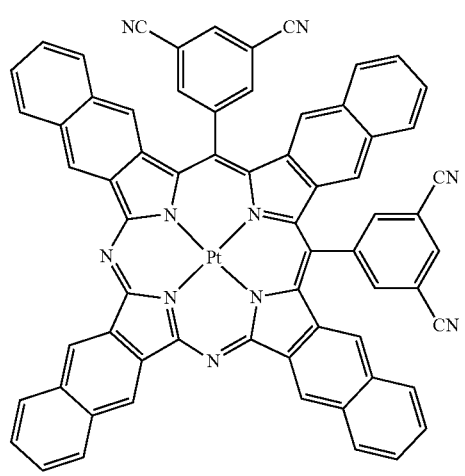

81
-continued
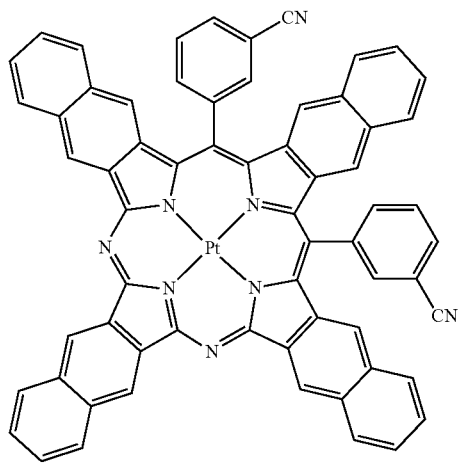
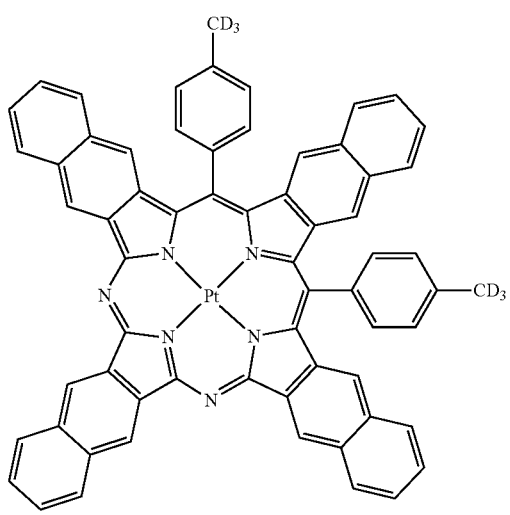
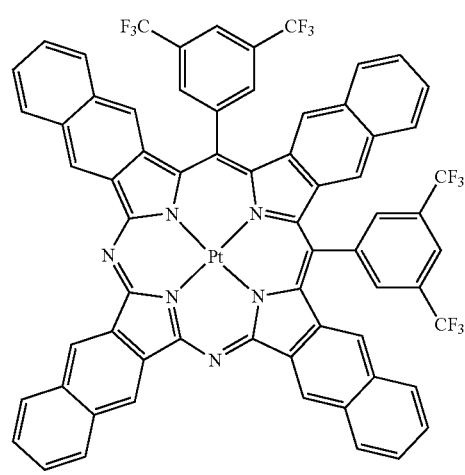
82
-continued
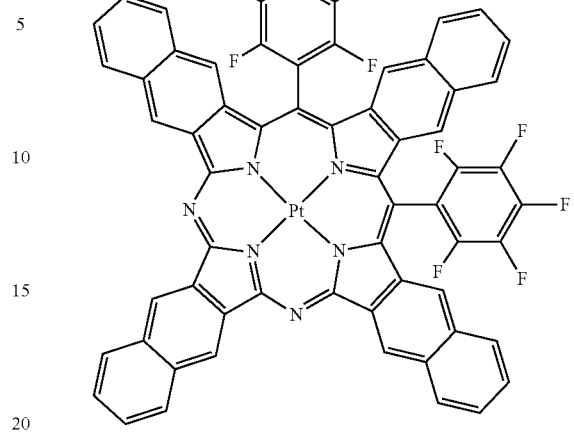
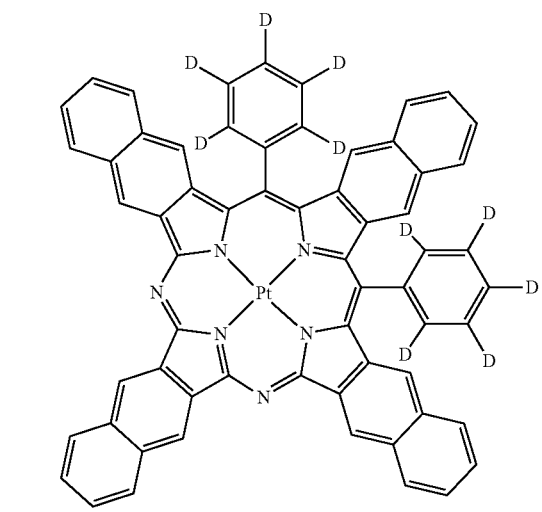
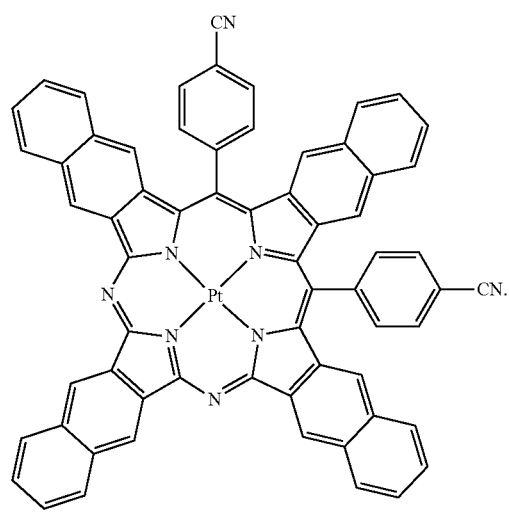
5. The complex of claim 1, represented by one of the following structures:

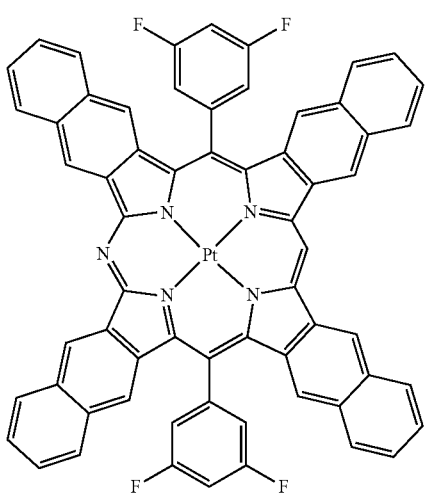
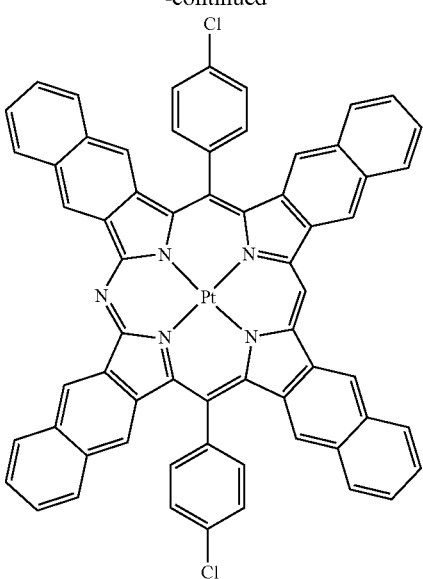
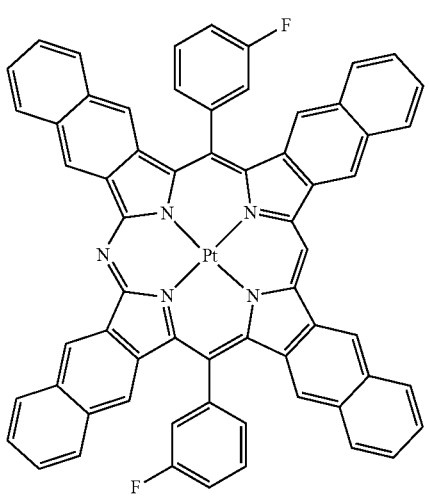
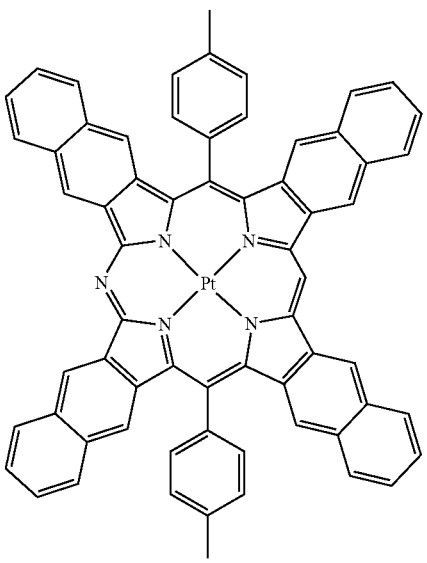
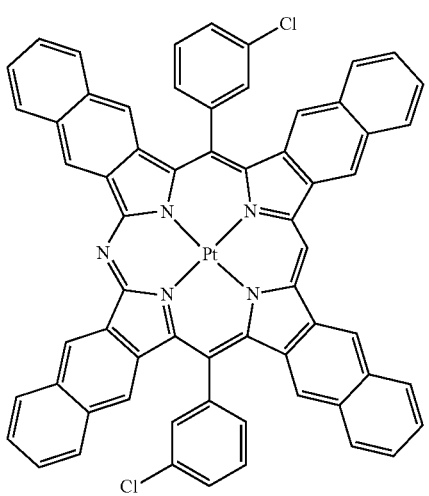
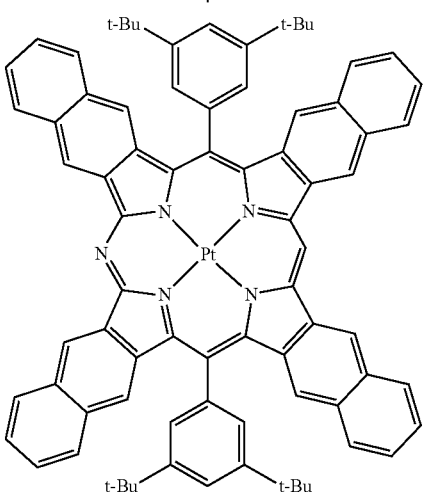

85
-continued
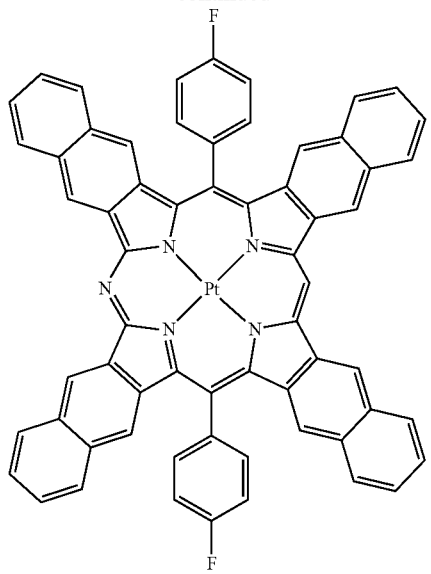
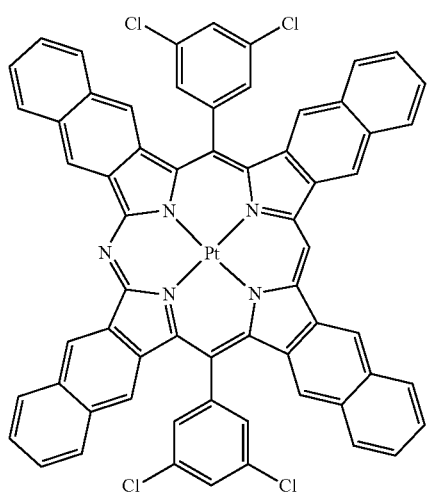
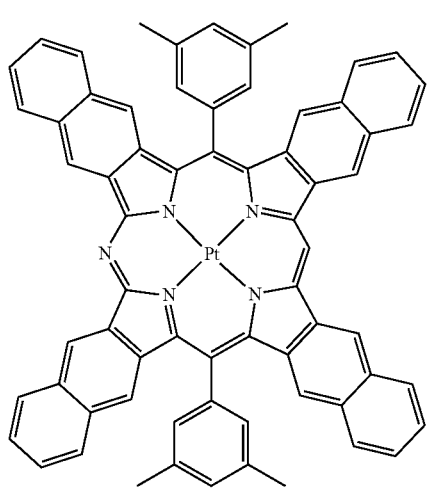
86
-continued
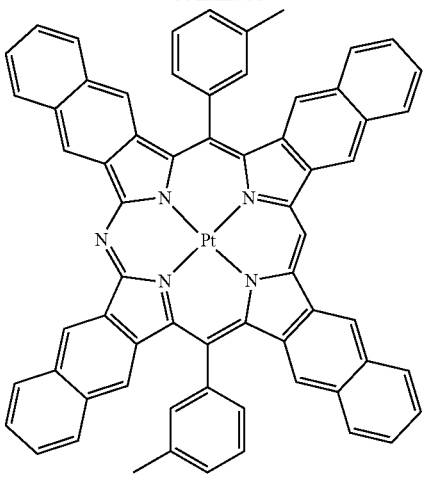
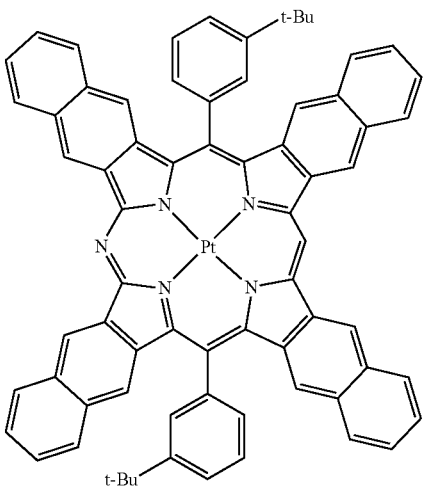
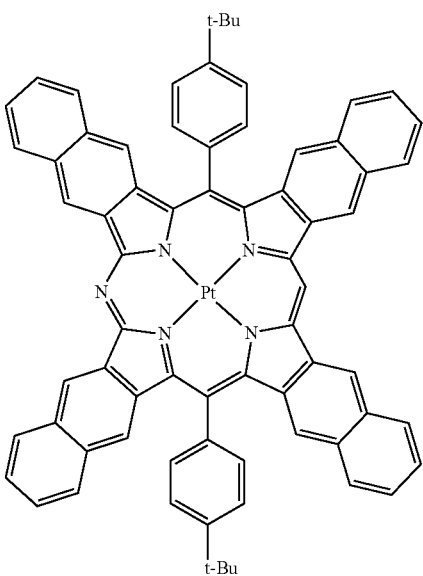

-continued
87
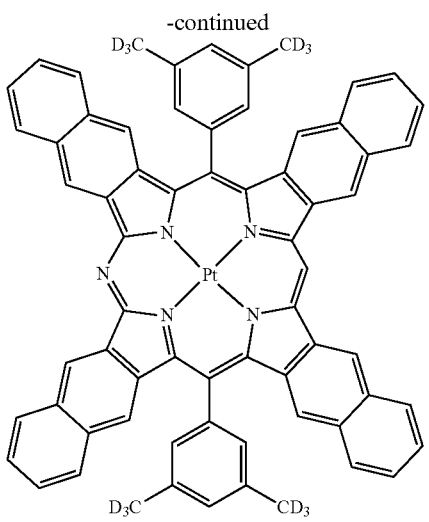
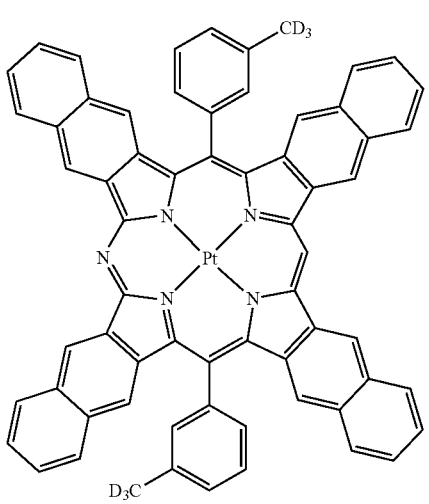
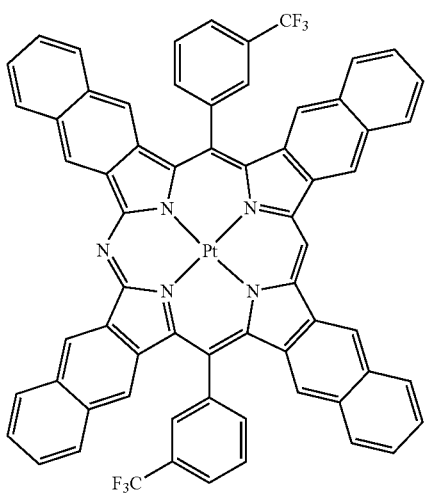
-continued
88
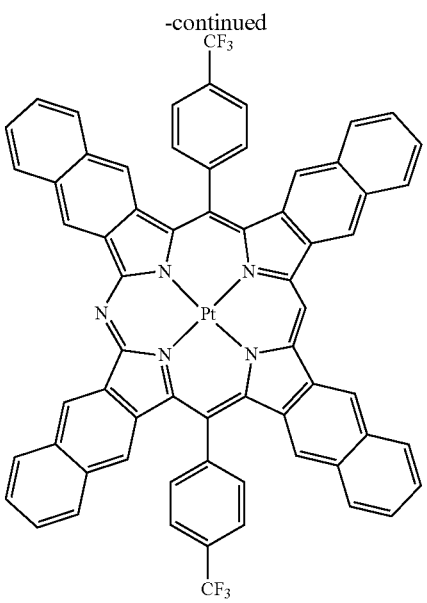
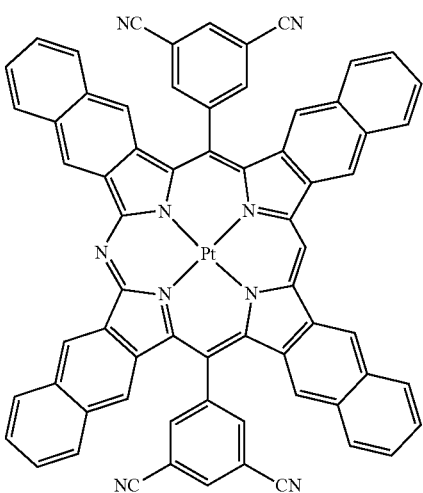
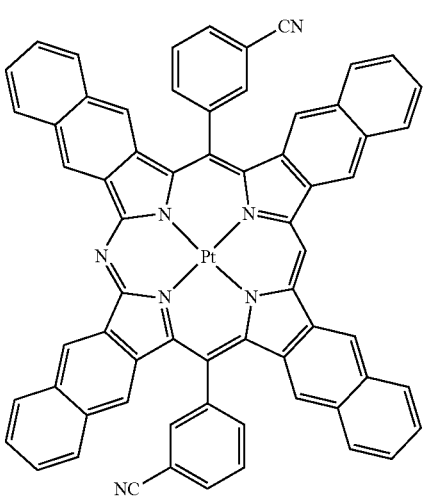

-continued
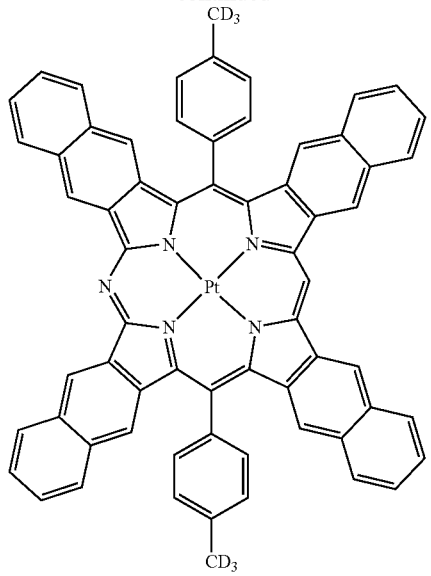
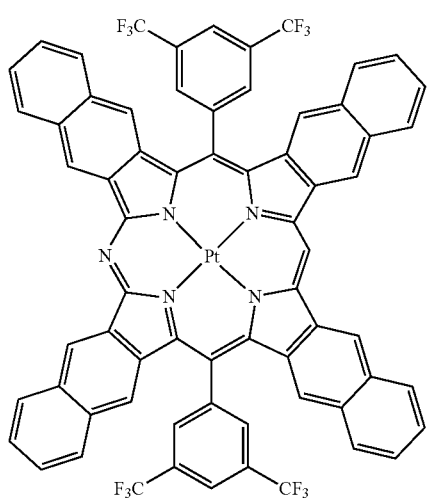
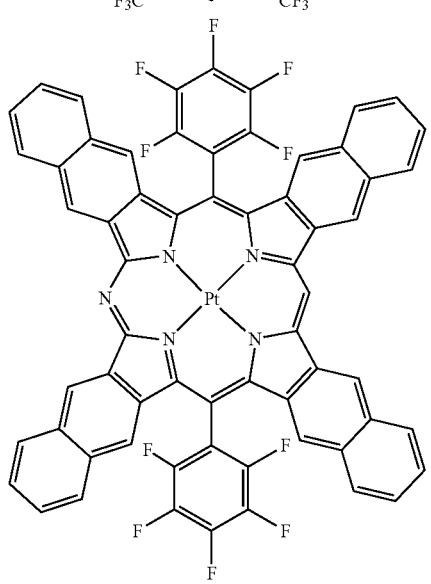
-continued
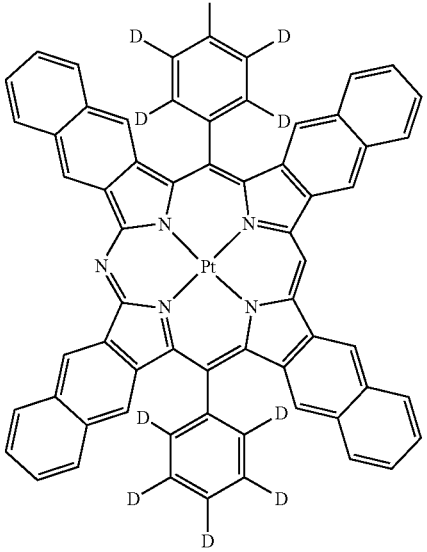
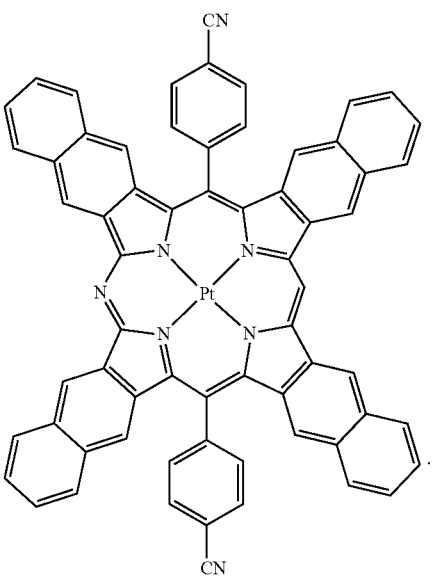
6. The complex of claim 1, represented by one of the following structures:

91
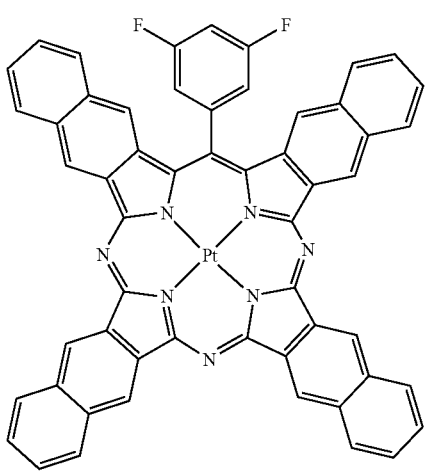
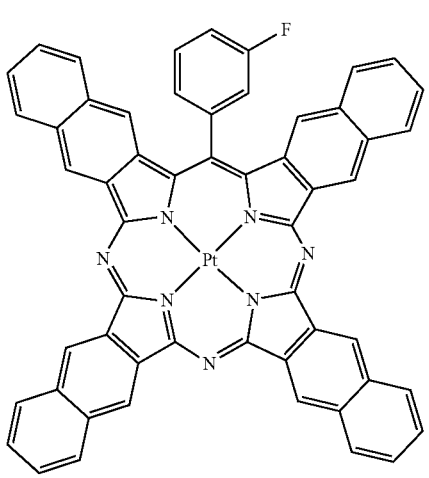
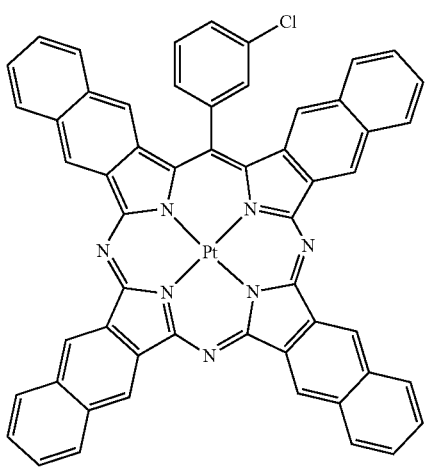
92
-continued
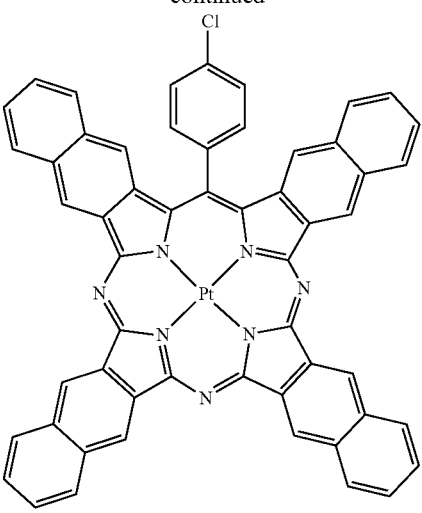
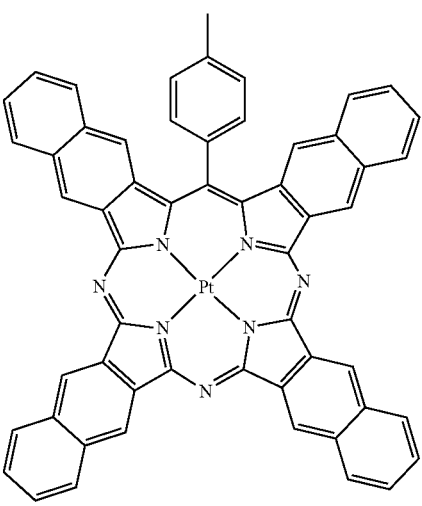
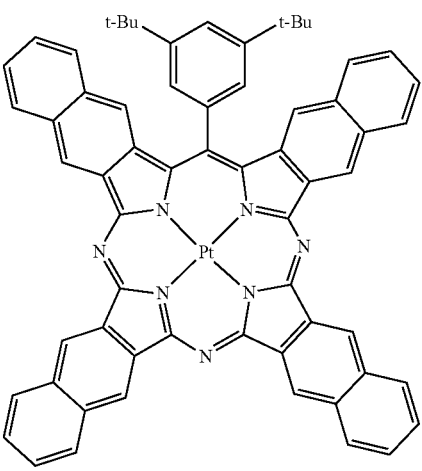

93
-continued
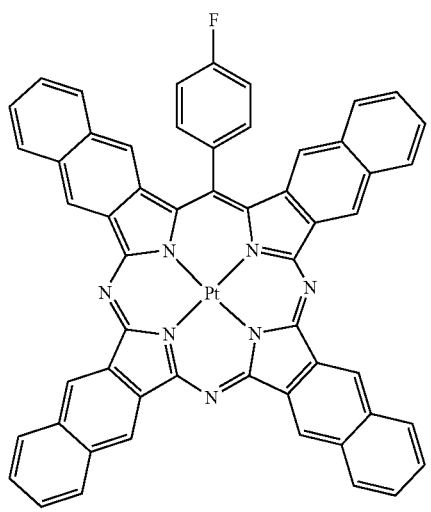
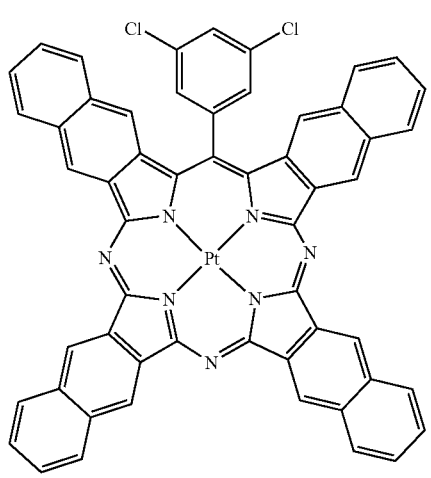
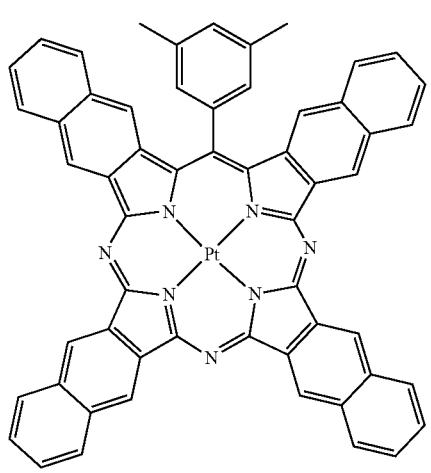
94
-continued
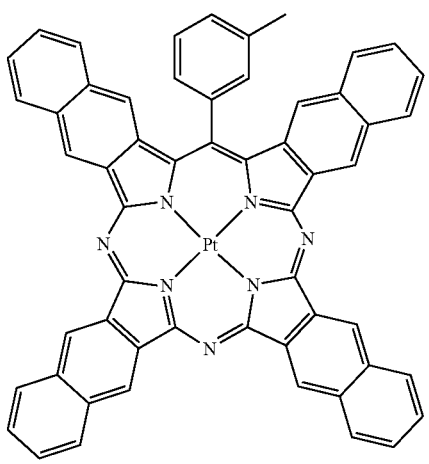
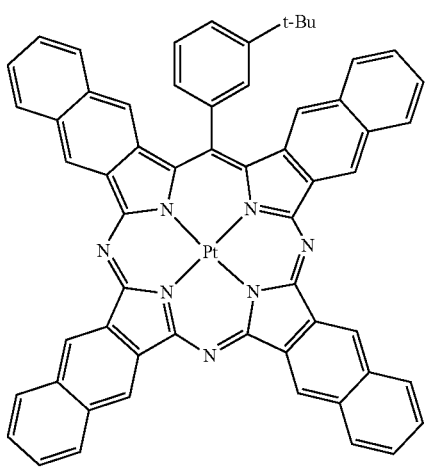
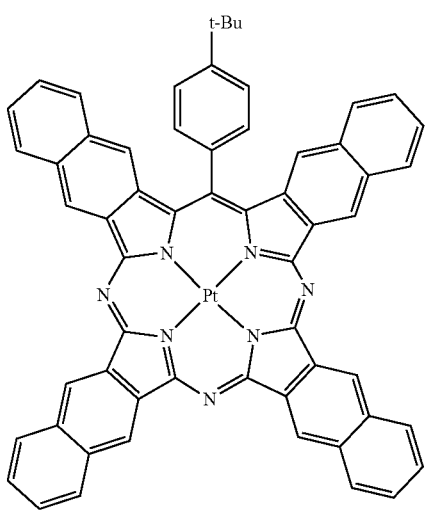

95
-continued
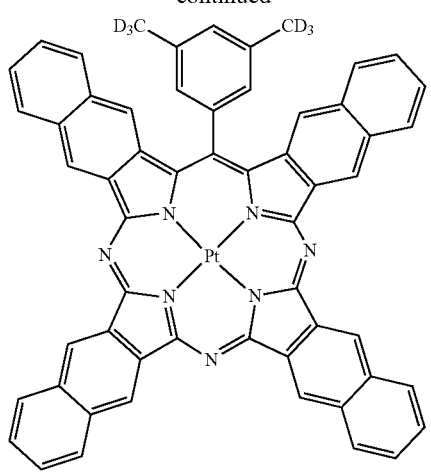
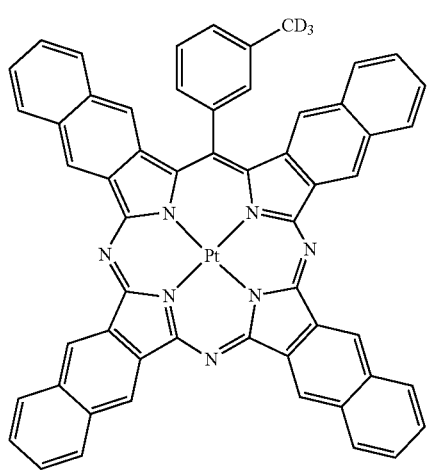
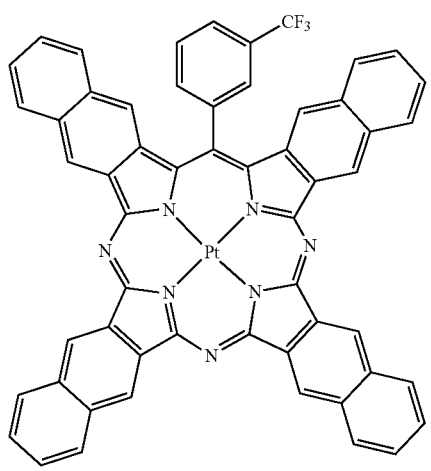
96
-continued
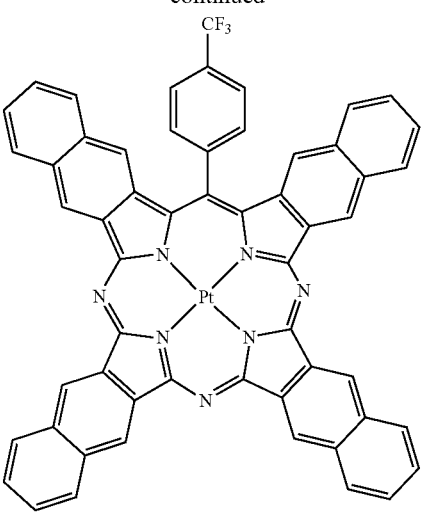
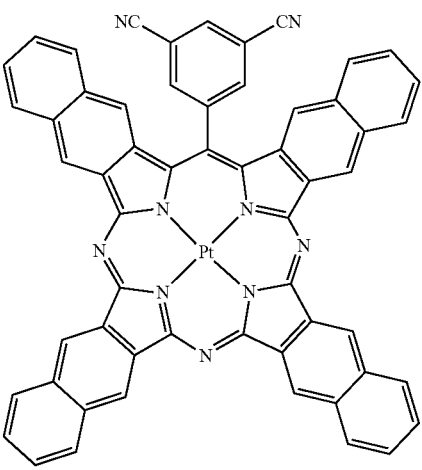
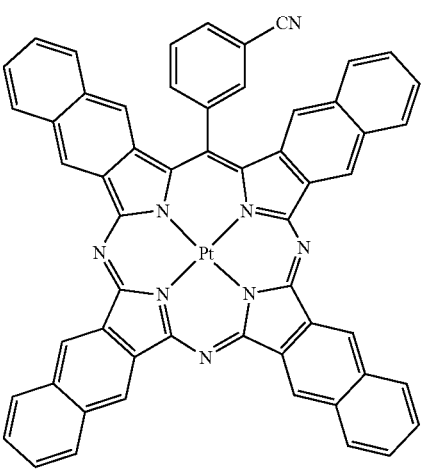

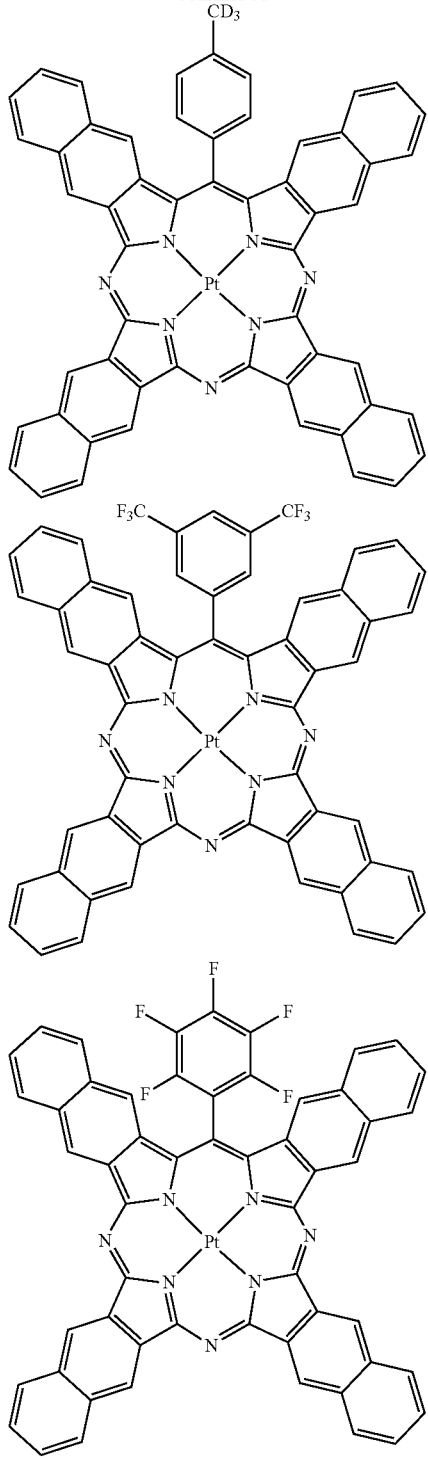

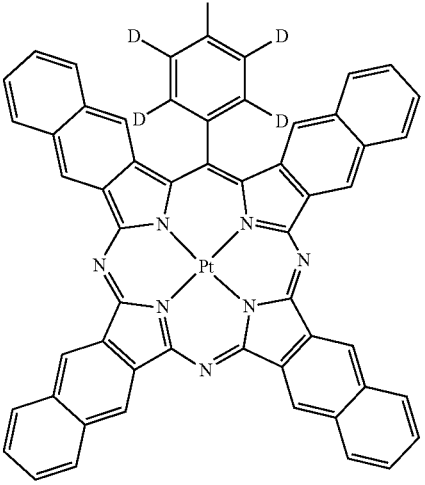

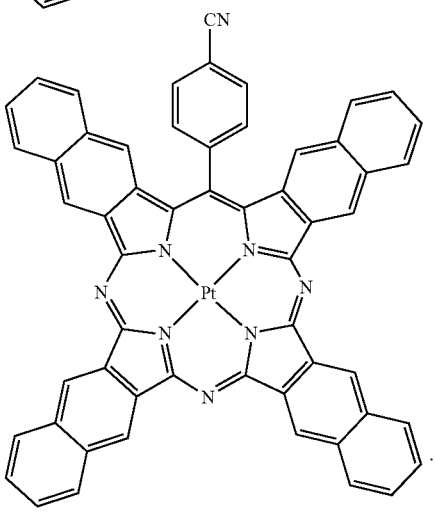

7. An optoelectronic device comprising the complex of claim 1.

8. The optoelectronic device of claim 7, wherein the optoelectronic device is an organic light-emitting diode.

9. The complex of claim 1, wherein the complex is represented by General Formula I and at least one of $R^5$ to $R^8$ is present and represents a substituent selected from the group consisting of chloride, methyl-d3, and phenyl-d5.

10. The complex of claim 1, wherein the complex is represented by General Formula I and at least one occurrence of n is 2 and the corresponding substituents are fluoride at the 3- and 5-positions.

11. The complex of claim 1, wherein the complex is represented by General Formula II, General Formula III, General Formula IV, or General Formula V.

* * * * *